US012790371B2

(12) United States Patent
Linghu et al.

(10) Patent No.: US 12,790,371 B2

(45) Date of Patent: Nov. 10, 2026

(54) INTRACELLULAR MOLECULAR RECORDING AND MEMORY VIA PROTEIN SELF-ASSEMBLY

(71) Applicant: Massachusetts Institute of Technology, Cambridge, MA (US)

(72) Inventors: Changyang Linghu, Cambridge, MA (US); Edward S. Boyden, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 137 days.

(21) Appl. No.: 18/045,624

(22) Filed: Oct. 11, 2022

(65) Prior Publication Data

US 2023/0250139 A1 Aug. 10, 2023

Related U.S. Application Data

(60) Provisional application No. 63/254,829, filed on Oct. 12, 2021.

(51) Int. Cl.

| | |
|---|---|
| ***C12N 15/63*** | (2006.01) |
| ***C07K 14/245*** | (2006.01) |
| ***G01N 33/50*** | (2006.01) |

(52) U.S. Cl.

CPC ............ *C07K 14/245* (2013.01); *C12N 15/63* (2013.01); *G01N 33/5023* (2013.01); *C07K 2319/24* (2013.01); *C07K 2319/735* (2013.01)

(58) Field of Classification Search

CPC .............. C07K 14/245; C07K 2319/24; C07K 2319/735; C07K 2319/00; C07K 2319/42; C07K 2319/60; C12N 15/63; G01N 33/5023

See application file for complete search history.

(56) References Cited

U.S. PATENT DOCUMENTS

2021/0080472 A1 3/2021 Linghu

FOREIGN PATENT DOCUMENTS

WO WO-2020086793 A1 * 4/2020 ............... C07K 1/00

OTHER PUBLICATIONS

Brizzard, B., Epitope tagging, (2008) BioTechniques 44:693-695 (Year: 2008).*

Chamberlin et al., Recombinant adeno-associated virus vector: use for transgene expression and anterograde tract tracing in the CNS, 1998, Brain Res., 793(1-2): 169-175 (Year: 1998).*

Anonymous, Database UniProt KB [Online] Apr. 7, 2021, "RecName: Full=Isoaspartyldi peptidase", XP093011681, retrieved from NCBI accession No. P39377 Database accession No. P39377.1, 6 pages.

Ceccatelli, S. et al. "Expression of c-Fos immunoreactivity in transmitter-characterized neurons after stress" Proc. Natl. Acad.Sci. U. S. A. 86, 9569-9573 (1989).

(Continued)

*Primary Examiner* — Robert B Mondesi

*Assistant Examiner* — Naghmeh Nina Moazzami

(74) *Attorney, Agent, or Firm* — Pierce Atwood LLP; Christopher A. Baxter

(57) ABSTRACT

The invention, in some aspects, includes compositions encoding expression-recording islands (XRIs), compositions comprising XRIs, and methods for using XRIs for intracellular molecular recording.

11 Claims, 33 Drawing Sheets

Specification includes a Sequence Listing.

(56) References Cited

OTHER PUBLICATIONS

Chan M. M. et al.: "Molecular recording of mammalian embryogenesis", Nature, Nature Publishing Group UK, London, vol. 570, No. 7759, May 13, 2019, pp. 77-82, XP036900491, ISSN: 0028-0836, DOI:10. 1038/S41586-019-1184-5.
Chen, F., et al., "Overcoming the limits of the microscope" Science Jan. 30, 2015 Vol 347, (6221) 543-548 DOI: 10.1126/science. 1260088.
Cranfill, P. J. et al. "Quantitative assessment of fluorescent proteins" Nat. Methods 2016 137 13,557-562 (2016).
Gao, R. et al. "Cortical column and whole-brain imaging with molecular contrast and nanoscale resolution" Science (80-.). 363, (2019).
Garcia-Seisdedos, et al. "Proteins evolve on the edge of supramolecular self-assembly" Nature 548, 244 (2017).
Greenwald, E. C., et al. "Genetically Encoded Fluorescent Biosensors Illuminate the Spatiotemporal Regulation of Signaling Networks" Chem. Rev. 118, 11707-11794 (2018).
Guenthner, C. J., et al., "Permanent genetic access to transiently active neurons via TRAP: targeted recombination in active populations" Neuron 78, 773 (2013).
International Search Report and Written Opinion from the International Searching Authority dated Jan. 20, 2023 from corresponding International Patent Application No. PCT/US2022/077892 Filed on Oct. 11, 2022.
Joo, J.-Y., et al., "Stimulus-specific combinatorial functionality of neuronal c-fos enhancers" Nat. Neurosci. 2016 191 19, 75-83 (2015).
Kapust, R. B. et al. "*Escherichia coli* maltose-binding protein is uncommonly effective at promoting the solubility of polypeptides to which it is fused" Protein Sci. 8, 1668-1674 (1999).
Kaspar, B. K. et al. Adeno-associated virus effectively mediates conditional gene modification in the brain. Proc. Natl Acad. Sci. USA 99, 2320 (2002).
Kawashima, T., et al., "A new era for functional labeling of neurons: activity-dependent promoters have come of age" Frontiers in Neural Circuits 8, 37 (2014).
Kim, J. H. et al. "High Cleavage Efficiency of a 2A Peptide Derived from Porcine Teschovirus-1 in Human Cell Lines, Zebrafish and Mice" PLoS One6, e18556 (2011).
Klapoetke, N. C. et al. "Independent Optical Excitation of Distinct Neural Populations" Nat. Methods 11,338-46 (2014).
Lin, D. et al. "Functional identification of an aggression locus in the mouse hypothalamus" Nature 470, 221 (2011).
Linghu C. et al: "Recording of cellular physiological histories along optically readable self-assembling protein chains", bioRxiv, Oct. 13, 2021, pp. 1-42, XP093011859, DOI: 10.1101/2021.10.13.464006 Retrieved from the Internet: URL: https://www.biorxiv.org/content/10.1101/2021.10.13.464006v1.full.pdf.
Linghu C. et al: "Recording of cellular physiological histories along optically readable self-assembling protein chains", Anature Biotechnology, Jan. 2, 2023, XP093011174, New York ISSN: 1087-0156, DOI:10.1038/s41587-022-01586-7.
Linghu C. et al: "Spatial Multiplexing of Fluorescent Reporters for Imaging Signaling Network Dynamics", Cell, Elsevier, Amsterdam NL, vol. 183, No. 6, Nov. 23, 2020 , p. 1682, XP086400367, ISSN: 0092-8674, DOI:10.1016/J.CELL.2020.10.035.
Love, M. I., et al., "Moderated estimation of fold change and dispersion for RNA-seq data with DESeq2" Genome Biol. 15, 1-21 (2014).
Malik, A. N. 5 et al. "Genome-wide identification and characterization of functional neuronal activity-dependent enhancers" Nat. Neurosci. 17, 1330 (2014).
Matsuda, T., et al. "Controlled expression of transgenes introduced by in vivo electroporation " Proc. Natl. Acad. Sci. U. S. A. 104, 1027-1032 (2007).
Murray, E. et al. "Simple, Scalable Proteomic Imaging for High-Dimensional Profiling of Intact Systems" Cell 163, 1500-14 (2015).
Piatkevich, K. D. et al. "A robotic multidimensional directed evolution approach applied to fluorescent voltage reporters" Nat. Chem. Biol. 14, 352-360 (2018).
Ragan, T. et al. "Serial two-photon tomography for automated ex vivo mouse brain imaging" Nat. Methods 2012 93 9, 255-258 (2012).
Reuten, R. et al. "Maltose-Binding Protein (MBP), a Secretion-Enhancing Tag for Mammalian Protein Expression Systems" PLoS One 11, e0152386 (2016).
Rodríguez-Berdini, L. et al. "The moonlighting protein c-Fos activates lipid synthesis in neurons, an activity that is critical for cellular differentiation and cortical development" J. Biol. Chem. 295, 8808-8818 (2020).
Roy, D. S. et al. "Memory retrieval by activating engram cells in mouse models of early Alzheimer's disease" Nat. 2016 5317595531, 508-512 (2016).
Shen, H. et al. "De novo design of self-assembling helical protein filaments" Science 362, 705 (2018).
Tyssowski, K. M. et al. "Different Neuronal Activity Patterns Induce Different Gene Expression Programs" Neuron 98, 630-546.e11 (2018).
Zincarelli, C., et al., "Analysis of AAV serotypes 1-9 mediated gene expression and tropism in mice after systemic injection" Mol. Ther. 16, 1073-1080 (2008).
Fox, J.D., et al., "Single amino acid substitutions on the surface of *Escherichia coli* maltose-binding protein can have a profound impact on the solubility of fusion proteins." Protein Science 10.3 (2001): 622-630.

* cited by examiner

INTRACELLULAR LINEAR PROTEIN SELF-ASSEMBLY

DHF40-HA

2VYC(K491L, D494L,D497L)-HA

STEP 1: DETERMINE CENTERLINE

STEP 2: PLOT INTENSITY PROFILE

STEP 3: SPLIT THE INTENSITY PROFILES INTO TWO HALVES AT THE GEOMETRIC CENTER, CALCULATE FLAG SIGNAL VS HA LINE INTEGRAL FOR EACH HALF, AND AVERAGE THE TWO FLAG SIGNALS

STEP 4: SEARCH FOR THE 'OPTIMAL SHIFT POINT' THAT RESULTS IN THE LEAST DIFFERENCE BETWEEN THE TWO FLAG SIGNALS AFTER SPLITTING

STEP 5: SPLIT THE INTENSITY PROFILES INTO TWO HALVES AT THE OPTIMAL SPLIT POINT, CALCULATE FLAG SIGNAL VS HA LINE INTEGRAL FOR EACH HALF, AND AVERAGE THE TWO FLAG SIGNALS

INTRACELLULAR MOLECULAR RECORDING AND MEMORY VIA PROTEIN SELF-ASSEMBLY

RELATED APPLICATIONS

This application claims benefit under 35 U.S.C. § 119(e) of U.S. Provisional application Ser. No. 63/254,829 filed Oct. 12, 2021, the disclosure of which is incorporated by reference herein in its entirety.

GOVERNMENT INTEREST

This invention was made with government support under grants 1R24MH106075, R44EB021054, 1R01DA045549, 1R01MH114031, 2R01DA029639, 1R01EB024261, 1DP1NS087724, and 1R01GM104948 awarded by the National Institutes of Health; grant W911NF1510548 awarded by the U.S. Army Research Laboratory and the U.S. Army Research Office; and grant CBET 1344219 awarded by the National Science Foundation. The government has certain rights in the invention.

FIELD OF THE INVENTION

The invention, in some aspects, includes compositions and methods for molecular recording protein expression and identifying protein expression records in cells.

Reference to an Electronic Sequence Listing

The contents of the electronic sequence listing (SequenceListingUS.xml; Size: 40,942 bytes; and Date of Creation: Oct. 11, 2022) is herein incorporated by reference in its entirety.

BACKGROUND OF THE INVENTION

Reading out biological signals and processes that take place over time, in living cells, intact organs, and organisms, is essential to advancing biological research, both basic science and translationally oriented. The imaging of genetically encoded fluorescent signal reporters, for example, enables specific biological activities to be monitored in real time in living cells [Greenwald, E. C., etal. *Chem. Rev.* 118, 11707-11794 (2018)]. However, long-term live imaging is laborious and equipment intensive, because a single microscope often has to be monopolized for the duration of the experiment, and furthermore the number of cells that can be observed is limited by the performance of live imaging methods, which are not as scalable as fixed-tissue imaging methods, which can benefit from sectioning, clearing, expansion, and other techniques that improve the number of cells that can be surveyed [Murray, E. et al. *Cell* 163, 1500-14 (2015); Ragan, T. et al. *Nat. Methods* 2012 93 9, 255-258 (2012); Gao, R. et al. *Science* (80-.). 363, (2019). Snapshot methods, that perform RNA FISH [Lin, D. et al. *Nature* 470, 221 (2011)], or protein immunostaining [Ceccatelli, S. et al. *Proc. Natl. Acad. Sci. U.S.A.* 86, 9569-9573 (1989)], can enable one (and sometimes two) time points of a physiological signal to be inferred in fixed cells, but cannot support continuous recording of physiological signals for later fixed-cell readout.

SUMMARY OF THE INVENTION

According to an aspect of the invention, a composition including a sequence encoding an expression-recording island (XRI) is provided, when the composition is expressed, each encoded XRI includes one or more independently selected self-assembling filament-forming monomer, zero, one, or more independently selected detectable tag, and zero, one, or more independently selected protein spacer. In some embodiments, the self-assembling filament-forming monomer is an engineered protein. In certain embodiments, the self-assembling filament-forming monomer includes a 1POK or DHF40 protein. In some embodiments, the detectable tag includes an epitope tag. In some embodiments, the epitope tag is a human influenza hemagglutinin (HA) tag. In certain embodiments, the protein spacer includes a monomeric protein. In some embodiments, the monomeric protein comprise a mEGFP or maltose binding protein (MBP). In some embodiments, the encoded XRI, when expressed is capable of forming a linear protein assembly. In some embodiments, the linear protein assembly includes the protein spacer fused to a lateral edge of the filament forming monomer. In some embodiments, the encoded XRI comprises a self-assembling filament-forming monomer, a detectable tag, and optionally a protein spacer. In some embodiments, the encoded XRI includes 1, 2, 3, or 4 independently selected self-assembling filament forming monomers. In some embodiments, the encoded XRI includes 0, 1, 2, 3, or 4 independently selected detectable labels. In some embodiments, the encoded XRI includes 0, 1, 2, 3, or 4 independently selected protein spacers.

According to another aspect of the invention, a vector is provided, the vector including a nucleotide sequence encoding the encoded expression-recording island (XRI) composition of any embodiment of the aforementioned aspect of the invention.

According to another aspect of the invention, a cell is provided, the cell including any embodiment of an aforementioned vector of the invention. In certain embodiments, the cell is a vertebrate cell, a mammalian cell, and/or a human cell. In some embodiments, the cell is an excitable cell. In some embodiments, the cell is one or more of a neuron, a CNS cell, a PNS cell, a muscle cell, an endocrine cell, an immune system cell, an epidermal cell, a kidney cell, a liver cell, and a cardiac cell. In certain embodiments, the cell is an in vitro cell. In certain embodiments, the cell is in a subject. In some embodiments, the cell is an ex vivo cell. In some embodiments, the cell is a brain cell in a subject.

According to another aspect of the invention, an adeno-associated virus (AAV) including the encoded expression-recording island (XRI) composition of any embodiment of a composition of an aforementioned aspect of the invention is provided.

According to another aspect of the invention, a cell is provided, the cell including any embodiment of an aforementioned AVV of the invention. In some embodiments, the cell is a vertebrate cell, a mammalian cell, and/or a human cell. In certain embodiments, the cell is an excitable cell. In certain embodiments, the cell is one or more of a neuron, a CNS cell, a PNS cell, a muscle cell, an endocrine cell, an immune system cell, an epidermal cell, a kidney cell, a liver cell, and a cardiac cell. In some embodiments, the cell is an in vitro cell. In some embodiments, the cell is in a subject. In certain embodiments, the cell is an ex vivo cell. In some embodiments, the cell is a brain cell in a subject.

According to another aspect of the invention, a method of identifying an expression history record in a cell is provided, the method including: expressing in a cell or in a plurality of cells the expression-recording island (XRI) encoded by one, two, or more independently selected XRI-encoding compositions of any embodiment of any aforementioned composition of the invention, and detecting the expressed XRI(s) in the one cell or the plurality of cells at a time point, wherein the detected expressed XRI(s) identify an expression record of the XRI(s) in the cell or the plurality of cells at the time point. In some embodiments, detecting the expressed XRI(s) in the plurality of cells includes detecting the expressed XRI(s) in one or more cells obtained from the plurality of cells. In some embodiments, the independently selected compositions each includes a different encoded XRI. In certain embodiments, the method also includes detecting the expressed XRI(s) in the plurality of cells at one or more additional independently selected time points providing a plurality of detections of detected expressed XRI(s) and identifying an expression record of the XRI(s) in the plurality of cells across the plurality of time points. In some embodiments, the method also includes comparing the identified expression record of the XRI(s) in the plurality of cells at two or more of the plurality of time points, wherein a difference between in the expressed XRI(s) detected at two or more of the plurality of time points identifies a change in the expression record of the XRI(s) in the plurality of cells. In some embodiments, the method also includes fixing the cells(s) prior to the detecting. In some embodiments, the detecting includes determining an amount of the expressed XRI. In certain embodiments, the detecting includes determining a pattern of epitope tags in the expressed XRI. In some embodiments, the detecting includes determining the identity of one or more epitope tags in the expressed XRI. In some embodiments, determining the amount of the expressed XRI(s) includes determining an amount of the detectable tag in the XRI(s). In certain embodiments, the time interval between any two of the plurality of the independently selected time points is at least 1 sec, 5 sec, 10 sec, 15, sec., 30 sec, 45 sec, 1 min, 30 min, 60 min, 240 min, 480 min, 1 day, 2, days, 3 days, 4 days, 5 days, 6 days, 7 days, 8 days, 9 days, 10 days, 15 days, 20 days, 30 days, 60 days or 90 days. In some embodiments, the detected expressed of XRI(s) corresponds to a temporal history of expression of the XRI(s) in the cell or the plurality of cells. In some embodiments, the cell is a vertebrate cell, a mammalian cell, and/or a human cell. In some embodiments, the cell is an excitable cell. In certain embodiments, the cell is one or more of a neuron, a CNS cell, a PNS cell, a muscle cell, an endocrine cell, an immune system cell, an epidermal cell, a kidney cell, a liver cell, and a cardiac cell. In some embodiments, the cell is an in vitro cell. In some embodiments, the cell is in a subject. In certain embodiments, the cell is an ex vivo cell. In some embodiments, each of the encoded XRIs include 0, 1, 2, 3, 4, or more independently selected detectable labels. In some embodiments, the number of detectable labels in each of the encoded XRIs is independently selected. In some embodiments, the encoded XRIs include 0, 1, 2, 3, 4, or more independently selected protein spacers. In some embodiments the number of protein spacers in each of the encoded XRIs is independently selected According to another aspect of the invention, a method of identifying an effect of a candidate stimulus on expression in a cell, is provided, the method including: preparing a plurality of cells expressing the expression-recording island (XRI) encoded by any embodiment of an aforementioned composition of the invention; exposing the plurality of cells expressing the XRI to a candidate stimulus; detecting the expressed XRI in one or more cells in the exposed plurality of cells, and comparing the detected expressed XRI in the one or more cells to a control expressed XRI, wherein the control XRI is the expressed XRI in a cell including the expressed XRI but not exposed to the candidate stimulus; and wherein a difference in the detected expressed XRI in the exposed cells compared to the control XRI identifies an effect of the candidate stimulus on the XRI expression. In some embodiments, the detecting includes determining an amount of XRI expression. In some embodiments, the exposing to the candidate stimulus includes one or both of indirectly and directly contacting the plurality of cells with one or more of: electrical stimulus, a chemical stimulus, a biological stimulus, an inhibitory stimulus, an excitatory stimulus, a signaling molecule, a signaling chemical, a pharmaceutical stimulus, a cellular stimulus, a temperature stimulus, or a light stimulus. In some embodiments, the cell is a vertebrate cell, a mammalian cell, and/or a human cell. In certain embodiments, the cell is an excitable cell. In some embodiments, the cell is in a subject. In certain embodiments, the cell is in culture. In some embodiments, the cell is an engineered cell. In some embodiments, the cell is one or more of a neuron, a CNS cell, a PNS cell, a muscle cell, an endocrine cell, an immune system cell, an epidermal cell, a kidney cell, a liver cell, and a cardiac cell. In certain embodiments, the cell is an in vitro cell. In some embodiments, the XRI includes 0, 1, 2, 3, or 4 independently selected detectable labels. In some embodiments, the XRI includes 0, 1, 2, 3, or 4 independently selected protein spacers. In some embodiments, the XRI includes 1, 2, 3, or 4 independently selected self-assembling filament-forming monomers.

According to another aspect of the invention, a composition including an expression-recording island (XRI) protein is provided, the XRI protein includes one or more self-assembling filament-forming monomers; zero, one, or more independently selected detectable tags; and zero, one, or more independently selected protein spacers. In some embodiments, the composition also includes zero, one, or more additional independently selected self-assembling filament-forming monomer(s). In some embodiments, the XRI is encoded by an embodiment of any aforementioned composition of the invention.

According to another aspect of the invention, a cell is provided, the cell including an embodiment of any aforementioned XRI protein composition of the invention. In certain embodiments, the cell is a vertebrate cell. In certain embodiments, the cell is a mammalian cell. In some embodiments, the cell is a human cell. In some embodiments, the cell is an excitable cell. In certain embodiments, the cell is one or more of a neuron, a CNS cell, a PNS cell, a muscle cell, an endocrine cell, an immune system cell, an epidermal cell, a kidney cell, a liver cell, and a cardiac cell. In certain embodiments, the cell is an in vitro cell. In some embodiments, the cell is in a subject. In certain embodiments, the cell is an ex vivo cell. In some embodiments, the cell is a brain cell in a subject.

DESCRIPTION OF THE DRAWINGS

FIG. 1A is a schematic diagram of intracellular linear protein self-assembly. FIG. 1B is a schematic diagram of bi-directional elongating intracellular linear protein self-assembly for encoding, storing, and reading out biological information. Upper panel: Lightest shading indicates components on the self-assembly whose expression is constitutive over time; darkest shading indicates components on the self-assembly whose expression is dependent on biological events of interest over time. Lower panel: line indicates density along the self-assembly of the components whose expression is dependent on biological events of interest over time. FIG. 1C us a schematic diagram of variants of self-assembling proteins. 1POK (E239Y), a filament-forming self-assembling protein; mEGFP, monomeric enhanced green fluorescent protein; MBP tag, maltose binding protein tag; AA, amino acid; XRI, the variant that was selected as the XRI design throughout this paper (see Table 1 for sequences of the motifs; see Table 2 for all tested constructs). FIG. 1D provides representative confocal images of cultured mouse hippocampal neurons expressing self-assembling protein variants with the epitope tag HA, taken after fixation, Nissl staining against the soma, and immunostaining against the HA tag. Scale bar, 5 μm throughout this figure. Rectangular panels at the bottom, enlarged views of regions marked in rectangles in the top row of square panels. FIG. 1E is schematic diagram of protein self-assemblies without (left) and with (right) an insulator component fused to each of the filament forming subunits. Arrows with different sizes, growth directions of protein self-assemblies, with arrow sizes indicating growth rates; old, subunits that bound to the protein self-assembly earlier; new, subunits that are binding to the protein self-assembly currently. FIG. 1F is schematic of the protein self-assembly and the constructs in the chemically induced gene expression experiment. Variant-HA, self-assembling protein variant (1POK, 1POK-mEGFP, or 1POK-MBP) with the epitope tag HA; Variant-FLAG, self-assembling protein variant with the epitope tag FLAG; Ubiquitin C (UBC) promoter, human ubiquitin promoter; Syn, human synapsin promoter; black and white triangles, lox sites in the FLEX construct; 4-OHT, 4-hydroxytamoxifen; $T_{4\text{-}OHT}$, the time when cells are treated with 4-OHT; $T_{fixation}$, the time when cells are fixed. FIG. 1G provides representative confocal images of cultured mouse hippocampal neurons expressing constructs (shown in bottom left of FIG. 1F), taken after fixation, Nissl staining, and immunostaining against the HA tag and the FLAG tag. Ttransfeetion, the time when the constructs are delivered to cells via DNA transfection. Three rows of rectangular panels at the bottom, enlarged views of regions marked in rectangles in the top row of square panels. FIG. 1H shows representative confocal images of a live cultured mouse hippocampal neuron expressing mEGFP-P2A-XRI-HA. Top left, construct schematic; bottom left, image taken 7 days after AAV transduction under the GFP channel; right, images of the XRI protein self-assembly in the same neuron as in the bottom left taken 1-7 days (1 d-7 d) after AAV transduction, showing the GFP channel. FIG. 1I and FIG. 1J are graphs showing normalized length (FIG. 1I) and width (FIG. 1J) of XRI versus time after AAV transduction (n=14 XRIs from 8 neurons from 1 culture; length and width were normalized to the maximum values over time, respectively). Centerline, mean; shaded boundary, standard deviation. Insets, box plots of absolute length and width of XRI at 7 days after AAV transduction; middle line in box plot, median; box boundary, interquartile range; whiskers, 10-90th percentile.

FIG. 2A-B shows representative confocal images of cultured mouse hippocampal neurons expressing (FIG. 1A) DHF40 or (FIG. 1B) 2VYC(K491L,D494L,D497L) with epitope tag HA, taken after fixation, Nissl staining, and immunostaining against the HA tag. Scale bars, 5 μm. Rectangular panels at the bottom, enlarged views of regions marked in orange rectangles in the top row of square panels. See Table 1 for sequences of the motifs; see Table 2 for all tested constructs. FIG. 2C provides a representative confocal image in the GFP channel of cultured mouse hippocampal neurons 7 days after AAV transduction of AAV9-UBC-mEGFP-P2A-XRI-HA. Bicistronic co-expression of mEGFP with XRI (via P2A) allows estimations of the level of AAV delivery in individual cells using GFP intensity in the cytosol. Arrows indicate representative neurons with fiber-like structures (i.e., successful formation of XRI assemblies; lowest arrow), punctum-like structures (highest arrow), or no resolvable structure (middle arrow). Scale bar, 20 μm. FIG. 2D provides a plot on the left that is a scatter plot of the GFP intensity of soma-localized XRI versus cytosolic GFP intensity; and a plot on the right that is a box plot of the ratio of the GFP intensity of soma-localized XRI to the cytosolic GFP intensity; n=134 XRIs from 51 neurons with soma-localized XRIs from 4 fields of view from 1 culture. Throughout this figure: cytosolic GFP intensities were measured by averaging the pixel intensity values across pixels within the soma but outside the XRIs, from images captured under the same imaging condition in the GFP channel; XRI GFP intensities were measured by averaging the pixel intensity values along individual XRIs in these images. Black line, line fit from linear regression. FIG. 2E provides a histogram of the number of soma-localized XRIs per neuron, among GFP-positive neurons (n=64 neurons from 4 fields of view from 1 culture), 7 days after AAV transduction of AAV9-UBC-mEGFP-P2A-XRI-HA. ‘80%’ with an arrow, 80% of the neurons had soma-localized XRI(s). FIG. 2F is a scatter plot of the number of soma-localized XRIs per neuron versus the cytosolic GFP intensity for neurons in FIG. 2E. Black line, line fit from linear regression. FIG. 2G is a box plot of the number of soma-localized XRIs per neuron versus cytosolic GFP intensity for neurons in FIG. 2E. Middle line in box plot, median; box boundary, interquartile range; whiskers, 10-90 percentile. n.s., not significant; *, $P<0.001$; Kruskal-Wallis analysis of variance followed by post-hoc Dunn's test. FIG. 2H shows length and FIG. 2I shows width of XRI versus time after AAV transduction (n=14 XRIs from 8 neurons from 1 culture; length and width were normalized to the maximum values over time, respectively). Thick centerline, mean; shaded boundary, standard deviation; thin lines, data from individual XRIs. FIG. 2J shows a representative maximum intensity projection confocal image of CA1 neurons in the AAV-injected region of mice injected with AAV9-UBC—XRI-HA at CA1, allowed for expression for 14 days, and then fixed, sliced, and stained against NeuN for soma of neurons and against HA for XRI. Scale bar, 20 μm. FIG. 2K provides a histogram of the number of soma-localized XRIs per neuron in the field of view described in FIG. 2J, among NeuN-positive cells (n=516 neurons from 1 field of view from 1 mouse). ‘96%’ with an arrow, 96% of the neurons had soma-localized XRI(s). FIG. 2**L provides a representative confocal image of U2OS cells expressing XRI-HA for 4 days, taken after fixation, Nissl staining, and immunostaining against HA for XRI. Scale bar, 20 μm.

FIG. 3A-E provides boxplots of the electrophysiological properties of cultured neurons with and without XRI expression, in terms of (FIG. 3A) resting potential, (FIG. 3B) membrane capacitance, (FIG. 3C) membrane resistance, (FIG. 3D) holding current while held at −65 mV, and (FIG. 3E) action potential amplitude. Cultured mouse hippocampal neurons (the ‘XRI’ group) were transduced with AAV9-UBC-mEGFP-P2A-XRI-HA as described in FIG. 1H on day in vitro 7 (DIV 7) for electrophysiological characterization via whole-cell patch clamp on DIV 14-16 side-by-side with neurons without AAV transduction (the 'Negative' group). Neurons with XRIs were identified by fluorescence imaging in the GFP channel before whole-cell patch clamp. n=11 neurons from 3 cultures for the Negative group; n=14 neurons from 4 cultures for the XRI group; n.s., not significant; Wilcoxon rank sum test. FIG. 3F-H shows results of differential expression analysis across mouse genes via RNA-Seq, comparing neuron cultures expressing GFP via AAV transduction (the 'GFP' group; n=14 neuron cultures) with neuron cultures without AAV transduction (the 'Neg' group; n=17 neuron cultures) as the baseline group (FIG. 3F), neuron cultures expressing XRI via AAV transduction (the 'XRI' group; n=24 neuron cultures) with the 'Neg' group as the baseline group (FIG. 3G), or the 'XRI' group with the 'GFP' group as the baseline group (FIG. 3H). Results plotted as scatter plots (one dot for one gene) in FIG. 3F-H of the fold change over the baseline group of the transcript count on a logarithmic scale to base 2 (log 2FoldChange) versus the P-value for the null hypothesis is that there is no differential expression across the two groups plotted in the format of −log 10(P-value), using Wald test with Benjamini-Hochberg correction. Mouse hippocampal neuron cultures were randomly split into the 'Neg' group, the 'GFP' group transduced with AAV9-UBC-GFP on day in vitro 7 (DIV 7), and the 'XRI' group transduced with AAV9-UBC—XRI-HA on DIV 7. On DIV 14, RNA was extracted from individual neuron cultures and then cDNA was generated from RNA and sequenced on an Illumina MiSeq. Sequences were mapped to the GRCm38 (mm10) reference genome (with gene annotations obtained from Ensembl) and gene expression raw counts were normalized and batch-effect adjusted using DESeq2 [Love, M. I., et al., *Genome Biol.* 15, 1-21 (2014)], followed by differential expression analysis and statistics using DESeq2.

FIG. 4A provides representative confocal images of brain slices from adult mice expressing GFP (or XRI) at CA1 region in the left (or right) cerebral hemisphere following AAV injection. 3-month-old mice were injected with AAV9-GFP at the CA1 region in the hippocampus of the left cerebral hemisphere and injected with AAV9-XRI-HA at the CA1 region in the hippocampus of the right cerebral hemisphere. When the mice reached 14 days after AAV injection, they were euthanized, perfused with 4% PFA, and brains were sliced coronally at 50 m in 1×PBS, and stained with antibodies against one of the cellular and synaptic markers below (see FIG. 4B-I) and against HA tag to label XRIs, together with DAPI to label nuclei. Staining intensities of cellular and synaptic markers in the cortex (or CA1) were imaged volumetrically using a 40× objective on a spinning disk confocal microscope, with identical imaging conditions, measured in ImageJ as the averaged fluorescent intensities of the fluorescent secondary antibodies over imaged fields of view (333 μm×333 μm×50 μm for each fields of view), and compared between the left hemisphere and the right hemisphere. FIG. 4B-I, top, provides representative confocal images of cortex and CA1 in the GFP-injected hemisphere and XRI-injected hemisphere in the brain slices stained with antibodies against each of the cellular and synaptic markers indicated, and DAPI. Scale bars, 100 μm. FIG. 4B-I, bottom) shows box plots of the staining intensities for each of the cellular and synaptic markers between the GFP-injected hemisphere and XRI-injected hemisphere; for each marker in each hemisphere, n=10 fields of view (FOVs) from 5 mice (2 FOVs for the GFP-injected hemisphere and 2 FOVs for the XRI-injected hemisphere per mouse). Middle line in box plot, median; box boundary, interquartile range; whiskers, 10-90 percentile. n.s., not significant; Wilcoxon rank sum test. (FIG. 4B) NeuN (a neuronal marker). (FIG. 4C) Cleaved Caspase-3 (an apoptotic marker). (FIG. 4D) GFAP (an astrocyte marker). (FIG. 4E) Ibal (a microglial marker). (FIG. 4F) Synaptophysin (a synaptic protein marker). (FIG. 4G) γH2AX (a DNA damage marker). (FIG. 4H-I) Hsp70 and Hsp27 (cell physiological stress markers).

FIG. 5A-C provides schematics of the constructs co-transduced into neurons (FIG. 5A), experiment pipeline (FIG. 5B), and expected epitope distribution along the XRI protein self-assembly (FIG. 5C) in the chemically induced gene expression experiment. XRI-HA, XRI with the epitope tag HA; XRI-FLAG, XRI with the epitope tag FLAG. The constructs were delivered to cells on day 0 via adeno-associated virus (AAV) transduction, and fixed 7 days later ($T_{fixation}$=7 days). $T_{4\text{-}OHT}$, time of 4-OHT treatment (once only per group of neurons); $T_{start}$, the time when XRI starts recording information after gene delivery and expression of XRI (see FIG. 4B, where $T_{start}$ is measured to be 3 days after AAV transduction). FIG. 5D shows representative confocal images of cultured mouse hippocampal neurons expressing constructs in FIG. 5A, taken after fixation, Nissl staining, and immunostaining against HA and FLAG tags. Three rows of rectangular panels at the bottom, enlarged views of regions marked in orange rectangles in the top row of square panels. Scale bar, 5 μm. FIG. 5E a4re graphs showing HA intensity profile along the XRI (top row), FLAG intensity profile along the XRI (middle row), and recovered FLAG signal (by averaging the two FLAG intensity profiles from the two halves of the XRIs) plotted against the fraction of the line integral of HA intensity (a value between 0 and 1; 0 corresponds to the center of the XRI, and 1 corresponds to the end of the XRI; bottom row), from the experiment described in FIG. 5A-C (n=21 XRIs from 13 neurons from 2 cultures for '1 d 4-OHT' group; n=37 XRIs from 19 neurons from 2 cultures for '2d 4-OHT' group; n =32 XRIs from 22 neurons from 2 cultures for '3d 4-OHT' group; n=38 XRIs from 22 neurons from 2 cultures for '4d 4-OHT' group; n=47 XRIs from 32 neurons from 2 cultures for '5d 4-OHT' group; n=29 XRIs from 19 neurons from 2 cultures for '6d 4-OHT' group; n =9 XRIs from 4 neurons from 1 culture for 'No 4-OHT' group). Each raw trace was normalized to its peak to show relative changes before averaging; see FIG. 4A for HA intensity profile, FLAG intensity profile, and recovered FLAG signal before normalization. Thick centerline, mean; darker boundary in the close vicinity of the thick centerline, standard error of mean; lighter boundary, standard deviation; lighter thin lines, data from individual XRIs; darker thin line, data from the corresponding XRI in the orange rectangle in FIG. 5D. See FIG. 3 for the detailed process flow of extracting signals from XRI assemblies. FIG. 5F shows a box plot of the ratio of the FLAG signal at the end of XRI to the FLAG signal at the center of XRI. Middle line in box plot, median; box boundary, interquartile range; whiskers, 10-90 percentile. n.s., not significant; , P<0.01; *, P<0.001; Kruskal-Wallis analysis of variance followed by post-hoc Dunn's test with 'No 4-OHT' as control group. FIG. 5G provides an example line plot of the FLAG signal plotted against the fraction of line integral of HA intensity (from the '5d 4-OHT' group in FIG. 5E), showing the quantification of the fraction of line integral of HA intensity when FLAG signal begins to rise (dot). Horizontal dashed line, the FLAG signal at the center of XRI (as baseline); angled dashed line, a line fitted to the initial rising phase of the FLAG signal (defined as the portion of FLAG signal between 10% to 50% of the peak FLAG signal); dot, intersection of the two dashed lines. FIG. 5H is plot of fraction of line integral of HA intensity when FLAG signal begins to rise plotted against the time of 4-OHT treatment after gene delivery, for XRIs in FIG. 5G. The line integral of HA intensity was normalized to '1' for day 7, the time of cell fixation and thus the end of XRI growth. Middle line in box plot, median; box boundary, interquartile range; whiskers, 10-90th percentile; black dot, mean; black line, linear interpolation of the means. *, P<0.05; , P<0.01; *, P<0.001; Kruskal-Wallis analysis of variance followed by post-hoc Dunn's test.

FIG. 6A are plots showing absolute HA intensity profile along the XRI (top row), absolute FLAG intensity profile along the XRI (middle row), and absolute recovered FLAG signal (by averaging the two FLAG intensity profiles from the two halves of the XRIs) plotted against the fraction of the line integral of HA intensity (a value between 0 and 1; 0 corresponds to the center of the XRI, and 1 corresponds to the end of the XRI; bottom row), from the experiment described in FIG. 5A-C (n=21 XRIs from 13 neurons from 2 cultures for '1d 4-OHT' group; n=37 XRIs from 19 neurons from 2 cultures for '2d 4-OHT' group; n =32 XRIs from 22 neurons from 2 cultures for '3d 4-OHT' group; n=38 XRIs from 22 neurons from 2 cultures for '4d 4-OHT' group; n=47 XRIs from 32 neurons from 2 cultures for '5d 4-OHT' group; n=29 XRIs from 19 neurons from 2 cultures for '6d 4-OHT' group; n =9 XRIs from 4 neurons from 1 culture for 'No 4-OHT' group). Thick centerline, mean; darker boundary in the close vicinity of the thick centerline, standard error of mean; lighter boundary, standard deviation; lighter thin lines, data from individual XRIs. FIG. 6B are plots showing baseline subtracted FLAG signal plotted against the fraction of the line integral of HA intensity for the '3d 4-OHT', '4d 4-OHT', '5d 4-OHT', '6d 4-OHT' groups in FIG. 5E. Thick centerline, mean; darker boundary in the close vicinity of the thick centerline, standard error of mean; lighter boundary, standard deviation. FIG. 6C provides scatter plots of the fraction of the line integral of HA intensity when the FLAG signal begins to rise versus the length of the XRI, the thickness of the XRI, the curvature of the XRI, and the ratio of the FLAG signal at the end to the FLAG signal at the center, for XRIs in neurons in the '5d 4-OHT' group in FIG. 5 (the '5d 4-OHT' group was randomly chosen for this analysis; n=47 XRIs from 32 neurons from 2 cultures). Gray line, line fit from linear regression. FIG. 6D provides scatter plot of the thickness of XRI versus the length of XRI, the curvature of XRI versus the length of XRI, and the curvature of XRI versus the thickness of XRI, for XRIs in FIG. 6C. Gray line, line fit from linear regression.

FIG. 8A is a schematic of using expansion microscopy (ExM) to increase the spatial resolution of immunofluorescence imaging. FIG. 8B-D shows schematics of the constructs co-transduced to neurons (FIG. 8B), experiment pipeline (FIG. 8C), and expected epitope distribution along the XRI protein self-assembly (FIG. 8D) in the chemically induced gene expression experiment, as in FIG. 5. FIG. 8E provides representative confocal images of XRIs in cultured mouse hippocampal neurons expressing constructs in FIG. 8B with different times of 4-OHT treatment ($T_{4\text{-}OHT}$), after 5×ExM. Scale bars, 5 μm after ExM (equivalent to 1 μm in biological units, e.g. when divided by the expansion factor). FIG. 8F provides plots showing HA intensity profile along the XRI (top row), FLAG intensity profile along the XRI (middle row), and recovered FLAG signal (by averaging the two FLAG intensity profiles across the two halves of XRI), plotted against the fraction of the line integral of HA intensity (a value between 0 and 1; 0 corresponds to the center of XRI, and 1 corresponds to the end of XRI; bottom row), from the experiment described in FIG. 8A-D (n=32 XRIs from 19 neurons from 2 cultures for '1 d 4-OHT' group; n=30 XRIs from 16 neurons from 2 cultures for '2d 4-OHT' group; n=23 XRIs from 14 neurons from 2 cultures for '3d 4-OHT' group; n =24 XRIs from 15 neurons from 3 cultures for '4d 4-OHT' group; n=22 XRIs from 17 neurons from 3 cultures for '5d 4-OHT' group; n=19 XRIs from 15 neurons from 3 cultures for '6d 4-OHT' group; n=7 XRIs from 3 neurons from 1 culture for 'No 4-OHT' group). Each raw trace was normalized to its peak, to show relative changes, before averaging. Thick centerline, mean; darker boundary in the close vicinity of the thick centerline, standard error of mean; lighter boundary, standard deviation; lighter thin lines, data from individual XRIs; darker thin line, data from the corresponding XRI in FIG. 8E. See FIG. 7 for the detailed process flow of extracting signals from XRI assemblies. FIG. 8G shows plots of baseline subtracted FLAG signal plotted against the fraction of the line integral of HA intensity for the '3d 4-OHT', '4d 4-OHT', '5d 4-OHT', '6d 4-OHT' groups in FIG. 8F. Thick centerline, mean; darker boundary in the close vicinity of the thick centerline, standard error of mean; lighter boundary, standard deviation. FIG. 8H is a plot showing fraction of line integral of HA intensity when FLAG signal begins to rise, plotted against the time of 4-OHT treatment after gene delivery, for XRIs in FIG. 8G. The line integral of HA intensity was normalized to '1' for day 7, the time of cell fixation and thus the end of XRI growth. Middle line in box plot, median; box boundary, interquartile range; whiskers, 10-90 percentile; black dot, mean; black line, linear interpolation of the means. *, $P<0.05$; Kruskal-Wallis analysis of variance followed by post-hoc Dunn's test. FIG. 8I is a bar plot of the absolute difference between the actual time and the inferred time of 4-OHT treatment, without and with 5×ExM. For each XRI, the inferred time of 4-OHT treatment was calculated from the fraction of the line integral of HA intensity when the FLAG signal begins to rise, using the black line in FIG. 5H (for XRI without ExM) or the black line in FIG. 8H (for XRI with 5×ExM) as time calibration. Bar height, mean; error bars, standard error of mean. n.s., not significant; Bonferroni corrected Wilcoxon rank sum tests.

FIG. 9A-C provide schematics of the AAV constructs co-transduced to neurons (FIG. 9A), experiment pipeline (FIG. 9B), and expected epitope distribution along the XRI protein self-assembly (FIG. 9C) in the c-fos promoter-driven gene expression experiment. XRI-HA, XRI with the epitope tag HA; XRI-V5, XRI with the epitope tag V5; c-fos, c-fos promoter; Tstim, the time of the onset of stimulation of neuron activity by KCl; $T_{start}$, the time when XRI starts recording information after gene delivery and expression of XRI, which is measured to be 3 days after AAV transduction in FIG. 5. FIG. 9D shows representative confocal images of cultured mouse hippocampal neurons expressing constructs in FIG. 9A, taken after fixation, Nissl staining, and immunostaining against HA and V5 tags. KCl stim, 55 mM KCl stimulation for 3 hours starting at $T_{stim}$=5 days; three rows of rectangular panels at the bottom, enlarged views of regions marked in orange rectangles in the top row of square panels. Scale bar, 5 μm throughout this figure. FIG. 9E provides blots showing HA intensity profile along the XRI (first row), V5 intensity profile along the XRI (second row), recovered V5 signal (by averaging the two V5 intensity profiles across the two halves of the XRI) plotted against the fraction of the line integral of HA intensity (third row), V5 signal relative change from baseline (ratio of the V5 signal to the V5 signal at the center of the XRI) plotted against the fraction of the line integral of HA intensity (fourth row), and V5 signal relative change from baseline plotted against recovered time after AAV transduction (using the black line in FIG. 5H as time calibration for time recovery from the line integral of HA intensity; fifth row), from the experiment described in FIG. 9A-C (n=30 XRIs from 28 neurons from 2 cultures for 'No Stim' group; n=40 XRIs from 22 neurons from 3 cultures for 'KCl Stim' group). Thick centerline, mean; darker boundary in the close vicinity of the thick centerline, standard error of mean; lighter boundary, standard deviation; lighter thin lines, data from individual XRIs; darker thin line, data from the corresponding XRI in the orange rectangle in FIG. 9D. In the first three rows, each raw trace was normalized to its peak to show relative changes before averaging. See FIG. 3 for the detailed process flow of extracting signals from XRI assemblies. FIG. 9F is a graph of V5 signal relative change from baseline plotted against recovered time after AAV transduction from XRIs in neurons under different KCl stimulations at $T_{stim}$=5 days (black arrow, onset of KCl stimulation; n=22 neurons from 3 cultures for '55 mM KCl 3 h' group; n=14 neurons from 4 cultures for '55 mM KCl 1 h' group; n=15 neurons from 2 cultures for '55 mM KCl 30 min' group; n=7 neurons from 1 culture for '55 mM KCl 10 min' group; n=9 neurons from 1 culture for '20 mM KCl 1 h' group; n=28 neurons from 2 cultures for 'No Stim' group;). Centerline, mean; shaded boundary, standard error of mean. FIG. 9G-I are box plots of the average V5 signal relative change from baseline over time between day 5 and day 7 (i.e., within 48 hours after the onset time of KCl stimulation) (FIG. 9G); the peak V5 signal relative change from baseline over time between day 5 and day 7 (FIG. 9H); and the slope of V5 signal relative change over time from baseline between day 5 and day 6 (FIG. 9I) for neurons in FIG. 9F. Middle line in box plot, median; box boundary, interquartile range; whiskers, 10-90 percentile; black dots, data points from individual neurons. *, $P<0.05$; , $P<0.01$; *, $P<0.001$; Kruskal-Wallis analysis of variance followed by post-hoc Dunn's tests between every two groups; test result was not significant for a pair without *, , or * indicated. FIG. 9J provides a representative confocal image of XRIs in a cultured mouse hippocampal neuron expressing constructs in FIG. 9A, taken after fixation (7 days after AAV transduction), Nissl staining, and immunostaining against HA and V5 tags. Neurons were stimulated twice, first at $T_{stim}$=5 days and then at $T_{stim}$=6 days, each time by 55 mM KCl for 1 hour. FIG. 9K is a graph showing V5 signal relative change from baseline plotted against recovered time after AAV transduction for the XRIs shown in FIG. 9J. Thin lines, traces from individual XRIs; thick line, the averaged trace over all XRIs. FIG. 9L is a graph showing V5 signal relative change from baseline plotted against recovered time after AAV transduction for XRIs in neurons under two sequential KCl stimulations as described in FIG. 9J (n=16 neurons from 2 cultures). Thick centerline, mean; darker boundary in the close vicinity of the thick centerline, standard error of mean; lighter boundary, standard deviation. **, P<0.01; Kruskal-Wallis analysis of variance followed by post-hoc Dunn's tests between the peak V5 signal relative change during T=5-6 (or 6-7) days after AAV transduction and the baseline V5 signal relative change (i.e., the V5 signal relative change averaged over T=3-5 days after AAV transduction).

FIG. 10A provides a construct schematic of GFP under c-fos promoter and representative confocal images of live cultured mouse hippocampal neurons in the GFP channel 1-7 days (1 d-7 d) after AAV transduction, without (upper row) and with (lower row) 55 mM KCl stimulation for 3 hours on 5 d. All images were captured under the same imaging condition. Scale bar, 10 μm. FIG. 10B is graph showing GFP fluorescence at soma (normalized by the average GFP fluorescence at soma over days 1-5) versus time (n=11 neurons from 2 cultures for 'No Stim' group; n=12 neurons from 2 cultures for 'KCl Stim' group). n.s., not significant; , P <0.01; Wilcoxon rank sum tests with Holm-Sidak correction between 'No Stim' and 'KCl Stim' on day 6 or day 7 after AAV transduction. FIG. 10C-D at top provide confocal images of XRIs (as examples in addition to FIG. 9A) in two cultured mouse hippocampal neurons expressing constructs in FIG. 9**A, taken after fixation (7 days after AAV transduction), Nissl staining, and immunostaining against HA and V5 tags; bottom, V5 signal relative change from baseline plotted against recovered time after AAV transduction for the corresponding XRI. Scale bars, 5 μm. Neurons were stimulated twice, first at $T_{stim}$=5 days and then at $T_{stim}$=6 days, each time by 55 mM KCl for 1 hour.

FIG. 11A-B are schematics of the AAV constructs (FIG. 11A, left), expected epitope distribution along the XRI protein self-assembly (FIG. 11A, right), and experiment pipeline (FIG. 11B) in this XRI self-assembly experiment in mouse brain. AAVs were injected into the dorsal CA1 area of the brains of 3-month-old mice on day 0, followed by 4-OHT intraperitoneal (i.p.) injection on day 10 and then fixation via 4% paraformaldehyde perfusion on day 14. The preserved brains were then sectioned at 50 μm coronally and stained with anti-HA, anti-FLAG, and Nissl stain. FIG. 11C provides confocal images of a representative brain section from the experiment described in FIG. 11B: square in the left panel, boundary of the region of interest enlarged in the right panel; square in the right panel, boundary of the region of interest enlarged in FIG. 11D lines and numbers in the right panel, locations of the neurons shown in FIG. 11E; scale bars, 500 μm. FIG. 11D is image showing maximum intensity projection (MIP) of a 4.4-μm-thick volume in the region of interest indicated in the square in the right panel in FIG. 11C. Some of the XRIs are not completely contained within the volume for this MIP in the Z (depth) dimension and therefore are not fully shown in these 2D images. Scale bar, 20 μm. FIG. 11E provides confocal images of representative CA1 neurons indicated in the right panel in FIG. 11C. FIG. 11F is graph showing FLAG signal minus the FLAG signal at the center averaged and plotted against the fraction of the line integral of HA intensity along the XRI. n=893 XRIs from 835 CA1 neurons from 1 brain section (the one shown in FIG. 11C) from 1 mouse with 4-OHT i.p. injection on day 10 (shown in upper shaded region) and n=598 XRIs from 475 CA1 neurons from 1 brain section from 1 mouse without 4-OHT i.p. injection (shown in black). The line integral of HA intensity was defined as '1' for day 14, the time of fixation and thus the end of XRI growth. Colored lines, median; colored, shaded boundaries, interquartile range; lighter thin lines, data from individual XRIs. ***, P<0.001; Wilcoxon rank sum test.

BRIEF DESCRIPTION OF CERTAIN OF THE SEQUENCES

Figure 1A:
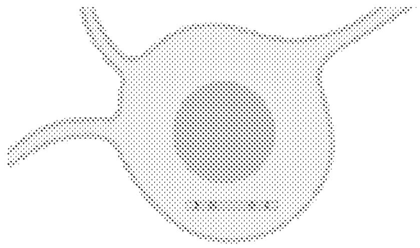
FIG. 1A-J provides schematic diagrams, graphs, and photomicrographs illustrating concept and development of linear protein-based cellular physiology recording devices.
Figure 1B:
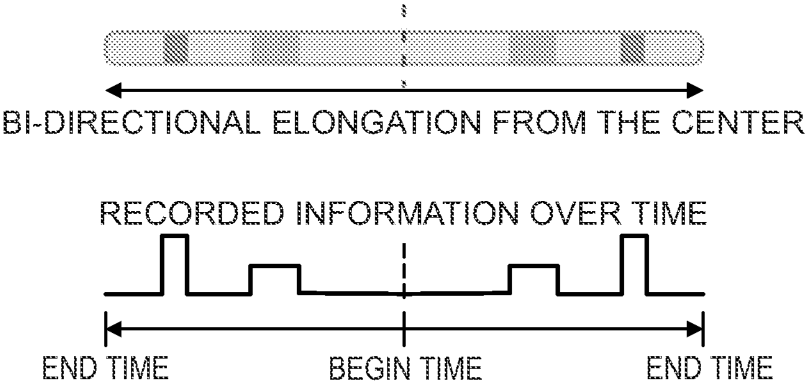

Table 1 provides a list of protein motifs used in certain embodiments of expression-recording island (XRI) compositions and methods set forth herein. For the motifs in Table 1, the protein sequences were mouse codon optimized into DNA sequences and then synthesized before experimenst using routine methods of protein engineering. The amino acid sequences fully determine the proteins' structures and functions. Based on the amino acid sequence information disclosed herein, it will be understood that routine methods can be used to determine and prepare DNA sequences that encode proteins such as motifs, spacers, detectable tags, self-assembling filament-forming monomers, and other proteins of the invention.

TABLE 1

Sequences of protein motifs used in certain studies disclosed herein

| Motif name | Amino acid sequence | Ref | SEQ ID NO |
|---|---|---|---|
| 1POK (E239Y) | MIDYTAAGFTLLQGAHLYAPEDRGICDV LVANGKIIAVASNIPSDIVPNCTVVDLSGQ ILCPGFIDQHVHLIGGGGEAGPTTRTPEV ALSRLTEAGVTSVVGLLGTDSISRHPESL LAKTRALNEEGISAWMLTGAYHVPSRTI TGSVEKDVAIIDRVIGVKCAISDHRSAAP DVYHLANMAAESRVGGLLGGKPGVTVF HMGDSKKALQPIYDLLENCDVPISKLLPT HVNRNVPLFYQALEFARKGGTIDITSSIDE PVAPAEGIARAVQAGIPLARVTLSSDGNG | Garcia-Seisdedos, H., et al. Nature 548, 244 (2017) | 1 |

TABLE 1-continued

Sequences of protein motifs used in certain studies disclosed herein

| Motif name | Amino acid sequence | Ref | SEQ ID NO |
|---|---|---|---|
| | SQPFFDDEGNLTHIGVAGFETLLETVQVL<br>VKDYDFSISDALRPLTSSVAGFLNLIGKG<br>EILPGNDADLLVMTPELRIEQVYARGKL<br>MVKDGKACVKGTFETA | | |
| Maltose binding protein (MBP tag) | KIEEGKLVIWINGDKGYNGLAEVGKKFE<br>KDTGIKVTVEHPDKLEEKFPQVAATGDG<br>PDIIFWAHDRFGGYAQSGLLAEITPDKAF<br>QDKLYPFTWDAVRYNGKLIAYPIAVEAL<br>SLIYNKDLLPNPPKTWEEIPALDKELKAK<br>GKSALMFNLQEPYFTWPLIAADGGYAFK<br>YENGKYDIKDVGVDNAGAKAGLTFLVD<br>LIKNKHMNADTDYSIAEAAFNKGETAMT<br>INGPWAWSNIDTSKVNYGVTVLPTFKGQ<br>PSKPFVGVLSAGINAASPNKELAKEFLEN<br>YLLTDEGLEAVNKDKPLGAVALKSYEEE<br>LAKDPRIAATMENAQKGEIMPNIPQMSA<br>FWYAVRTAVINAASGRQTVDEALKDAQ<br>T | Kapust, R. B. & Waugh, D. S. Protein Sci. 8, 1668-1674 (1999) | 2 |
| HA (HA tag) | YPYDVPDYA | | 3 |
| FLAG (FLAG tag) | DYKDDDDK | | 4 |
| V5 (V5 tag) | GKPIPNPLLGLDST | | 5 |
| 1M3U (D157L, E158L, D161L) | MKPTTISLLQKYKOEKKRFATITAYDYSF<br>AKLFADEGLNVMLVGDSLGMTVQGHDS<br>TLPVTVADIAYHTAAVRRGAPNCLLLAD<br>LPEMAYATPEQAFENAATVMRAGANMV<br>KIEGGEWLVETVQMLTERAVPVCGHLGL<br>TPQSVNIFGGYKVQGRGLLAGLQLLSDA<br>LALEAAGAQLLVLECVPVELAKRITEAL<br>AIPVIGIGAGNVTDGQILVMHDAFGITGG<br>HIPKFAKNFLAETGDIRAAVROYMAEVE<br>SGVYPGEEHSFH | Garcia-Seisdedos, H., et al. Nature 548, 244 (2017) | 6 |
| 2CG4 (K126Y, D131Y) | MENYLIDNLDRGILEALMGNARTAYAEL<br>AKQFGVSPETIHVRVEKMKQAGIITGARI<br>DVSPKQLGYDVGCFIGIILKSAKDYPSAL<br>AKLESLDEVTEAYYTTGHYSIFIKVMCRS<br>IDALQHVLINYIQTIYEIQSTETLIVLQNPI<br>MRTIKP | Garcia-Seisdedos, H., et al. Nature 548, 244 (2017) | 7 |
| 2VYC (K491L, D494L, D497L) | MKVLIVESEFLHODTWVGNAVERLADA<br>LSQQNVTVIKSTSFDDGFAILSSNEAIDCL<br>MFSYQMEHPDEHONVRQLIGKLHERQQ<br>NVPVFLLGDREKALAAMDRDLLELVDEF<br>AWILEDTADFIAGRAVAAMTRYRQQLLP<br>PLFSALMKYSDIHEYSWAAPGHQGGVGF<br>TKTPAGRFYHDYYGENLFRTDMGIERTS<br>LGSLLDHTGAFGESEKYAARVFGADRSW<br>SVVVGTSGSNRTIMQACMTDNDVVVVD<br>RNCHKSIEQGLMLTGAKPVYMVPSRNRY<br>GIIGPIYPQEMQPETLOKKISESPLIKDKA<br>GQKPSYCVVTNCTYDGVCYNAKEAQDL<br>LEKTSDRLHFDEAWYGYARFNPIYADHY<br>AMRGEPGDHNGPTVFATHSTHKLLNALS<br>QASYIHVREGRGAINFSRFNQAYMMHAT<br>TSPLYAICASNDVAVSMMDGNSGLSLTQ<br>EVIDEAVDFRQAMARLYKEFTADGSWFF<br>KPWNKEVVTDPQTGLTYLFALAPTKLLT<br>TVQDCWVMHPGESWHGFKDIPDNWSML<br>DPIKVSILAPGMGEDGELEETGVPAALVT<br>AWLGRHGIVPTRTTDFQIMFLFSMGVTR<br>GKWGTLVNTLCSFKRHYDANTPLAQVM<br>PELVEQYPDTYANMGIHDLGDTMFAWL<br>KENNPGARLNEAYSGLPVAEVTPREAYN<br>AIVDNNVELVSIENLPGRIAANSVIPYPPG<br>IPMLLSGENFGDKNSPQVSYLRSLQSWD<br>HHFPGFEHETEGTEIIDGIYHVMCVKA | Garcia-Seisdedos, H., et al. Nature 548, 244 (2017) | 8 |

TABLE 1-continued

Sequences of protein motifs used in certain studies disclosed herein

| Motif name | Amino acid sequence | Ref | SEQ ID NO |
|---|---|---|---|
| DHF40 | MSSEKEELRERLVKICVELAKLKGDDTL KAAEAAEEAFRLVVLAAMLAGIDSSEVL ELAIRLIKTCVVLAAMEGYDISEACRAAA EAFTRVAMAALRAGITSSLVLKAAIELIK ECVLNAAVEGYDISEACRAAAEAFKRVA EAAKRAGITSLETLLRATEEIRKRVEEAQR EGNDISEACRQAAFEFRKKAEELKRRGD V | Shen, H. et al. Science 362, 705 (2018) | 9 |
| γPFD | MVNEVIDINEAVRAYTAQIEGLRAEIGRL DATIATLRQSLATLKSLKTLGEGKTVLVP VGSIAQVEMKVEKMDKVVVSVGQNISA ELEYEEALKYIEDEIKKLLTFRLVLEQAIA ELYAKIEDLIAEAQQTSEEEKAEEEENEE KAE | Glover, D. J., et al., Nat. Commun. 2016 717,1-9 (2016) | 10 |
| Top7 | DIQVQVNIDDNGKNFDYTYTVTTESELQ KVLNELKDYIKKQGAKRVRISITARTKKE AEKFAAILIKVFAELGYNDINVTWDGDT VTVEGQLE | Kuhlman, B.. et al. Science 302, 1364-1368 (2003) | 11 |
| dTor_ 12x31L | GSSMASGISVEELLKLAKAAYYSGTTVEE AYKLALKLGISVEELLKLAEAAYYSGTT VEEAYKLALKLGISVEELLKLAKAAYYS GTTVEEAYKLALKLGISVEELLKLAKAA YYSGTTVEEAYKLALKLGISVEELLKLAE AAYYSGTTVEEAYKLALKLGISVEELLKL AKAAYYSGTTVEEAYKLALKLGISVEEL LKLAKAAYYSGTTVEEAYKLALKLGISV EELLKLAEAAYYSGTTVEEAYKLALKLG ISVEELLKLAKAAYYSGTTVEEAYKLAL KLGISVEELLKLAKAAYYSGTTVEEAYK LALKLGISVEELLKLAEAAYYSGTTVEEA YKLALKLGISVEELLKLAKAAYYSGTTV EEAYKLALKLG | Doyle, L. et al.Nature 528, 585-588 (2015) | 12 |
| ERT2-iCre- ERT2 | MAGDMRAANLWPSPLMIKRSKKNSLAL SLTADQMVSALLDAEPPILYSEYDPTRPF SEASMMGLLTNLADRELVHMINWAKRV PGFVDLTLHDQVHLLECAWLEILMIGLV WRSMEHPVKLLFAPNLLLDRNQGKCVE GMVEIFDMLLATSSRFRMMNLQGEEFVC LKSTILLNSGVYTFLSSTLKSLEEKDHIHR VLDKITDILIHLMAKAGLTLQQQHQRLA QLLLILSHIRHMSNKGMEHLYSMKCKNV VPLYDLLLEAADAHRLHAPTSRGGASVE ETDQSHLATAGSTSSHSLQKYYITGEAEG FPATAVDNLLTVHQNLPALPVDATSDEV RKNLMDMFRDRQAFSEHTWKMLLSVCR SWAAWCKLNNRKWFPAEPEDVRDYLLY LQARGLAVKTIQQHLGQLNMLHRRSGLP RPSDSNAVSLVMRRIRKENVDAGERAKQ ALAFERTDFDQVRSLMENSDRCQDIRNL AFLGIAYNTLLRIAEIARIRVKDISRTDGG RMLIHIGRTKTLVSTAGVEKALSLGVTKL VERWISVSGVADDPNNYLFCRVRKNGV AAPSATSQLSTRALEGIFEATHRLIYGAK DDSGQRYLAWSGHSARVGAARDMARA GVSIPEIMQAGGWTNVNIVMNYIRNLDS ETGAMVRLLEDGDLEPSAGDMRAANLW PSPLMIKRSKKNSLALSLTADQMVSALLD AEPPILYSEYDPTRPFSEASMMGLLTNLA DRELVHMINWAKRVPGFVDLTLHDQVH LLECAWLEILMIGLVWRSMEHPVKLLFA PNLLLDRNQGKCVEGMVEIFDMLLATSS RFRMMNLQGEEFVCLKSIILLNSGVYTFL SSTLKSLEEKDHIHRVLDKITDTLIHLMA KAGLTLQQQHQRLAQLLLILSHIRHMSN KGMEHLYSMKCKNVVPLYDLLLEAADA HRLHAPTSRGGASVEETDQSHLATAGST SSHSLQKYYITGEAEGFPATA | Matsuda, T, and C.L. Cepko, Proc. Natl. Acad. Sci. U. S. A. 104, 1027-1032 (2007) | 13 |

TABLE 1-continued

Sequences of protein motifs used in certain studies disclosed herein

| Motif name | Amino acid sequence | Ref | SEQ ID NO |
|---|---|---|---|
| NLS (SV40 NLS) | PKKKRKV | | 14 |
| Linker2 | GG | | |
| Linker3 | GSG | | |
| Linker4 | GSGG | | 15 |
| Linkers | GGGSG | | 16 |
| Linker6 | GGSGGT | | 17 |
| Linker7 | GGSGGTG | | 18 |
| Linker8 | GGSGGTGG | | 19 |
| Linker12 | GGSGGTGGSGGT | | 20 |
| Linker13 | GGSGGTGGSGGTG | | 21 |
| Linker14 | GGSGGTGGSGGTGG | | 22 |
| Linker18 | GGSGGTGGSGGTGGSGGT | | 23 |
| Linker24 | GGSGGTGGSGGIGGSGGTGGSGGT | | 24 |
| Linker25 | GGSGGTGGSGGTGGSGGTGGSGGTG | | 25 |

SEQ ID NO: 26 is amino acid sequence of synthetic construct XRI-HA gene GenBank ® OK539810:
MIDYTAAGFTLLQGAHLYAPEDRGICDVLVANGKIIAVASNIPSDIVPNCTVVDLSGQ
ILCPGFIDQHVHLIGGGGEAGPTTRTPEVALSRLTEAGVTSVVGLLGTDSISRHPESLL
AKTRALNEEGISAWMLTGAYHVPSRTITGSVEKDVAIIDRVIGVKCAISDHRSAAPDV
YHLANMAAESRVGGLLGGKPGVTVFHMGDSKKALQPIYDLLENCDVPISKLLPTHV
NRNVPLFYQALEFARKGGTIDITSSIDEPVAPAEGIARAVQAGIPLARVTLSSDGNGSQ
PFFDDEGNLTHIGVAGFETLLETVQVLVKDYDFSISDALRPLTSSVAGFLNLTGKGEIL
PGNDADLLVMTPELRIEQVYARGKLMVKDGKACVKGTFETAGGSGGTGGSGGTGG
SGGTGGSGGTGYPYDVPDYAGSGKIEEGKLVIWINGDKGYNGLAEVGKKFEKDTGI
KVTVEHPDKLEEKFPQVAATGDGPDIIFWAHDRFGGYAQSGLLAEITPDKAFQDKLY
PFTWDAVRYNGKLIAYPIAVEALSLIYNKDLLPNPPKTWEEIPALDKELKAKGKSAL
MFNLQEPYFTWPLIAADGGYAFKYENGKYDIKDVGVDNAGAKAGLTFLVDLIKNK
HMNADTDYSIAEAAFNKGETAMTINGPWAWSNIDTSKVNYGVTVLPTFKGQPSKPF
VGVLSAGINAASPNKELAKEFLENYLLTDEGLEAVNKDKPLGAVALKSYEEELAKD
PRIAATMENAQKGEIMPNIPQMSAFWYAVRTAVINAASGRQTVDEALKDAQT.

SEQ ID NO: 27 is DNA sequence of synthetic construct XRI-HA gene GenBank ® OK539810:
atgattgactatactgctgctggtttcaccctcctccaaggtgcacatctgtacgctcctgaagacagaggtatctgcgatgtgctggttg
ccaacggtaagatcatcgctgtggcctccaacattcctagcgacatcgttccaaactgcaccgttgtcgatctgagcggacagatcctct
gtccaggattcattgatcagcacgtgcacctcattggaggaggaggcgaagctggtcctactactagaactcccgaagtcgcactgtct
cgcctcacagaggcaggcgttacctccgtcgtgggactcctgggtactgatagcatctctaggcaccctgagtctctgctggcaaaga
ccagagccctcaatgaggagggtatctccgcttggatgctgactggtgcttatcacgtcccatctcgcaccattactggcagcgtggag
aaggacgttgcaatcatcgacagagtgateggtgttaagtgcgctatctccgaccacaggagcgctgctcccgacgtctatcacctgg
ccaacatggcagccgagagcagagtcggtggtctgctcggtggcaagccaggagttaccgtgttccacatgggtgactctaagaag
gcactgcaacccatctatgacctgctggagaactgtgacgtcccaatctccaagctgctgcctacccacgtcaacaggaacgtgcctct
cttctaccaagctctggagttcgcaagaaagggtggcaccatcgacatcacctctagcattgatgaacccgtcgctccagctgaggga
atcgcaagggctgtccaagcaggtatcccactggcaagggtgacactcagctctgatggcaacggctcccagccattcttcgatgatg
aaggaaatctgactcacattggcgtggctggatttgaaactctcctggaaacagttcaggttctggttaaggactacgacttcagcatttct
gacgctctcagaccactcacctctagcgtcgctggcttcctgaacctgactggtaaaggcgaaatcctccctggtaatgacgctgatct
gctggtgatgacacccgaactgcgcattgagcaggtctatgcaagaggaaagctgatggttaaggacggaaaggcttgtgtcaaggg
cacattcgagactgctggtggctctggaggcaccggagggtctggagggactggaggctctggaggtactggcggttctggaggta
ccggttacccatacgatgtgcctgattacgcaggatccggtaagattgaagagggcaaactggttatctggatcaatggcgataaggg
ctacaatggcctggcagaggtcggtaagaagttcgagaaagatacaggcatcaaagttactgtggaacacccagataagctggagga
gaagttccctcaggtcgcagcaactggcgacggtccagacatcatcttctgggcacacgataggttcggtggctatgcccaatctggc
ctgctggctgagattactcctgataaggctttccaggacaagctgtatccattcacctgggatgctgtgagatacaatggcaagctgatc
gcataccctattgctgtggaagctctgagcctgatctacaacaaggacctgctgcctaatcctcctaagacatgggaagaaatccctgc
actggacaaggaactgaaggccaaaggcaagtccgcactgatgttcaacctgcaggagccttactttacctggccactgattgctgcc
gacggtggttacgctttcaagtacgagaatggtaagtacgacatcaaagatgtgggtgtggacaatgctggtgccaaagctggtctga -continued ctttcctggtggatctgatcaagaacaagcacatgaatgcagacactgactattctatcgcagaggctgctttcaacaaaggcgaaacc
gcaatgactatcaatggtccttgggcatggtctaacatcgacactagcaaagtcaactacggtgtcaccgttctgccaaccttcaagggt
cagccaagcaaacctttcgttggcgtgctgagcgcaggtatcaacgctgcctctcctaacaaagagctggctaaggagtttctggaga
actacctgctgacagacgaaggtctggaggcagtgaacaaggacaagccactgggtgccgtggctctgaagagctacgaagaaga
actggccaaggaccctcgcatcgctgctacaatggagaacgcacagaagggtgagatcatgccaaacatcccacagatgagcgcat
tctggtatgccgtgaggaccgctgttatcaacgcagcttctggcagacagaccgtggatgaagccctgaaagacgcacagacc.

SEQ ID NO: 28 is amino acid sequence of synthetic construct XRI-FLAG gene GenBank ® OK539811:
MIDYTAAGFTLLQGAHLYAPEDRGICDVLVANGKIIAVASNIPSDIVPNCTVVDLSGQ
ILCPGFIDQHVHLIGGGGEAGPTTRTPEVALSRLTEAGVTSVVGLLGTDSISRHPESLL
AKTRALNEEGISAWMLTGAYHVPSRTITGSVEKDVAIIDRVIGVKCAISDHRSAAPDV
YHLANMAAESRVGGLLGGKPGVTVFHMGDSKKALQPIYDLLENCDVPISKLLPTHV
NRNVPLFYQALEFARKGGTIDITSSIDEPVAPAEGIARAVQAGIPLARVTLSSDGNGSQ
PFFDDEGNLTHIGVAGFETLLETVQVLVKDYDFSISDALRPLTSSVAGFLNLTGKGEIL
PGNDADLLVMTPELRIEQVYARGKLMVKDGKACVKGTFETAGGSGGTGGSGGTGG
SGGTGGSGGTGDYKDDDDKGSGKIEEGKLVIWINGDKGYNGLAEVGKKFEKDTGIK
VTVEHPDKLEEKFPQVAATGDGPDIIFWAHDRFGGYAQSGLLAEITPDKAFQDKLYP
FTWDAVRYNGKLIAYPIAVEALSLIYNKDLLPNPPKTWEEIPALDKELKAKGKSALM
FNLQEPYFTWPLIAADGGYAFKYENGKYDIKDVGVDNAGAKAGLTFLVDLIKNKH
MNADTDYSIAEAAFNKGETAMTINGPWAWSNIDTSKVNYGVTVLPTFKGQPSKPFV
GVLSAGINAASPNKELAKEFLENYLLTDEGLEAVNKDKPLGAVALKSYEEELAKDPR
IAATMENAQKGEIMPNIPQMSAFWYAVRTAVINAASGRQTVDEALKDAQT.

SEQ ID NO: 29 is DNA sequence of synthetic construct XRI-FLAG gene GenBank® OK539811:
atgattgactatactgctgctggtttcaccctcctccaaggtgcacatctgtacgctcctgaagacagaggtatctgcgatgtgctggttg
ccaacggtaagatcatcgctgtggcctccaacattcctagcgacatcgttccaaactgcaccgttgtcgatctgagcggacagatcctct
gtccaggattcattgatcagcacgtgcacctcattggaggaggaggcgaagctggtcctactactagaactcccgaagtcgcactgtct
cgcctcacagaggcaggcgttacctccgtcgtgggactcctgggtactgatagcatctctaggcaccctgagtctctgctggcaaaga
ccagagccctcaatgaggagggtatctccgcttggatgctgactggtgcttatcacgtcccatctcgcaccattactggcagcgtggag
aaggacgttgcaatcatcgacagagtgatcggtgttaagtgcgctatctccgaccacaggagcgctgctcccgacgtctatcacctgg
ccaacatggcagccgagagcagagtcggtggtctgctcggtggcaagccaggagttaccgtgttccacatgggtgactctaagaag
gcactgcaacccatctatgacctgctggagaactgtgacgtcccaatctccaagctgctgcctacccacgtcaacaggaacgtgcctct
cttctaccaagctctggagttcgcaagaaagggtggcaccatcgacatcacctctagcattgatgaacccgtcgctccagctgaggga
atcgcaagggctgtccaagcaggtatcccactggcaagggtgacactcagctctgatggcaacggctcccagccattcttcgatgatg
aaggaaatctgactcacattggcgtggctggatttgaaactctcctggaaacagttcaggttctggttaaggactacgacttcagcatttct
gacgctctcagaccactcacctctagcgtcgctggcttcctgaacctgactggtaaaggcgaaatcctccctggtaatgacgctgatct
gctggtgatgacacccgaactgcgcattgagcaggtctatgcaagaggaaagctgatggttaaggacggaaaggcttgtgtcaaggg
cacattcgagactgctggtggctctggaggcaccggagggtctggagggactggaggctctggaggtactggcggttctggaggta
ccggtgactacaaggacgatgatgacaaaggatccggtaagattgaagagggcaaactggttatctggatcaatggcgataagggct
acaatggcctggcagaggtcggtaagaagttcgagaaagatacaggcatcaaagttactgtggaacacccagataagctggaggag
aagttccctcaggtcgcagcaactggcgacggtccagacatcatcttctgggcacacgataggttcggtggctatgcccaatctggcct
gctggctgagattactcctgataaggctttccaggacaagctgtatccattcacctgggatgctgtgagatacaatggcaagctgatcgc
ataccctattgctgtggaagctctgagcctgatctacaacaaggacctgctgcctaatcctcctaagacatgggaagaaatccctgcact
ggacaaggaactgaaggccaaaggcaagtccgcactgatgttcaacctgcaggagccttactttacctggccactgattgctgccgac
ggtggttacgctttcaagtacgagaatggtaagtacgacatcaaagatgtgggtgtggacaatgctggtgccaaagctggtctgactttc
ctggtggatctgatcaagaacaagcacatgaatgcagacactgactattctatcgcagaggctgctttcaacaaaggcgaaaccgcaa
tgactatcaatggtccttgggcatggtctaacatcgacactagcaaagtcaactacggtgtcaccgttctgccaaccttcaagggtcagc
caagcaaacctttcgttggcgtgctgagcgcaggtatcaacgctgcctctcctaacaaagagctggctaaggagtttctggagaactac
ctgctgacagacgaaggtctggaggcagtgaacaaggacaagccactgggtgccgtggctctgaagagctacgaagaagaactgg
ccaaggaccctcgcatcgctgctacaatggagaacgcacagaagggtgagatcatgccaaacatcccacagatgagcgcattctggt
atgccgtgaggaccgctgttatcaacgcagcttctggcagacagaccgtggatgaagccctgaaagacgcacagacc.

SEQ ID NO: 30 is amino acid sequence of synthetic construct XRI-V gene GenBank ® OK539812:
MIDYTAAGFTLLQGAHLYAPEDRGICDVLVANGKIIAVASNIPSDIVPNCTVVDLSGQ
ILCPGFIDQHVHLIGGGGEAGPTTRTPEVALSRLTEAGVTSVVGLLGTDSISRHPESLL
AKTRALNEEGISAWMLTGAYHVPSRTITGSVEKDVAIIDRVIGVKCAISDHRSAAPDV
YHLANMAAESRVGGLLGGKPGVTVFHMGDSKKALQPIYDLLENCDVPISKLLPTHV
NRNVPLFYQALEFARKGGTIDITSSIDEPVAPAEGIARAVQAGIPLARVTLSSDGNGSQ
PFFDDEGNLTHIGVAGFETLLETVQVLVKDYDFSISDALRPLTSSVAGFLNLTGKGEIL
PGNDADLLVMTPELRIEQVYARGKLMVKDGKACVKGTFETAGGSGGTGGSGGTGG
SGGTGGSGGTGGKPIPNPLLGLDSTGSGKIEEGKLVIWINGDKGYNGLAEVGKKFEK
DTGIKVTVEHPDKLEEKFPQVAATGDGPDIIFWAHDRFGGYAQSGLLAEITPDKAFQ
DKLYPFTWDAVRYNGKLIAYPIAVEALSLIYNKDLLPNPPKTWEEIPALDKELKAKG
KSALMFNLQEPYFTWPLIAADGGYAFKYENGKYDIKDVGVDNAGAKAGLTFLVDLI
KNKHMNADTDYSIAEAAFNKGETAMTINGPWAWSNIDTSKVNYGVTVLPTFKGQPS
KPFVGVLSAGINAASPNKELAKEFLENYLLTDEGLEAVNKDKPLGAVALKSYEEELA
KDPRIAATMENAQKGEIMPNIPQMSAFWYAVRTAVINAASGRQTVDEALKDAQT.

SEQ ID NO: 31 is DNA sequence of synthetic construct XRI-V gene GenBank ® OK539812:
atgattgactatactgctgctggtttcaccctcctccaaggtgcacatctgtacgctcctgaagacagaggtatctgcgatgtgctggttg
ccaacggtaagatcatcgctgtggcctccaacattcctagcgacatcgttccaaactgcaccgttgtcgatctgagcggacagatcctct
gtccaggattcattgatcagcacgtgcacctcattggaggaggaggcgaagctggtcctactactagaactcccgaagtcgcactgtct
cgcctcacagaggcaggcgttacctccgtcgtgggactcctgggtactgatagcatctctaggcaccctgagtctctgctggcaaaga
ccagagccctcaatgaggagggtatctccgcttggatgctgactggtgcttatcacgtcccatctcgcaccattactggcagcgtggag
aaggacgttgcaatcatcgacagagtgatcggtgttaagtgcgctatctccgaccacaggagcgctgctcccgacgtctatcacctgg
ccaacatggcagccgagagcagagtcggtggtctgctcggtggcaagccaggagttaccgtgttccacatgggtgactctaagaag -continued

```
gcactgcaacccatctatgacctgctggagaactgtgacgtcccaatctccaagctgctgcctacccacgtcaacaggaacgtgcctct
cttctaccaagctctggagttcgcaagaaagggtggcaccatcgacatcacctctagcattgatgaacccgtcgctccagctgaggga
atcgcaagggctgtccaagcaggtatcccactggcaagggtgacactcagctctgatggcaacggctcccagccattcttcgatgatg
aaggaaatctgactcacattggcgtggctggatttgaaactctcctggaaacagttcaggttctggttaaggactacgacttcagcatttct
gacgctctcagaccactcacctctagcgtcgctggcttcctgaacctgactggtaaaggcgaaatcctccctggtaatgacgctgatct
gctggtgatgacacccgaactgcgcattgagcaggtctatgcaagaggaaagctgatggttaaggacggaaaggcttgtgtcaaggg
cacattcgagactgctggtggctctggaggcaccggagggtctggagggactggaggctctggaggtactggcggttctggaggta
ccggtggtaagcctatccctaaccctctgctcggtctcgattctaccggatccggtaagattgaagagggcaaactggttatctggatca
atggcgataagggctacaatggcctggcagaggtcggtaagaagttcgagaaagatacaggcatcaaagttactgtggaacaccca
gataagctggaggagaagttccctcaggtcgcagcaactggcgacggtccagacatcatcttctgggcacacgataggttcggtggc
tatgcccaatctggcctgctggctgagattactcctgataaggctttccaggacaagctgtatccattcacctgggatgctgtgagataca
atggcaagctgatcgcatacccctattgctgtggaagctctgagcctgatctacaacaaggacctgctgcctaatcctcctaagacatgg
gaagaaatccctgcactggacaaggaactgaaggccaaaggcaagtccgcactgatgttcaacctgcaggagccttactttacctgg
ccactgattgctgccgacggtggttacgctttcaagtacgagaatggtaagtacgacatcaaagatgtgggtgtggacaatgctggtgc
caaagctggtctgactttcctggtggatctgatcaagaacaagcacatgaatgcagacactgactattctatcgcagaggctgctttcaa
caaaggcgaaaccgcaatgactatcaatggtccttgggcatggtctaacatcgacactagcaaagtcaactacggtgtcaccgttctgc
caaccttcaagggtcagccaagcaaacctttcgttggcgtgctgagcgcaggtatcaacgctgcctctcctaacaaagagctggctaa
ggagtttctggagaactacctgctgacagacgaaggtctggaggcagtgaacaaggacaagccactgggtgccgtggctctgaaga
gctacgaagaagaactggccaaggaccctcgcatcgctgctacaatggagaacgcacagaagggtgagatcatgccaaacatccca
cagatgagcgcattctggtatgccgtgaggaccgctgttatcaacgcagcttctggcagacagaccgtggatgaagccctgaaagac
gcacagacc.
```

DETAILED DESCRIPTION

Certain aspects of the invention can be used to record cellular physiological information onto intracellular, steadily growing, protein chains made out of fully genetically encoded self-assembling proteins, and then read out via routine immunofluorescence and imaging techniques. Compositions of the invention include certain existing, human-created self-assembling protein candidates, which have now been engineered to add a novel "insulator" component to the self-assembling protein candidate. Compositions of the invention comprise one or more sequences encoding self-assembling filament forming monomers, zero, one, or more of a detectable tag or tags, and zero, one or more protein spacers. A composition of the invention, when expressed in a cell produces an engineered protein capable of stable, time-ordered longitudinal growth in the cell. Embodiments of compositions of the invention include a sequence encoding an expression-recording island (XRI).

It has now been determined that an expression-recording island (XRI) strategy such as described herein, can be used for long-term recording of gene expression time course, with single-cell precision, across cell populations. Because the linear protein assembly grows continuously over time, it acts like a molecular tape recorder that preserves the temporal order of the protein monomers made available by the cell depending on the cell's current state or function. For example, if protein monomers with the epitope tag 'A' are steadily expressed by the cell, and the expression of protein monomers with the epitope tag 'B' is increased by, say, a neural activity dependent promoter, then the neural activity dependent event will result in permanent storage of the activity record in the order of the epitope tags along the growing protein chain, enabling later readout via immunostaining against tags 'A' and 'B', followed by standard imaging. Recordings using embodiments of compositions and methods of the invention have shown that pharmacological modulation of gene expression histories in living cells and organisms can be read out post hoc.

Information disclosed herein defines, provides rationale for, and validates, a calibratable measure of time, and use of the fractional cumulative expression of a detectable tag bearing monomers, to calibrate the time axis onto the information recorded on the XRI via ordered epitope tags. A non-limiting example of an embodiment of a method of the invention, comprises application of XRIs of the invention to record c-fos promoter-driven gene expression in cultured mouse hippocampal neurons after depolarization, and application of the fractional cumulative expression of HA-bearing monomers to recover the time axis and c-fos promoter-driven gene expression solely from information read out from XRI via immunostaining and imaging. Studies disclosed herein provide evidence that XRI can preserve the temporal order of protein monomers expressed in a living cell, including but not limited to a cell in culture, a cell in a live subject, for example a cell in the brain of a live subject. Thus, XRIs of the invention are capable of functioning in multiple biological systems, including the cells in culture and cells in a live subject, cells in a live mammalian brain, and methods of the invention can use XRIs of the invention to encode cellular physiological signals into a linear, optically readable protein chain.

Compared to nucleic acid-based systems, which require nucleic acid sequencing methods that are destructive to cells [Kording, K. P. *PLOS Comput. Biol.* 7, e1002291 (2011); Perli, S. D., et al., *Science* 2016 Sep. 9;353(6304):aag0511, doi: 10.1126/science.aag0511, Epub 2016 Aug. 18 (2016); Rodriques, S. G. et al. *Nat. Biotechnol.* 2020 393 39, 320-325 (2020); Farzadfard, F. & Lu, T. K. *Science* 2014 Nov. 14; 346(6211): 1256272; Farzadfard, F. & Lu, T. K. *Science.* 361, 870-875 (2018); Farzadfard, F. et al. *Mol. Cell* 75, 769-780.e4 (2019); Sheth, R. U., et al., *Science* 358, 1457-1461 (2017), the content of each of which is incorporated by reference herein in its entirety], reading out recorded information using compositions and methods of the invention through imaging, only requires routine immunofluorescence techniques and conventional microscopes, available in the art, without the need for additional hardware investment. Such preservation of cellular physiological information within the native environment offered by the protein-based compositions and methods of the invention also enable correlation of the recorded biological information with other kinds of structural and molecular information associated with the cellular population, such as the spatial location, cell type, and presence of RNA/protein markers in the recorded cells [Lin, D. et al. *Nature* 470, 221 (2011); Ceccatelli, S, et al., *Proc. Natl. Acad. Sci. U.S.A.* 86, 9569-9573 (1989); Guenthner, C. J., et al., *Neuron* 78, 773-784 (2013), the content of each of which is incorporated by reference herein in its entirety], some of which may be causally involved with the creation of the physiological signals, or that result from the physiological signals. Such kinds of multimodal data may enable the analysis of how specific cellular machinery drive, or result from, complex time courses of physiological stimuli. For example, by offering the ability to record gene expression time course in single cells, as described herein, the protein-based XRI compositions and methods of the invention enable the study of gene expression time course as a result of specific cellular inputs and/or drug treatments [Strober, B. J. et al. *Science* 364, 1287-1290 (2019); Gallo, F. T., et al., *Front. Behav. Neurosci.* Vol, 12, *Article* 79 (2018) doi.org/10.3389/fnbeh.2018.00079, the content of each of which is incorporated by reference herein in its entirety]. Non-limiting examples of the use of compositions and methods of the invention, include their use to investigate circadian genes [Zhang, R., et al, *Proc. Natl. Acad. Sci.* 111, 16219-16224 (2014), the content of which is incorporated by reference herein in its entirety] and other genes that change in complex ways over time; to record transcription factor activities [Elf, J., et al, *Science* 316, 1191 (2007), the content of which is incorporated by reference herein in its entirety]; and as an information storage platform to externally introduce unique cellular barcodes into single cells for cell identification [Viswanathan, S. et al. *Nat. Methods* 12, 568-576 (2015), the content of which is incorporated by reference herein in its entirety].

Compositions and Components

Certain embodiments of a composition of the invention comprise a nucleic acid sequence that encodes an expression-recording island (XRI). Such a composition of the invention comprises a nucleic acid sequence that encodes at least one self-assembling filament forming monomer at least one detectable tag (which may also be referred to herein as an epitope tag); and at least one protein spacer. In some embodiments, a composition of the invention includes a sequence that encodes 1, 2, 3, or more independently selected self-assembling filament forming monomers; 0, 1, 2, 3, or more independently selected detectable tags; and 0, 1, 2, 3, or more independently selected protein spacers. The term "independently selected" used herein in reference to multiple like components, means selection of each like component for inclusion in the composition, independent of the others selected. As a non-limiting example, in a composition of the invention comprising three independently selected protein spacers, the three spacers are considered to be "like components" and each may be selected independent of the others, meaning that in different embodiments of the invention, the three encoded protein spacers may be: all the same, each different from the others, or two the same and one different from the other protein spacers in the composition.

Some embodiments of a composition of the invention comprise an expressed XRI protein. Components of an expressed XRI comprise one or more independently selected self-assembling filament-forming monomers, zero, one, or more independently selected detectable tag (which may also be referred to herein as epitope tags), and zero, one, or more independently selected protein spacers. In some embodiments, a composition of the invention includes 1, 2, 3, 4, 5, 6, or more independently selected self-assembling filament forming monomers; 0, 1, 2, 3, 4, 5, 6, or more independently selected detectable tags; and 0, 1, 2, 3, 4, 5, 6, or more independently selected protein spacers. Some embodiments of a composition of the invention comprise an expressed XRI protein. Components of an expressed XRI in some embodiments, comprise a self-assembling filament-forming monomer, a detectable tag (which may also be referred to herein as epitope tags), and a protein spacer.

Non-limiting examples of self-assembling proteins that may be present in, or encoded in certain embodiments of a composition of the invention, are 1POK and DHF40 proteins. Self-assembling protein encoding sequences and the expressed self-assembling protein may, in some embodiments of the invention be engineered sequences and proteins, respectively. Non-limiting examples of a detectable tag that may be present in, or encoded in certain embodiments of a composition of the invention, is a human influenza hemagglutinin (HA) tag. Non-limiting examples of monomer protein spacers that may be present in, or encoded in certain embodiments of a composition of the invention, are a monomeric mEGFP and a maltose binding protein (MBP).

Expression and Use of XRI Components

Certain embodiments of the invention include compositions as described and methods of using XRI components of the invention for recording cellular physiological histories in living cells. As used herein the term XRI system, XRI recorder, XRI recorder system, and recorder system, refer to an embodiment in which an XRI of the invention is expressed in a living cell, and used to determine an expression history of the cell. In certain aspects of the invention, an XRI reporter system is used in a cell to determine characteristics such as, but not limited to the timing of protein expression and the effect of stimuli on expression in the cell. In some embodiments, a baseline determination of one or more characteristics of expression in a "control" cell can be performed using a method and/or system of the invention. Such baseline determinations may be made for the same characteristics that are also determined in similar cells but under different circumstances. For example, a baseline determination may indicate a "control" characteristic, which can be compared to the characteristic in a "test" cell that is exposed to one or more different stimuli, environmental changes, etc. to which the control cell was not exposed. For example, though not intended to be limiting, a test cell that includes an XRI system of the invention can be contacted with a candidate stimulus and a difference in one or more characteristics in the test cell compared to a control cell not contacted with the candidate stimulus in order to ascertain whether there is an effect of the candidate stimulus on expression in the cell. Non-limiting examples of candidate stimuli are: test agents are: electrical stimulus, a chemical stimulus, a biological stimulus, an inhibitory stimulus, an excitatory stimulus, a signaling molecule, a signaling chemical, a pharmaceutical stimulus, a cellular stimulus, a temperature stimulus, a light stimulus, a candidate compound, a pharmaceutical compound, an electrical stimulus, a chemical stimulus, a biological stimulus. Additional stimuli that are suitable for use in embodiments of the invention are known and routinely used in the art.

It will be understood that in some aspects of the invention, a candidate stimulus may be delivered directly to a cell that includes an XRI recorder system of the invention, or may be delivered to another cell that is in communication with a cell that includes an XRI recorder of the invention. As used herein, the term "in communication with" used in reference to a cell that includes an expressed or encoded XRI recorder of the invention, includes cells, for example, that influence the cell comprising the expressed or encoded XRI recorder, for example, though not intended to be limiting, via a neurotransmitter means, an electrical means, etc. Communication can be direct communication from a cell immediately (directly) upstream from the cell that includes an expressed or encoded XRI recorder of the invention, or can be indirect communication, such as the result of activity of a cell further (indirectly) upstream that impacts the cell in which an expressed or encoded XRI recorder of the invention is included. Stimulation of one or more of a cell directly upstream and a cell indirectly upstream may result in a change in expression in a cell that includes an expressed and/or encoded XRI recorder of the invention, and the presence of the expressed and/or encoded XRI recorder permits determination of changes in characteristics of expression in that cell using methods of the invention. As used herein a change in expression means an alteration in the expression characteristic, for example an increase in a rate or timing of expression, a decrease in a rate or timing of expression, the start of expression, a delay in the start of expression, and the like.

Methods and XRI recorder systems of the invention can be used to assess one or more changes in: (1) an internal environment of a cell, (2) an external environment of a cell, (3) an internal environment of an upstream cell, and (4) an external environment of an upstream cell. Non-limiting examples of events and situations that may change in a cell's internal or external environment and that can directly or indirectly effect expression in a cell comprising an expressed and/or encoded XRI recorder of the invention include, an action potential, a disease or injury condition in the cell or subject comprising the cell, contact of the cell with a candidate stimuli agent or compound, contact of the cell with a pharmaceutical agent or compound, a surgical procedure in the subject, contact of the cell with radiation, light, electric stimulation, etc. Other types of events and actions that alter the internal or external environment of a cell are known in the art, and can also be assessed using methods and XRI recorders ofthe invention.

Components of XRI-based recorder systems of the invention are well suited for targeting cells, expression in cells, and for use to detect and assess expression levels and changes associated with stimuli and/or cell activities. In some embodiments, an expressed and/or encoded XRI recorder system of the invention can be utilized to detect one or more of conductance changes across cell membranes, the impact of endogenous signaling pathways (such as calcium dependent signaling, etc.), and the effect of applied candidate stimuli on a cell that includes the expressed and/or encoded XRI recorder of the invention. Thus, certain aspects of the invention include methods of using XRI-based recorders to screen putative therapeutic agents, known therapeutic agents, combinations of two or more independently selected known and putative therapeutic agents.

One or more XRI-based recorders of the invention can also be used in some embodiments of methods of the invention to assess the effect of internal cellular conditions, environmental conditions external to the cell, and to assess the result diseases, injuries, treatments, etc. on expression in the cell comprising the expressed and/or encoded XRI recorder. Methods and systems of the invention can also be used to examine normal cells in vitro and in vivo. For example, in some embodiments, an XRI recorder system can be used to determine expression events in normal cells and subjects and the resulting information on expression characteristics can be applied in the study of normal cell development, non-limiting examples of which are cell development in regeneration, embryonic cell development, establishment of cell connectivity, and the like.

Molecules and Compounds

The present invention, in part, includes novel XRI-based recorder systems and components thereof, their expression in cells, and their use to determine alterations in characteristics of expression in the cell, which may also be referred to herein as a "host cell." As used herein, the term "host cell" means a cell that includes one or more components of an expressed or encoded XRI-based recorder system of the invention. Non-limiting examples of components of XRI recorder systems of the invention are described herein, see for example, Tables 1-2 and the Examples section. Aspects of the invention also include additional functional variants of components of XRI-based recorder systems described herein, including polynucleotides, polypeptides, compositions comprising the components and functional variants thereof, and methods of using the components and functional variants thereof to perform XRI-based recording in a cell, or in a plurality of cells. As used herein the term "plurality of cells" means more than one cell, which in some embodiments of the invention is more than 1, more than 10, more than 100, more than 1000, more than 10,000, or more than 100,000, and more than 1,000,000, including all integers within the range from 1 to at least 1,000,000.

It is understood that the terms: XRI-based recorder system components encompass molecules, polypeptides, and polynucleotides described herein, as well as functional variants thereof. The invention also includes compounds and compositions that comprise one or more components of an expressed and/or encoded XRI-based recorder system of the invention. A compound or composition that comprises a component of an expressed and/or encoded XRT recorder of the invention may in some embodiments, include one, two, three, four, five, six, or more additional components. Non-limiting examples of additional components are a vector, a promoter, a trafficking sequence, a delivery molecule sequence, an additional sequence, etc.

Certain embodiments of the invention include polynucleotides comprising nucleic acid sequences that encode a component of a XRI recorder system of the invention, and some aspects of the invention comprise methods of delivering and/or using such polynucleotides in cells, tissues, and/or organisms. XRI-based recorder-component polynucleotide sequences and amino acid sequences used in aspects and methods of the invention may be "isolated" sequences. As used herein, the term "isolated" used in reference to a polynucleotide, nucleic acid sequence, polypeptide, or amino acid sequence means a polynucleotide, nucleic acid sequence, polypeptide, or amino acid sequence, respectively, that is separate from its native environment and present in sufficient quantity to permit its identification or use. Thus, a nucleic acid or amino acid sequence that makes up a component of an XRI-based molecular recorder molecule that is present in one or more of a vector, a cell, a tissue, an organism, etc., may be considered to be an isolated sequence if it is not naturally present in that cell, tissue, or organism, and/or did not originate in that cell, tissue, or organism.

A host cell means a cell that comprises one or more components of an expressed and/or encoded XRI-based recorder. In certain aspects of the invention, one or more components of an expressed and/or encoded XRI-based recorder system of the invention are delivered into and/or expressed in a cell. Examples of cells that may be used in embodiments of the invention include, but are not limited to vertebrate cells, mammalian cells (including but not limited to non-human primate, human, dog, cat, horse, mouse, rat, etc.), insect cells (including but not limited to *Drosophila*, etc.), fish, worm, nematode, and avian cells. In some embodiments of the invention, a cell is a plant cell.

One or more components of an XRI-based reporter system of the invention may be derived from (also referred to herein as "being a variant of") one or more components disclosed herein, and they may exhibit the same qualitative function and/or characteristics of the molecular reporter system component from which they have been derived, and/or may show one or more increased or decreased level of a function or characteristic of the parent component. In some embodiments of the invention an effectiveness of a variant or derived component of an XRI reporter system set forth herein may differ from the parent component. For example, in some instances a variant or derived component is capable of faster determination of a characteristic of expression in a host cell than is possible for its parent component.

It is understood in the art that the codon systems in different organisms can be slightly different, and that therefore where the expression of a given protein from a given organism is desired, the nucleic acid sequence can be modified for expression within that organism. Thus, in some embodiments, a polynucleotide that encodes a component of an XRI-based recorder system of the invention comprises a mammalian-codon-optimized nucleic acid sequence, which may, in some embodiments, be a human-codon optimized nucleic acid sequence. Codon-optimized sequences can be prepared using routine methods.

Delivery of XRI-Based Recorder Components

Delivery of one or more components of an XRI-based recorder of the invention to a cell and/or expression of the component in a cell can be done using art-known delivery means. [see for example, Chow et al. *Nature* 2010 Jan. 7;463(7277):98-102; and for Adeno-associated virus injection: Betley, J. N. & Sternson, S. M. (2011) Hum. Gene Ther. 22, 669-677; for In utero electroporation: Saito, T. & Nakatsuji, N. (2001) Dev. Biol. 240, 237-46; for microinjection into zebrafish embryos: Rosen J. N. et al., (2009) *J. Vis. Exp.* (25), e 1115, doi:10.3791/1115; and for DNA transfection for neuronal culture: Zeitelhofer, M. et al., (2007) Nature Protocols 2, 1692-1704, the content of each of which is incorporated by reference herein in its entirety].

In some embodiments of the invention a component of an XRI-based recorder of the invention is included as part of a fusion protein. It is well known in the art how to encode, prepare, and utilize fusion proteins that comprise a polypeptide sequence. In certain embodiments of the invention, a vector that encodes a fusion protein can be prepared and used to deliver a component of an XRI-based recorder system of the invention to a cell and can also in some embodiments be used to target delivery of a component of an XRI-based recorder system of the invention to a specific cell, cell type, tissue, or region in a subject. Suitable targeting sequences useful to deliver a component of an XRI-based recorder of the invention to a cell, tissue, region of interest are known in the art. Delivery of a component of an XRI-based recorder system of the invention to a cell, tissue, or region in a subject can be performed using art-known procedures. A fusion protein of the invention can be delivered to a cell by delivery of a vector encoding the XRI-containing fusion protein. The delivered fusion protein is then expressed in a specific cell type, tissue type, organ type, and/or region in a subject, or in vitro, for example in culture, in a slice preparation, etc.

In certain aspects of the invention, a component of an XRI-based recorder system of the invention is non-toxic or substantially non-toxic to the cell into which it is delivered and/or expressed. In some embodiments of the invention, a component of an XRI-based recorder of the invention is genetically introduced into a cell, and reagents and methods are provided for genetically targeted expression of components of an XRI-based recorder system of the invention. Genetic targeting can be used to deliver one or more components of an XRI-based recorder system of the invention to specific cell types, to specific cell subtypes, to specific spatial regions within an organism. In some embodiments of the invention, targeting can be used to control of the amount of a component of an XRI-based recorder system of the invention that is expressed and the timing of the expression. Preparation, delivery, and use of a fusion protein and its encoding nucleic acid sequences are well known in the art. Routine methods can be used in conjunction with teaching herein to express one or more XRI-based recorder system components and optionally additional polypeptides, in a desired cell, tissue, or region in vitro or in a subject.

Vectors, Plasmids, and Molecules

Some embodiments of the invention include a reagent for genetically targeted expression of a component of an XRI-based recorder of the invention, wherein the reagent comprises a vector that contains the gene for the component. As used herein, the term "vector" refers to a nucleic acid molecule capable of transporting between different genetic environments another nucleic acid to which it has been operatively linked. The term "vector" may also refer to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors." Other useful vectors, include, but are not limited to viruses such as lentiviruses, retroviruses, adenoviruses, and phages. Vectors useful in some methods of the invention can genetically insert an XRI-based recorder system of the invention into dividing and non-dividing cells and can insert an XRI-based recorder system of the invention into an in vivo, in vitro, or ex vivo cell.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein. In certain embodiments of the invention, a vector may be a lentivirus comprising the gene for an XRI-based recorder system of the invention. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of an XRI-based recorder system of the invention in a wide variety of cell types—thus a promoter for a gene that is widely expressed in a variety of cell types, for example a "housekeeping gene" can be used to express an XRI-based recorder system component(s) of the invention in a variety of cell types. Non-limiting examples of general promoters are provided elsewhere herein and suitable alternative promoters are well known in the art. In certain embodiments of the invention, a promoter may be an inducible promoter, examples of which include, but are not limited to tetracycline-on or tetracycline-off, or tamoxifen-inducible Cre-ER.

In some embodiments of the invention a reagent for expression of a component of an XRI-based recorder system of the invention is a vector that comprises a gene encoding the component, and optionally a gene encoding one or more additional polypeptides. Vectors useful in methods of the invention may include additional sequences including, but not limited to, one or more signal sequences and/or promoter sequences, or a combination thereof. In certain embodiments of the invention, a vector may be a lentivirus, adenovirus, adeno-associated virus, or other vector that comprises a gene encoding XRI-based recorder system component(s) of the invention. An adeno-associated virus (AAV) such as AAV8, AAV1, AAV2, AAV4, AAV5, AAV9, are non-limiting examples of vectors that may be used to express a fusion protein of the invention in a cell and/or subject. Expression vectors and methods of their preparation and use are well known in the art. Non-limiting examples of suitable expression vectors and methods for their use are provided herein. Other vectors that may be used in certain embodiments of the invention are provided in the Examples section herein.

Promoters that may be used in methods and vectors of the invention include, but are not limited to, cell-specific promoters or general promoters. Non-limiting examples promoters that can be used in vectors of the invention are: ubiquitous promoters, such as, but not limited to: CMV, CAG, CBA, and EFla promoters; and tissue-specific promoters, such as but not limited to: Synapsin, CamKIIa, GFAP, RPE, ALB, TBG, MBP, MCK, TNT, and aMHC promoters. In some embodiments, a promoter included in a method and/or vector of the invnetnio is a UBC promoter. Methods to select and use ubiquitous promoters and tissue-specific promoters are well known in the art. A non-limiting example of a tissue-specific promoter that can be used to express a component of an XRI-based recorder system of the invention in a cell such as a neuron is a synapsin promoter, which can be used to express the component in certain embodiments of methods of the invention. Additional tissue-specific promoters and general promoters are well known in the art and, in addition to those provided herein, may be suitable for use in compositions and methods of the invention. Other non-limiting examples of promoters that may be used in certain embodiments of methods of the invention are provided in the Examples section.

Non-limiting examples of detectable label polypeptides that may be included in a composition comprising a component of an XRI-based recorder system of the invention are: green fluorescent protein (GFP); enhanced green fluorescent protein (EGFP), red fluorescent protein (RFP); yellow fluorescent protein (YFP), dtTomato, mCardinal, mCherry, DsRed, cyan fluorescent protein (CFP); far red fluorescent proteins, etc. Numerous fluorescent proteins and their encoding nucleic acid sequences are known in the art and routine methods can be used to include such sequences in fusion proteins and vectors, respectively, of the invention.

Additional sequences that may be included in a fusion protein comprising a component of an XRI-based molecular recorder system of the invention are trafficking sequences, including, but not limited to: Kir2.1 sequences and functional variants thereof, KGC sequences, ER2 sequences, etc. Trafficking polypeptides and their encoding nucleic acid sequences are known in the art and routine methods can be used to include and use such sequences in fusion proteins and vectors, respectively, of the invention.

Table 2 provides a list of constructs that have been prepared and used in XRI-based recorder systems and components of the invention.

TABLE 2 constructs of self-assembly proteins tested in neurons in this study

| Construct (promoters are underlined) | Resulted pattern of protein self-assembly (in the cytosol unless noted otherwise) |
|---|---|
| UBC-1POK(E239Y)-Linker25-HA-Linker3-MBP_tag (also known as XRI-HA) | Fiber(s) |
| UBC-1POK(E239Y)-Linker12-gg-HA | Unstructured aggregates and intertwined fibers |
| UBC-1POK(E239Y)-Linker13-HA-mEGFP | Fiber(s) |
| UBC-1M3U(D157L,E158L,D161L)-Linker14-HA | Unstructured aggregates (and intertwined fibers in a subset of cells) |
| UBC-HA-Linker14-2CG4(K126Y,D131Y) | Uniform expression in the nucleus |
| UBC-2VYC(K491L,D494L,D497L)-Linker14-HA | Nucleus-localized puncta and cytosol-localized puncta |
| CMV-1POK(E239Y)-Linker8-HA | Unstructured aggregates and intertwined fibers |
| UBC-1POK(E239Y)-Linker7-HA-Linker3-MBP_tag | Fiber(s) |
| UBC-HA-Linker3-MBP_tag-Linker18-1POK(E239Y) | Fiber(s) |
| UBC-1POK(E239Y)-Linker5-HA-mEGFP | Fibers (mostly) and puncta |
| UBC-mEGFP-HA-Linker12-1POK(E239Y) | Fiber(s) |
| UBC-1POK(E239Y)-Linker25-HA-g-mEGFP | Fiber(s) |
| UBC-1POK(E239Y)-Linker7-HA-Linker3-Top7 | Short fibers and puncta in the nucleus (mostly) and cytosol |
| UBC-1POK(E239Y)-Linker25-HA-gsg-Top7 | Unstructured aggregates and intertwined fibers in the cytosol; nucleus-localized fibers |
| UBC-1POK(E239Y)-Linker5-mEGFP-Linker2-HA-Linker3-MBP_tag | Puncta |
| UBC-1POK(E239Y)-Linker24-mEGFP-HA-Linker6-MBP | Fiber(s) with large thickness |
| UBC-1POK(E239Y)-Linker5-mEGFP-HA-Linker3-Top7 | Dense and small puncta |
| UBC-Top7-Linker12-1POK(E239Y)-Linker13-HA-mEGFP | Unstructured aggregates and fibers; high non-assembly background |
| UBC-1POK(E239Y)-Linker24-mEGFP-HA-Linker6-Top7 | Unstructured aggregates and fibers in the cytosol; nucleus-localized fibers |

TABLE 2-continued constructs of self-assembly proteins tested in neurons in this study

| Construct (promoters are underlined) | Resulted pattern of protein self-assembly (in the cytosol unless noted otherwise) |
|---|---|
| UBC-HA-dTor_12x31L-Linker24-1POK(E239Y) | Puncta |
| UBC-NLS-Linker4-1POK(E239Y)-Linker13-HA-mEGFP | Nucleus-localized fiber(s) |
| UBC-NLS-Linker4-1POK(E239Y)-Linker14-HA | Nucleus-localized puncta |
| UBC-DHF40-Linker14-HA | Unstructured aggregates and intertwined fibers |
| UBC-DHF40-Linker13-HA-mEGFP | Unstructured aggregates, puncta, and intertwined fibers |
| UBC-DHF58Four-Linker14-HA | Unstructured aggregates (and intertwined fibers in a subset of cells) in the cytosol and nucleus |
| UBC-DHF58Six-Linker14-HA | Uniform expression in the nucleus, with dim unstructured aggregates in the cytosol |
| UBC-DHF58Six-Linker14-mRuby2_smFP(HA) | Uniform expression in the nucleus, with dim unstructured aggregates in the cytosol |
| UBC-DHF79-Linker14-HA | Uniform expression in the nucleus, with dim unstructured aggregates in the cytosol |
| UBC-DHF 119-Linker14-HA | Uniform expression in the nucleus, with dim unstructured aggregates in the cytosol |
| CMV-DHF40-Linker8-HA | Unstructured aggregates and intertwined fibers |
| CMV-DHF46-Linker8-HA | Puncta |
| CMV-DHF47-Linker8-HA | Unstructured aggregates and puncta |
| CMV-DHF50-Linker8-HA | Unstructured aggregates and puncta |
| CMV-DHF77-Linker8-HA | Unstructured aggregates and puncta |
| UBC-γPFD-Linker8-HA | Puncta |

Sequences of three non-limiting examples of XRIs, each with a unique epitope tag, are set forth herein as (1) Synthetic construct XRI-HA gene, Genbank® OK539810 (amino acid sequence is SEQ ID NO: 26; DNA sequence is SEQ ID NO: 27); (2) synthetic construct XRI-FLAG gene, Genbank© OK539811 (amino acid sequence is SEQ ID NO: 28; DNA sequence is SEQ ID NO: 29); and (3) synthetic construct XRI-V5 gene, Genbank® OK539812 (amino acid sequence is SEQ ID NO: 30; DNA sequence is SEQ ID NO: 31).

Cells and Subjects

Some aspects of the invention include cells used in conjunction with an XRI-based recorder system of the invention. Cells in which an XRI-based recorder system component may be expressed, and that can be used in methods of the invention, include prokaryotic and eukaryotic cells. Certain embodiments of the invention include use of mammalian cells; including but not limited to cells of humans, non-human primates, dogs, cats, horses, rodents, etc. In some embodiments of the invention, cells that are used are non-mammalian cells; including but not limited to insect cells, avian cells, fish cells, plant cells, etc. An XRI-based recorder system of the invention may be included in non-excitable cells and in excitable cells, the latter of which include cells able to produce and respond to electrical signals. Examples of excitable cell types include, but are not limited, to neurons, muscle cells, visual system cells, sensory cells, auditory cells, cardiac cells, and secretory cells (such as pancreatic cells, adrenal medulla cells, pituitary cells, etc.), cardiac cells, immune system cells, etc.

Cells in which an XRI-based recorder system of the invention can be used include embryonic cells, stem cells, pluripotent cells, mature cells, geriatric cells, as well as cells in other developmental stages. Non-limiting examples of cells that may be used in methods of the invention include neuronal cells, nervous system cells, cardiac cells, circulatory system cells, kidney cells, liver cells, epidermal cells, visual system cells, auditory system cells, secretory cells, endocrine cells, and muscle cells.

In some embodiments, a cell used in conjunction with methods and an XRI-based recorder system of the invention is a healthy normal cell that is not known or suspected of having a disease, disorder, or abnormal condition. In some embodiments of the invention, a cell used in conjunction with methods and an XRI-based recorder system of the invention may in some embodiments be a normal cell or in some embodiments is an abnormal cell. Non limiting examples of elements of an abnormal cell are: (1) a cell that has a disorder, disease, or condition; (2) a cell obtained from a subject that has, had, or is suspected of having disorder, disease, or condition; (3) a cell known to be or suspected of being involved in a disorder, disease, or condition; and (4) a cell that is a model for a disorder, disease, or condition, etc. Non-limiting examples of such cells are a degenerative cell, a neurological disease-bearing cell, a cell model of a disease or condition, an injured cell, a cell downstream from a disease-bearing or injured cell, etc. In some embodiments of the invention, a cell may be a control cell. A cell that is directly or indirectly upstream from a cell in which an XRI-based recorder system may be included may be a normal cell or may be an abnormal cell.

An embodiment of an XRI-based recorder system of the invention may be included in a cell from or in culture, a cell in solution, a cell obtained from a subject, and/or a cell in a subject (in vivo cell). In some embodiments of the invention, an XRI-based recorder system is present in and monitored in cultured cells, cultured tissues (e.g., brain slice preparations, etc.), and in living subjects, etc. As used herein, a the term "subject" may refer to a human, non-human primate, cow, horse, pig, sheep, goat, dog, cat, bird, rodent, fish, insect, or other vertebrate or invertebrate organism. In certain embodiments, a subject is a mammal and in certain embodiments, a subject is a human. Additional non-limiting examples of cell types that may be used in certain methods of the invention are provided in the Examples section, as are non-limiting examples of organisms that may subjected to certain methods of the invention.

A cell that includes an XRI-based recorder system and/or component of the invention may be a single cell, an isolated cell, a cell in culture, an in vitro cell, an in vivo cell, an ex vivo cell, a cell in a tissue, a cell in a subject, a cell in an organ, a cell in a cultured tissue, a cell in a neural network, a cell in a brain slice, a neuron, a cell that is one of a plurality of cells, a cell that is one in a network of two or more interconnected cells, a cell in communication with another cell, a cell that is one of two or more cells that are in physical contact with each other, etc. It will be understood that methods of the invention can be carried out in a plurality of cells such that one or more cells comprises the XRI-based recorder system of the invention. Inclusion of a system of the invention in a plurality of cells permits monitoring and determining one or more alterations in expression across the plurality of cells. It will be understood that when assessing expression and history in a plurality of cells, a plurality of cells may be prepared to contain an expressed and/or encoded XRI recorder of the invention and the status of expression in the plurality of cells can be determined at one or more different time points by obtaining one or more cells from the plurality at the one or more different time points and determining the expression and/or history in the obtained cell or cells. At a different time point, another cell or other cells may be obtained from the plurality of cells and also assessed. Results of two or more assessments done in cells obtained from the plurality at different times can be compared to determine a change in expression in the plurality of cells. Results using cells obtained at two or more times can be used to assess changes in expression in the plurality of cells over time and under different conditions. For example, one or more cells may be obtained from a plurality of cells comprising expressed and/or encoded XRI of the invention and assessed for expression, then the plurality of cells may be contacted with a candidate stimuli and another cell or cells obtained following the contact can be assessed and compared to the initial assessment or a control assessment as a determination of the expression history of the plurality of cells.

Controls

An XRI-based recorder system of the invention and methods of using such recorder systems can be utilized to assess changes in cells, tissues, and subjects in which the system is included. Some embodiments of the invention include use of an XRI-based recorder system of the invention to identify effects of candidate stimuli on cells, tissues, and subjects. Results of testing cell expression activity using an XRI-based recorder of the invention can be advantageously compared to a control. In some embodiments of the invention, an XRI-based recorder system may be in a cell or cell population and used to test the effect of candidate stimuli on the cell or population, respectively. A "test" cell, tissue, or organism may be a cell, tissue, or organism in which activity of an XRI-based recorder system of the invention can be determined or assayed. Results obtained using assays and tests of a test cell, tissue, or organism may be compared with results obtained from the assays and tests performed in other test cells, tissues, or organisms or assays and tests performed in control cells, tissues, or organisms.

As used herein a control value may be a predetermined value, which can take a variety of forms. It can be a single cut-off value, such as a median or mean. It can be established based upon comparative groups, such as cells or tissues that include an XRI-based recorder system of the invention that is under essentially the same conditions of test cells but are not contacted with a candidate compound. Another non-limiting example of a comparative group includes cells or tissues that have a disorder or condition and groups without the disorder or condition. Another non-limiting example of comparative group includes cells from a subject or subjects with a family history of a disease or condition and cells from a subject or subjects without such a family history. A predetermined value can be arranged, for example, where a tested population is divided equally (or unequally) into groups based on results of testing. Those skilled in the art are able to select appropriate control groups and values for use in comparative methods of the invention.

Administration Means

Administration of a component of an XRI-based recorder system of the invention may include, but is not limited to: administering to a cell or subject a composition that includes a vector comprising a polynucleotide sequence that encodes the XRI, administering to a cell or subject a composition comprising the vector, and administering to a subject a cell in which the vector and/or encoded XRI is present. A composition of the invention optionally includes a carrier, which may be a pharmaceutically acceptable carrier.

A component of an XRI-based recorder system of the invention may be administered to a cell and/or subject in a formulation, which may be administered in pharmaceutically acceptable solutions, which may routinely contain pharmaceutically acceptable concentrations of salt, buffering agents, preservatives, compatible carriers, adjuvants, and optionally additional ingredients. In some aspects, a pharmaceutical composition comprises one or more XRI-based recorder system component(s) of the invention and a pharmaceutically-acceptable carrier. Pharmaceutically acceptable carriers are well known to the skilled artisan and may be selected and utilized using routine methods. As used herein, a pharmaceutically acceptable carrier means a non-toxic material that does not interfere with the effectiveness of the biological activity of the active ingredients. Pharmaceutically acceptable carriers may include diluents, fillers, salts, buffers, stabilizers, solubilizers, and other materials that are well known in the art. Exemplary pharmaceutically acceptable carriers are described in U.S. Pat. No. 5,211,657 and others are known by those in the art.

The terms "delivery into" and "include" when used herein to describe an action that results in a component of an XRI-based recorder system of the invention being present in a cell, are intended to encompass delivery of the component (s) into the cell (for example, though not intended to be limiting, in the form of a fusion protein), and delivery of a polynucleotide sequence that encodes the component and that is subsequently expressed in the cell. A component of an XRI-based recorder system of the invention may be administered using art-known methods. The absolute amount to be delivered can be determined using routine methods. The delivery may be done in a single administration, a single or multiple deliveries, and if delivered into a subject may be based on individual subject parameters including age, physical condition, size, weight, and the stage of a disease or condition, test parameters to be followed, etc. These factors can be addressed with no more than routine experimentation.

Various modes of administration will be known to one of ordinary skill in the art that can be used to effectively deliver one or more components of an XRI-based recorder system of the invention in a desired cell, tissue, cell of a subject, organ of a subject, or region of a subject. Methods for administering a composition comprising a component of an XRI-based recorder system of the invention may include, but are not limited to: injection, microinjection, perfusion, electroporation, or other suitable means. The invention is not limited by the particular modes of administration disclosed herein and additional art-known delivery means may be suitable for administration of components of an XRI-based recorder system of the invention.

Other protocols suitable for administration of one or more components that are part of an XRI-based recorder system of the invention are known to those in the art. Embodiments of methods of the invention to administer a cell or vector to increase a level of a component of an XRI-based recorder system of the invention in an animal other than a human; and administration and use of an XRI-based recorder system of the invention for testing purposes or veterinary purposes, are substantially the same as described above. It will be understood by a skilled artisan that this invention is applicable to both human and animals.

Assessment Methods

Disorders, conditions, and events that may be assessed using methods of the invention to include an XRI-based recorder of the invention in a cell, tissue, and/or subject and to use the system to determine characteristics of expression in the cell. Methods and systems of the invention may be used to assess early stage development, cell and tissue regeneration, cell communication, disease, etc. Diseases that may be examined using methods and systems of the invention include, but are not limited to injury, brain damage, spinal cord injury, epilepsy, metabolic disorders, cardiac dysfunction, vision loss, blindness, deafness, hearing loss, and neurological conditions (e.g., Parkinson's disease, Alzheimer's disease, and seizure), degenerative neurological conditions, drug contact, toxins, etc. In some embodiments of the invention, a disorder or condition may be monitored by including an XRI-based recorder system of the invention in at least one cell and monitoring characteristics of expression in the cells using the recorder system. In some embodiments of the invention, such methods can be used in methods such as, but not limited to, assessing therapeutic agents and treatments, assessing putative therapeutic agents and treatments, expanding understanding of connectivity between cells, and exploring expression activity patterns in a cell or cells. An XRI-based recorder system of the invention may be targeted to cells and used to monitor expression changes in such cells.

The present invention in some aspects, includes one or more of preparing nucleic acid sequences that encode one or more components of an XRI-based recorder system of the invention, expressing in cells one or more components of an XRI-based recorder system encoded by the prepared nucleic acid sequences; and monitoring changes expression in the cell by assessing changes in a level of expressed protein, determine an amino acid sequence of proteins expressed in the cell, and/or determining the presence, location, and/or amount of one or more XRI detectable tags expressed in the cell. The ability to specifically, consistently, reproducibly, and sensitively monitor changes in the XRI composition using methods such as imaging and amino acid sequence determination and single cell assessment of such characteristics has been demonstrated. The present invention enables monitoring of expression changes in in vivo, ex vivo, and in vitro, and the XRI-based recorder system and its use have broad-ranging applications for drug screening, disease assessment, treatment assessment, and research applications, some of which are describe herein.

EXAMPLES

Example 1

Materials and Methods:

Animals and Neuron Cultures.

All procedures involving animals at Massachusetts Institute of Technology were conducted in accordance with the US National Institutes of Health *Guide for the Care and Use of Laboratory Animals* and approved by the Massachusetts Institute of Technology Institutional Animal Care and Use and Biosafety Committees.

FIGS. 1-3 and 5-10 show results of experiments utilizing hippocampal neurons that were prepared from postnatal day 0 or 1 Swiss Webster mice (Taconic) (both male and female mice were used) as previously described [Klapoetke, N. C. et al. *Nat. Methods* 11, 338-46 (2014)] with the following modifications: dissected hippocampal tissue was digested with 50 units of papain (Worthington Biochem) for 6-8 minutes, and the digestion was stopped with ovomucoid trypsin inhibitor (Worthington Biochem). Cells were plated at a density of 20,000-30,000 per glass coverslip coated with diluted Matrigel in a 24-well plate. Cells were seeded in 100 μL neuron culture media containing Minimum Essential Medium (MEM, no glutamine, no phenol red; Gibco), glucose (25 mM, Sigma), holo-Transferrin bovine (100 μg/mL, Sigma), HEPES (10 mM, Sigma), glutaGRO (2 mM, Corning), insulin (25 μg/mL, Sigma), B27 supplement (1×, Gibco), and heat inactivated fetal bovine serum (10% in volume, Corning), with final pH adjusted to 7.3-7.4 using NaOH. After cell adhesion, additional neuron culture media was added. AraC (2 μM, Sigma) was added at 2 days in vitro (DIV 2), when glial density was 50-70% of confluence. Neurons were grown at 37° C. and 5% $CO_2$ in a humidified atmosphere in a neuron incubator, with 2 ml total media volume in each well of the 24-well plate.

Molecular Cloning.

The DNAs encoding the protein motifs used in this study were mammalian-codon optimized and synthesized by Epoch Life Science and then cloned into mammalian expression backbones, pAAV-UBC (for constitutive expression), pAAV-UBC-FLEx (for Cre-dependent expression), or pAAV-cFos (for expression driven by the c-fos promoter) for DNA transfection in cultured neurons and AAV production by Janelia Viral Tools. See Table 1 for sequences of the motifs; see Table 2 for all tested constructs.

DNA Transfection and AAV Transduction.

For experiments with results shown in FIG. 1D FIG. 1G, FIG. 2A-B cultured neurons were transfected at 7 days in vitro (DIV) with a commercial calcium phosphate transfection kit (Invitrogen) as previously described [Piatkevich, K. D. et al. *Nat. Chem. Biol.* 14, 352-360 (2018)]. Briefly, for transfection in each coverslip/well in the 24-well plate, 5-50 ng of total XRI plasmids (5-25 ng of each plasmid when co-transfecting multiple plasmids), 200 ng pAAV-Syn-ERT2-iCre-ERT2 plasmid (only added in neurons for 4-OHT induction experiments), and pUC19 plasmid as a 'dummy' DNA plasmid to bring the total amount of DNA to 1500 ng (to avoid variation in DNA-calcium phosphate co-precipitate formation) were used. The cells were washed with acidic MEM buffer [containing 15 mM HEPES with final pH 6.7-6.8 adjusted with acetic acid (Millipore Sigma)] after 45-60 minutes of calcium phosphate precipitate incubation to remove residual precipitates.

For experiments with results shown in FIG. 1H-J, FIGS. 2, 3, 5, 6, and 8-10 cultured neurons were transduced at 7 days in vitro (DIV) with AAVs by adding the concentrated AAV stocks (serotype AAV9; Janelia Viral Tools) into neuron culture media at the following final concentrations in the 2 ml neuron culture media per well: for 4-OHT induction experiments, AAV9-UBC—XRI-HA at $5.56\times10^9$ GC/ml, AAV9-UBC-FLEx-XRI-FLAG at $1.88\times10^{10}$ GC/ml, and AAV9-Syn-ERT2-iCre-ERT2 at $8.60\times10^9$ GC/ml; for c-fos recording experiments, AAV9-UBC—XRI-HA at $5.56\times10^9$ GC/ml and AAV9-cFos-XRI-V5 at $1.39\times10^9$ GC/ml; for XRI live cell imaging and electrophysiology experiments, AAV9-UBC-mEGFP-P2A-XRI-HA at $2.78\times10^{10}$ GC/ml.

Chemical Treatments and Stimulations of Cultured Cells.

In 4-OHT induction experiments, (results in FIGS. 1, and 2-6), the original neuron culture media of neuron cultures were transferred into a new 24-well plate, where the media from different neuron cultures were stored in different wells, and kept in the neuron incubator until the end of 4-OHT treatment. 2 ml of fresh neuron culture media containing 1 μM 4-hydroxytamoxifen (4-OHT; Sigma H6278) was added into each well of neuron culture. The neuron cultures were then placed back to the neuron incubator and incubated for 15 minutes, followed by a brief wash of MEM media. Finally, the MEM media was removed and the original neuron culture media was transferred back to the corresponding wells of the neuron cultures. The neuron cultures were then placed back to the neuron incubator.

For potassium chloride (KCl) treatments (results in FIGS. 9 and 10), the potassium chloride (KCl) depolarization solution was prepared, which contains 170 mM KCl, 2 mM $CaCl_2$, 1 mM $MgCl_2$, and 10 mM HEPES. Then, the KCl depolarization media was prepared by mixing the KCl depolarization solution and fresh neuron culture media at the volume ratio of 1:2.32, so that the final concentration of $K^+$ after mixing is 55 mM (taking account the $K^+$ from the fresh neuron culture media). The original neuron culture media of neuron cultures were transferred into a new 24-well plate, where the media from different neuron cultures were stored in different wells, and kept in the neuron incubator until the end of the KCl-induced depolarization treatment. Two ml of KCl depolarization media was added into each well of neuron culture. The neuron cultures were then placed back to the neuron incubator and incubated for 10 min, 30 min, 1 hour, or 3 hours. Finally, the KCl depolarization media was removed and the original neuron culture media was transferred back to the corresponding wells of the neuron cultures. The neuron cultures were then placed back to the neuron incubator.

DNA Transfection in Cultured U2OS Cells.

Human bone osteosarcoma epithelial cells (U20S cells; ATCC) were maintained between 10% and 90% confluence at 37° C. with 5% CO2 in DMEM (Gibco) with the addition of 10% heat inactivated fetal bovine serum (HI-FBS) (Corning), 1% penicillin/streptomycin (Gibco), and 1% sodium pyruvate (Gibco), in glass-bottom 24-well plates pre-treated with 75 μL diluted Matrigel (250 μL Matrigel (Corning) diluted in 12 mL DMEM) per well at 37° C. for 30-60 minutes. The DNA plasmid was transiently transfected into U20S cells using the TransIT-X2 Dynamic Delivery System kit (Mirus Bio) according to the manufacturer's protocol.

Electrophysiology.

For experiments with results shown in FIG. 3A-E, whole cell patch clamp recordings were performed using Axopatch 200B or Multiclamp 700B amplifiers, a Digidata 1440 digitizer, and a PC running pClamp (Molecular Devices). Cultured neurons were patched on DIV 14-16 (7-9 days after AAV transduction). Neurons were bathed in room temperature Tyrode solution containing 125 mM NaCl, 2 mM KCl, 3 mM $CaCl_2$, 1 mM $MgCl_2$, 10 mM HEPES, 30 mM glucose and the synaptic blockers 0.01 mM NBQX and 0.01 mM GABAzine. The Tyrode solution pH was adjusted to 7.3 with NaOH and the osmolarity was adjusted to 300 mOsm with sucrose. Borosilicate glass pipette (Warner Instruments) with an outer diameter of 1.2 mm and a wall thickness of 0.255 mm was pulled to a resistance of 5-10 MΩ with a P-97 Flaming/Brown micropipette puller (Sutter Instruments) and filled with a pipette solution containing 155 mM K-gluconate, 8 mM NaCl, 0.1 mM $CaCl_2$, 0.6 mM $MgCl_2$, 10 mM HEPES, 4 mM Mg-ATP, and 0.4 mM Na-GTP. The pipette solution pH was adjusted to 7.3 with KOH and the osmolarity was adjusted to 298 mOsm with sucrose.

Animals and Mouse Surgery.

All procedures involving animals at Boston University were conducted in accordance with the US National Institutes of Health Guide for the Care and Use of Laboratory Animals and approved by the Boston University Institutional Animal Care and Use and Biosafety Committees.

For experiments with results shown in FIG. 2J-K, FIG. 4, and FIG. 11, all surgeries were performed under stereotaxic guidance and subsequent coordinates are given relative to Bregma (in mm) dorsal ventral injections were calculated and zeroed out relative to the skull. Wild type C57BL/6 mice (3 months of age; Charles River Labs) were placed into a stereotaxic frame (Kopf Instruments) and anesthetized with 3% isoflurane during induction and lowered to 1-2% to maintain anesthesia throughout the surgery. Ophthalmic ointment was applied to both eyes to prevent corneal desiccation. Hair was removed with a hair removal cream and the surgical site was cleaned three times with ethanol and betadine. Following this, an incision was made to expose the skull. Bilateral craniotomies involved drilling windows through the skull above the injection site using a 0.5 mm diameter drill bit. Coordinates were −2.0 anteroposterior (AP), ±1.5 mediolateral (ML), and −1.5 dorsoventral (DV) for dorsal CA1.

For experiments with results shown in FIG. 11, the AAV mixture for injection was prepared by mixing the AAV stocks (serotype AAV9; Janelia Viral Tools) at the following final concentrations: AAV9-UBC—XRI-HA at $1.48\times10^{13}$ GC/ml, AAV9-UBC-FLEx-XRI-FLAG at $3.77\times10^{13}$ GC/ml, and AAV9-Syn-ERT2-iCre-ERT2 at $1.72\times10^{13}$ GC/ml. For experiments with results shown in FIG. 2J-K and FIG. 4, the following AAV concentrations were used for injection (serotype AAV9; Janelia Viral Tools): AAV9-Syn-GFP at $5.75\times10^{13}$ GC/ml; AAV9-UBC—XRI-HA at $1.00\times10^{13}$ GC/ml. Mice were injected with 1 μl of the AAV mixture at the target site using a mineral oil-filled 33-gauge beveled needle attached to a 10 μl Hamilton microsyringe (701LT; Hamilton) in a microsyringe pump (UMP3; WPI). The needle remained at the target site for five minutes post-injection before removal. Mice received 0.1 ml of 0.3 mg/ml buprenorphine intraperitoneally following surgery and were placed on a heating pad during surgery and recovery.

4-Hydroxytamoxifen Injection.

For experiments with results shown in FIG. 11, 4-Hydroxytamoxifen (4-OHT; Sigma) was dissolved in 100% ethanol (Sigma) at 100 mg/ml by vortexing for 5 minutes.

Next, the solution was mixed with corn oil (Sigma) to obtain a final concentration of 10 mg/ml 4-OHT by vortexing for 5 minutes and then sonicating for 30-60 minutes until the solution was clear. The 10 mg/ml 4-OHT solution was then loaded into syringes and administered to mice via intraperitoneal (i.p.) injection at 40 mg/kg.

Histology.

For experiments with results shown in FIG. 2J-K, FIG. 4, and FIG. 11, mice were transcardially perfused with 1×PBS followed by 4% paraformaldehyde in 1X PBS. The brain was gently extracted from the skull and post-fixed in 4% paraformaldehyde in 1×PBS overnight at 4° C. The brain was then incubated in 100 mM glycine in 1×PBS for 1 hour at RT, and then the brain was transferred into 1X PBS and stored at 4° C. until slicing. The brain was sliced to 50-μm thickness coronally using a vibratome (Leica), and then stored in 1×PBS at 4° C. until immunofluorescence staining.

Immunofluorescence.

Immunofluorescence of Cultured Cells.

In studies with results shown in FIGS. 1, 2, 5-9, and 10C-D cells were fixed in TissuePrep buffered 10% formalin for 10 minutes at room temperature (RT) followed by three washes in 1×PBS, 5 minutes each at RT. Cells were then incubated in MAXBlock Blocking medium (Active Motif) supplemented with final concentrations of 0.1% Triton X-100 and 100 mM glycine for 20 minutes at RT, followed by three washes in MAXwash Washing Medium (Active Motif), 5 minutes each at RT. Next, cells were incubated with primary antibodies in MAXStain Staining medium (Active Motif) at 1:500 overnight at 4° C., followed by three washes in MAXwash Washing medium, 5 minutes each at RT. Cells were then incubated with fluorescently-labeled secondary antibodies and NeuroTrace Blue Fluorescent Nissl Stain (Invitrogen) in MAXStain Staining medium, all at 1:500, overnight at 4° C., followed by three washes in MAXwash Washing medium, 5 minutes each at RT. The cells were then stored in 1×PBS at 4° C. until imaging.

Immunofluorescence of Brain Slices.

In studies with results shown in FIGS. 2, 4, and 11 brain slices were blocked overnight at 4° C. in MAXBlock Blocking medium, followed by four washes for 30 minutes each at RT in MAXWash Washing medium. Next, slices were incubated with primary antibodies in MAXStain Staining medium at 1:250 overnight at 4° C., and then washed in MAXWash Washing medium four times for 30 minutes each at RT. Next, slices were incubated with fluorescently-labeled secondary antibodies at 1:500 and NeuroTrace Blue Fluorescent Nissl Stain (Invitrogen) at 1:250 in MAXStain Staining medium overnight at 4° C., and then washed in MAXWash Washing medium four times for 15 minutes each at RT. The slices were then stored in 1×PBS at 4° C. until imaging.

Expansion Microscopy of Cultured Cells.

In studies with results shown in FIG. 8, cell cultures on round coverslips were fixed in 4% paraformaldehyde (Electron Microscopy Sciences) and 0.1% glutaraldehyde (Electron Microscopy Sciences) in 1×PBS for 10 min at RT. Cells were then incubated in 0.1% sodium borohydride (Sigma) in 1×PBS for 7 min and then 100 mM glycine (Sigma) in 1×PBS for 10 min, both at RT.

Acryloyl-X (6-((acryloyl)amino)hexanoic acid, succinimidyl ester (AcX) (Invitrogen) was resuspended in anhydrous DMSO (Invitrogen) at a concentration of 10 mg/ml, and stored in a desiccated environment at −20° C. For anchoring, cells were incubated in 200 μL of AcX at a concentration of 0.1 mg/ml in a 2-(N-morpholino)ethanesulfonic acid (MES)-based saline (100 mM MES, 150 mM NaCl) overnight at 4° C. Then, cells were washed with 1×PBS three times at RT for 5 minutes each.

Gelation solution which contains 1.1 M sodium acrylate (Sigma), 2 M acrylamide (Sigma), 90 ppm N,N'-methylenebisacrylamide (Sigma), 1.5 ppt ammonium persulfate (APS) (Sigma), and 1.5 ppt tetramethylethylenediamine (TEMED) (Sigma) in 1×PBS was prepared fresh. Cells were first incubated on ice for 10 min with shaking to prevent premature gelation and enable diffusion of solution into samples. A gelation chamber was prepared by placing two No. 1.5 coverslips on a glass slide spaced by about 8 mm to function as insulators on either end of the neuronal coverslip to avoid compression and each coverslip containing a neuronal cell culture sample was placed on a gelation chamber with the cells facing down. The gelation chamber was filled with gelation solution and a coverslip placed over the sample and across the two insulators to ensure the sample was covered with gelling solution and no air bubbles were formed on the sample. Samples incubated at 37° C. for 1 hours in a humidified atmosphere to complete gelation. Following gelation, the top coverslip was removed from the samples, and only the sample gel was transferred into a 1.5 mL tube containing 1 mL of denaturation buffer, consisting of 5% (w/v) sodium dodecyl sulfate (SDS), 200 mM NaCl, and 50 mM Tris at pH 8. Gels were incubated in denaturation buffer overnight at RT and 3 hour at 80° C., followed by washing in water overnight at RT to remove residual SDS. Gels were then stored in 1×PBS at 4° C. before immunostaining.

For immunostaining and imaging, gels were first incubated in bovine serum albumin (BSA) blocking solution that contains 1% BSA, 0.5% Triton-X in 1×PBS for 1 hour at RT then with primary antibodies overnight at 4° C. Gels were washed three times in BSA blocking solution for 30 minutes each at RT and incubated with fluorescently-labeled secondary antibodies overnight at 4° C. Gels were then washed three times in BSA blocking solution for 30 minutes each at RT and expanded in water overnight at 4° C. before imaging.

Fluorescence Microscopy of Immunostained Samples.

Fluorescence microscopy was performed on a spinning disk confocal microscope (a Yokogawa CSU-W1 Confocal Scanner Unit on a Nikon Eclipse Ti microscope) equipped with a 40× 1.15 NA water immersion objective (Nikon MRD77410), a Zyla PLUS 4.2 Megapixel camera controlled by NIS-Elements AR software, and laser/filter sets for 405 nm, 488 nm, 561 nm, and 640 nm optical channels. For each field of view, multi-channel volumetric imaging was performed at 0.4 μm per Z step. Imaging parameters were kept the same for all samples within a set of experiments (e.g., a set of 4-OHT induction experiments in which samples were treated with 4-OHT at different time points).

Antibodies and Nissl Stain.

The following antibodies and Nissl stain were used in certain studies described herein: primary antibodies, anti-HA (Santa Cruz, cat #sc-7392), anti-FLAG (Invitrogen, cat #740001), anti-V5 (Abcam, cat #ab9113), anti-NeuN (Synaptic Systems, cat #266004), anti-GFAP (Cell Signaling Technology, cat #12389), anti-Ibal (Wako Chemicals, cat #019-19741), anti-Synaptophysin (Sigma, cat #S5768), anti-Cleaved Caspase-3 (Cell Signaling Technology, cat #9664), anti-gH2AX (Millipore, cat #05-636), anti-Hsp70 (Cell Signaling Technology, cat #4872), anti-Hsp27 (Cell Signaling Technology, cat #2402); fluorescent secondary antibodies from Invitrogen, cat #A-21241, cat #A-21133, cat #A-32933, cat #A-32733, cat #A-11035, and cat #A-11073;

fluorescent secondary antibodies from Biotium, cat #20308; Nissl stain, NeuroTrace Blue Fluorescent Nissl Stain (Invitrogen, cat #N21479).

Fluorescence Microscopy of Live Cells and Immunostained Samples.

Fluorescence microscopy was performed on a spinning disk confocal microscope (a Yokogawa CSU-W1 Confocal Scanner Unit on a Nikon Eclipse Ti microscope) equipped with a 40× 1.15 NA water immersion objective (Nikon MRD77410), a 10× objective, a Zyla PLUS 4.2 Megapixel camera controlled by NIS-Elements AR software, and laser/filter sets for 405 nm, 488 nm, 561 nm, and 640 nm optical channels. For each field of view under 40× objective, multi-channel volumetric imaging was performed at 0.4 μm per Z step. Imaging parameters were kept the same for all samples within a set of experiments (e.g., a set of 4-OHT induction experiments in which samples were treated with 4-OHT at different time points).

RNA-Seq.

Figure 2A:
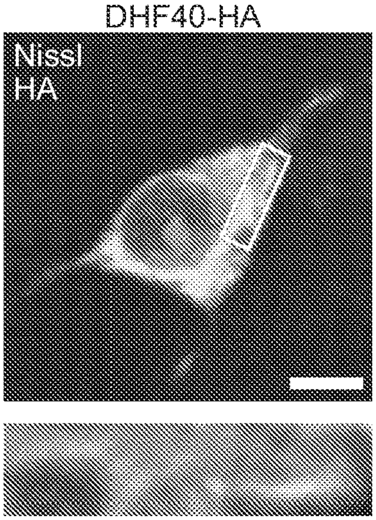
FIG. 2A-L provides images and graphs of results of analysis of XRI formation in neuron cultures and in mouse brains.
Figure 2B:
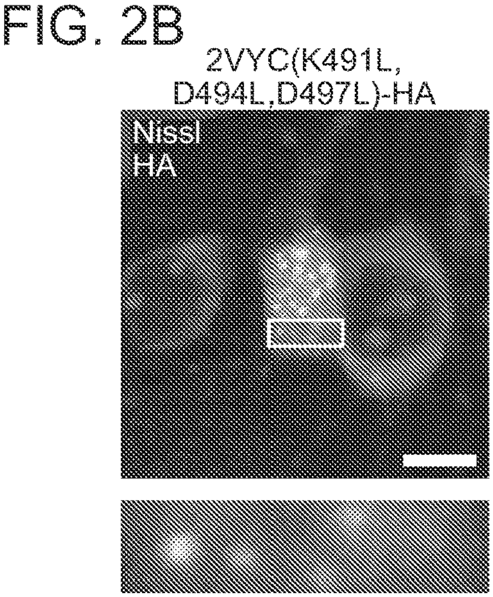
Figure 2C:
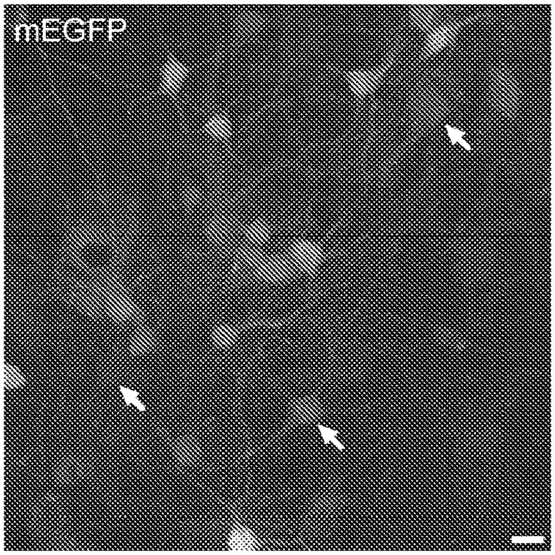
Figure 2D:
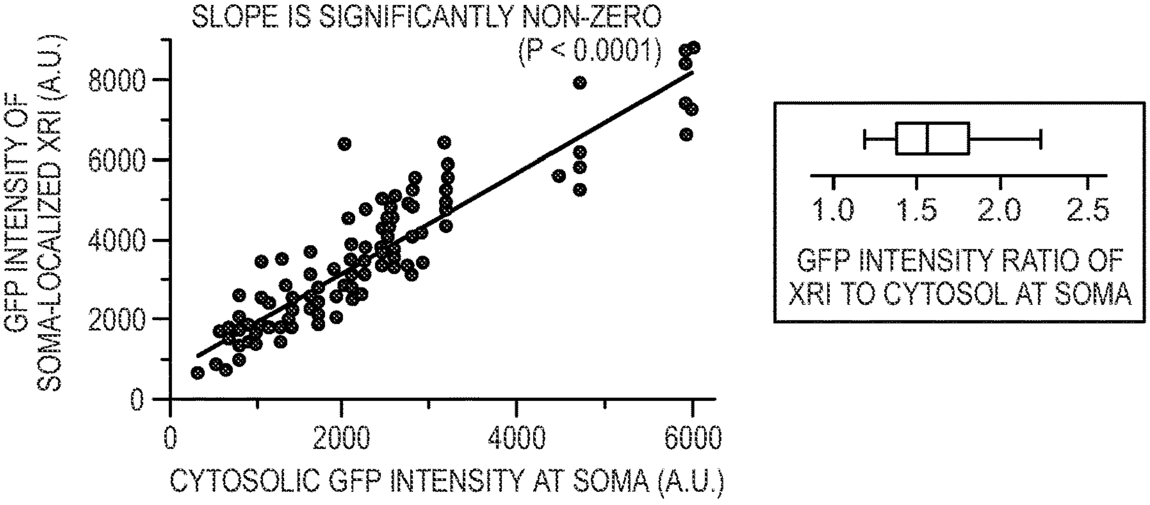
Figure 2E:
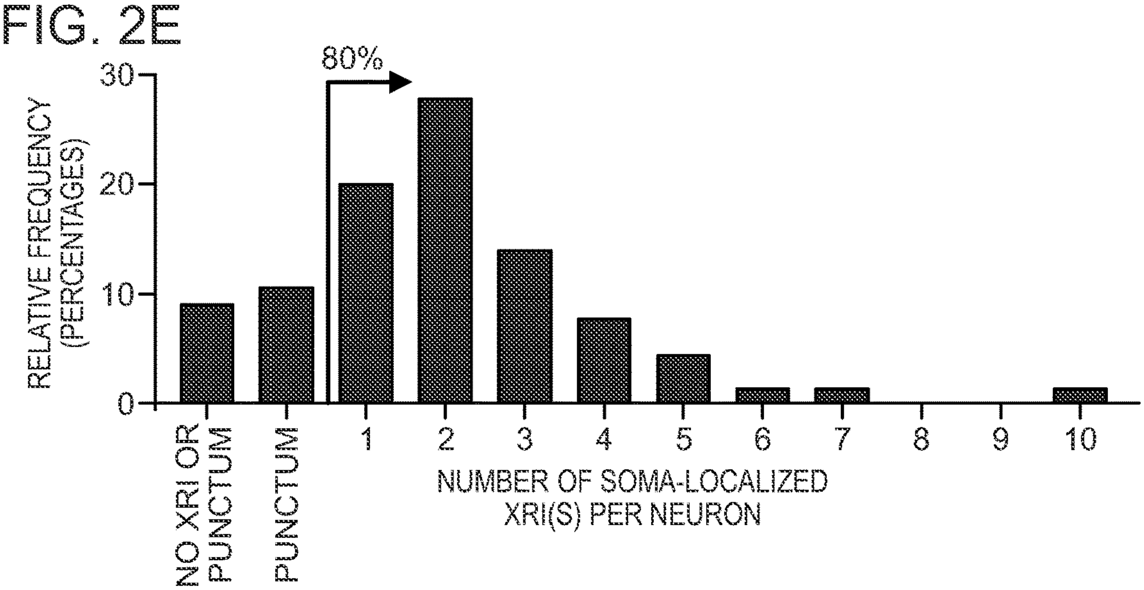
Figure 2F:
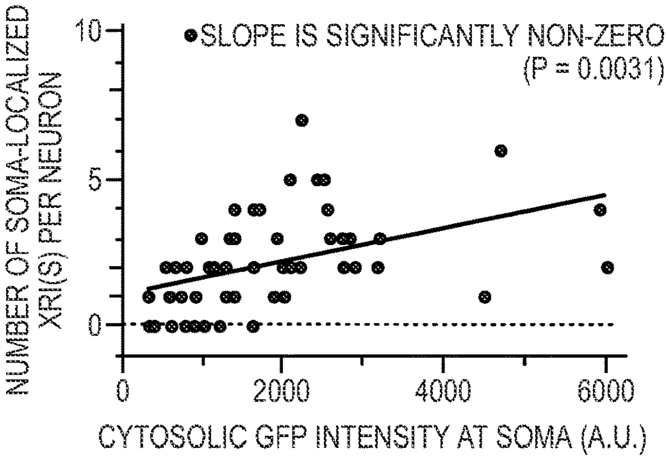
Figure 2G:
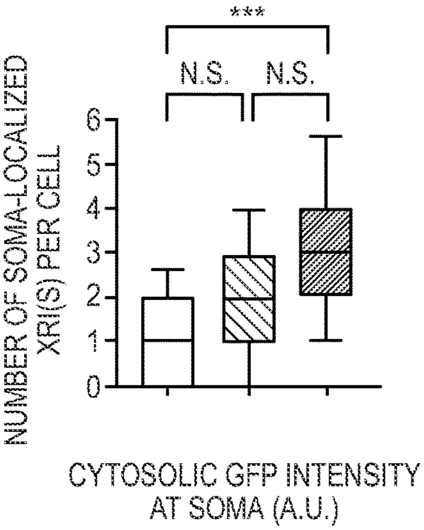
Figure 2H:
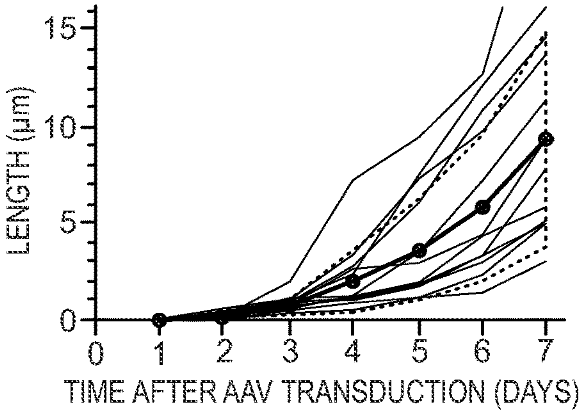

For studies with results shown in FIG. 2F-H, RNA was extracted from individual neuron cultures in 24-well plates with Trizol (Thermo Fisher) and purified with RNeasy Mini Kit (Qiagen). RNA quality was confirmed using a Femto Pulse system (Agilent). cDNA was generated from 2 ng of total RNA using the SMART-Seq v4 Ultra Low Input RNA Kit (Takara Bio) amplifying for 10 cycles and confirmed using a Fragment Analyzer (Agilent). 200 ng of amplified cDNA was prepared for Illumina sequencing by Nextera Flex (Illumina) using half volume reactions with 6 cycles of amplification. Final libraries were quantified on the Fragment Analyzer and by qPCR on a LC480 Light Cycler (Roche). Libraries were sequenced on a MiSeq (Illumina) using 75 nt paired end reads. Sequences were mapped to GRCm38 (mm10) reference genome (with gene annotations obtained from Ensembl). Gene expression raw counts were assessed by RSEM and then were normalized and batch-effect adjusted using DESeq2 [Love, M. I., et al., *Genome Biol.* 15, 1-21 (2014)], followed by differential expression analysis and statistics using DESeq2.

Image Analysis.

Image analysis was performed in ImageJ (ImageJ National Institutes of Health) and MATLAB (MathWorks).

Intensity Profile Measurements.

First, the somata of neurons in the images were identified by the Nissl staining (in samples without ExM) or anti-NeuN staining (in samples with ExM) channel, and XRI(s) in the soma of each neuron were identified by the anti-HA channel. If multiple XRIs were present in a soma, the XRI with the longest length as well as any XRI with length above half of that longest length was selected for downstream analysis. For each XRI, a curved centerline was drawn along the longitudinal direction of XRI in the anti-HA channel. The centerline width was set to half of the width of the XRI. The intensity profiles along this centerline with width were measured in the anti-HA channel (as HA line profile) and in other XRI epitope staining channels, such as in the anti-FLAG channel (as FLAG line profile) or anti-V5 channel (as V5 line profile).

Readout Information from Intensity Profiles.

For studies with results shown in FIG. 7, for the process flow of extracting information from the intensity profiles of XRIs. Step 1: For each XRI, a curved centerline was drawn along the longitudinal axis of the XRI in the anti-HA channel. The centerline width was set to half of the width of the XRI. Step 2: The intensity profiles along this centerline were measured in the anti-HA channel (resulting in an HA line profile) and in the other XRI epitope staining channel, such as in the anti-FLAG channel (resulting in a FLAG line profile) or in the anti-V5 channel (resulting in a V5 line profile). Step 3: Next, each of the line profiles was split into two half line profiles using the geometric center point of the XRI (the 50% length point along the centerline, measuring from the end of the XRI) as the 'split point'. Each of the half HA line profiles (H) was then converted into a line integrals of HA (H_integral) for every position (p) along the half XRI, by integrating the line profile with respect to the distance (d) along the half centerline starting from the split point (where d=0):

$$\text{H\_integral (p)} = \sum_{d=0}^{p} H(d)\cdot\Delta d$$

Then these line integrals of HA were normalized to the maximum integral value (integral from the split point (d=0) to the end of XRI (d=End)) so that each line integral of HA started at the value 0 at the geometric center point of the XRI, and gradually increased to the value 1 at the end of the XRI. We define this quantity as the 'fraction of HA intensity line integral (H_fraction_integral)':

$$\text{H\_fraction\_integral (p)} = \sum_{d=0}^{p} H(d)\cdot\Delta d \Big/ \sum_{d=0}^{End} H(d)\cdot\Delta d$$

For the corresponding half FLAG (or V5) line profiles (F), line integrals (F_integral) were also calculated but not normalized:

$$\text{F\_integral (p)} = \sum_{d=0}^{p} F(d)\cdot\Delta d$$

At this point, the line integrals of HA and FLAG (or V5) had been identified, which corresponded to the cumulative HA and FLAG (or V5) intensities along each half of the XRI. The line integrals of FLAG (or V5) line profiles were then converted from the position axis (p) into the axis of the fraction of HA intensity line integral (H_fraction_integral) via variable substitution from p to H_fraction_integral (p):

$$\text{F\_integral(p)} \xrightarrow[\text{substitution}]{\text{variable}} \text{F\_integral(H\_fraction\_integral)}$$

The FLAG (or V5) intensity change per unit change in the cumulative HA intensity, defined as the FLAG (or V5) signal (F_signal), was calculated by taking the derivative of the line integral of FLAG (or V5) with respect to the fraction of HA intensity line integral:

$$\text{F\_signal (H\_fraction\_integral)} = \frac{\Delta\ \text{F\_integral (H\_fraction\_integral)}}{\Delta\ \text{H\_fraction\_integral}}$$

At this stage, the line integral of HA and the FLAG (or V5) signal was obtained from each of the halves of the XRI, and the final extracted FLAG (or V5) signal from this XRI was defined as the point-by-point average of the two FLAG (or V5) signals from the two halves of the XRI. Step 4: the two obtained FLAG (or V5) signals from the same XRI were found to have small but noticeable differences. It was determined that such small but noticeable discrepancies between the two halves of the same XRI were due to the asymmetry of the XRI, and the choice of the exact geometric center as the split point may not be optimal. To minimize the discrepancy between the two FLAG (or V5) signals from the two halves of the same XRI, a search was performed to identify an optimal split point near the geometric center of the XRI (searching range was the geometric center +/−10% of the total XRI length), so that using this optimal split point, instead of the geometric center, as the split point results in the least difference (in sum of squared differences) between the two FLAG (or V5) signals from the two halves of the splitted XRI. Step 5: Same as Step 3, except that the optimal split point, instead of the geometric center, was used to split the intensity profiles into two halves. The resulting final FLAG (or V5) signal (after averaging those from the two halves) when using the geometric center as the split point was found to be similar to that when using the optimal split point as the split point. Nevertheless, the optimal split point was used as the split point to analyze XRIs throughout studies described herein.

Calculation of the Fraction of HA Line Integral when FLAG Signal Begins to Rise.

The FLAG signal minus the FLAG signal at the center of XRI (i.e., the optimal split point as defined above) was plotted against the fraction of HA line integral. The initial rising phase of the FLAG signal (defined as the portion of the FLAG signal between 10% to 50% of the peak FLAG signal) was fitted as a linear function, which was then extrapolated onto the axis of the fraction of HA line integral. The intersection point at the axis of the fraction of the HA line integral was defined as the fraction of HA line integral when the FLAG signal began to rise.

Statistical Analysis.

All statistical analysis was performed using the built-in statistical analysis tools in Prism (GraphPad) or MATLAB, except for the statistical analysis of the RNA-Seq data, which was performed using DESeq2. The statistical details of each statistical analysis can be found in the figure descriptions provided elsewhere herein, except for the statistical details of the RNA-Seq data.

Results

Figure 1C:
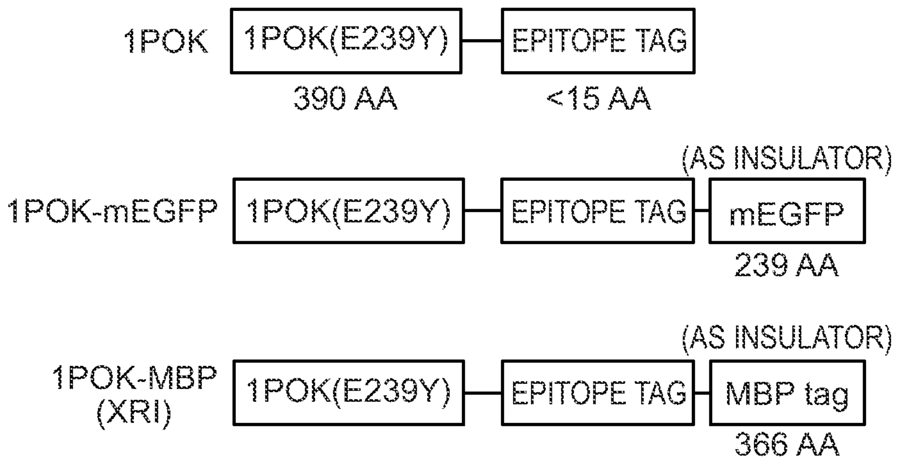
Figure 1D:
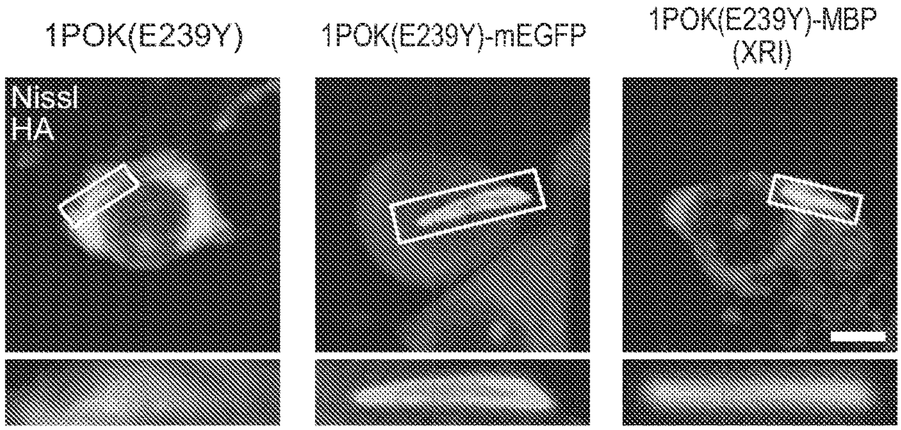

Initial studies were performed to test if human-designed proteins known to self-assemble into filaments, could be coaxed to reliably form continuously growing linear chains in cultured mammalian cells. In the studies 14 human-designed filament-forming proteins (previously characterized in buffers, bacteria, and yeast) were fused to a short epitope tag (HA, for immunofluorescence imaging after protein expression and cell fixation) and expressed in primary cultures of mouse hippocampal neurons (see Table 1 for sequences of the motifs; see Table 2 for all tested constructs). Upon immunofluorescence staining, followed by imaging under confocal microscopy, two filament-forming proteins produced clear and stable fiber-like structures in the cytosol: 1POK(E239Y), a human-engineered filament-forming protein based on an *E. coli* isoaspartyl dipeptidase (Garcia-Seisdedos, et al. *Nature* 548, 244 (2017); FIG. 1C-D), and DHF40, a computationally designed filament-forming protein (Shen, H. et al. *Science* 362, 705 (2018); FIG. 2A). The rest of the proteins produced unstructured aggregates, high non-assembly background, and/or punctum-like structures in neurons (see FIG. 2B for example; see Table 2 for complete screening results). However, both filament-forming proteins also produced unstructured aggregates of protein in the cytosol. DHF40 showed a higher immunofluorescence background in cytosolic areas, which did not correspond either to fiber-like structures or unstructured aggregates, than did 1POK(E239Y), suggesting DHF40 had a higher level of free-floating protein monomers that did not bind to the protein assembly, than did 1POK (E239Y). Due to the lower immunofluorescence background, we selected 1POK(E239Y) as the filament forming protein for further engineering in this study.

Figure 1E:
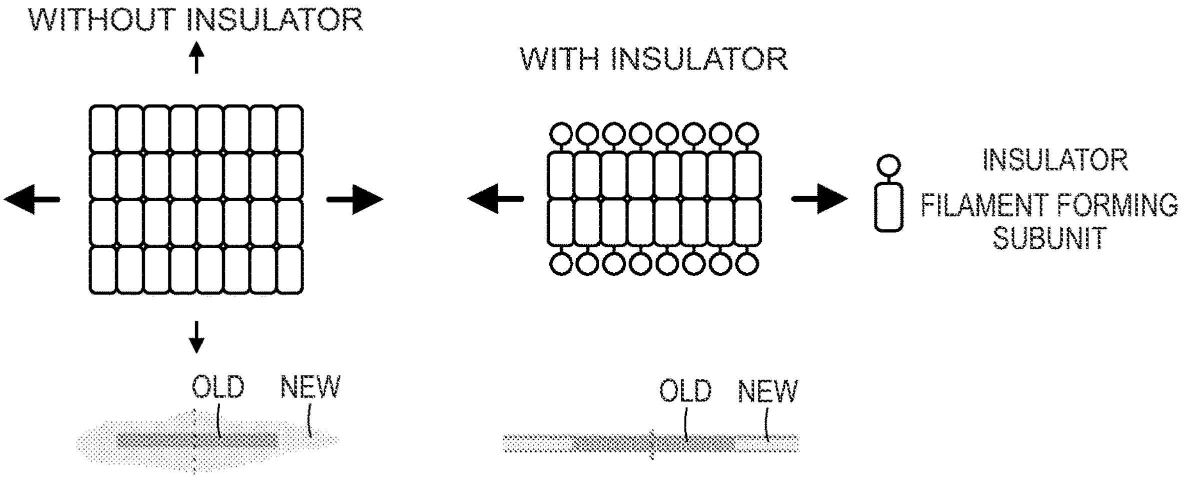

Because linear protein assembly would enable useful information encoding that could then be easily read out, next protein engineering was performed on 1POK to reduce the unstructured aggregates in cells. It was reasoned that unstructured aggregates could be present due to unwanted lateral growth (FIG. 1E, left), as opposed to the longitudinal growth that would result in linear information encoding, and that reducing such lateral growth would discourage the formation of unstructured aggregates and thus encourage fiber-like linear protein assembly (FIG. 1E, right). It was determined that by fusing a filament "insulator" component to the lateral edge of the filament forming monomer, unwanted lateral binding and growth of the protein assembly were sterically blocked. Highly monomeric proteins that are widely used in bioengineering, mEGFP [Cranfill, P. J. et al. *Nat. Methods* 2016 137 13, 557-562 (2016)] (a green fluorescent protein) and maltose binding protein (MBP tag; an *E. coli* protein commonly used as a solubility tag for recombinant protein expression in mammalian [Reuten, R. et al. *PLoS One* 11, e0152386 (2016)] and non-mammalian [Kapust, R. B. & Waugh, D. S. *Protein Sci.* 8, 1668-1674 (1999)] cells) were fused to 1POK as insulators, together with the short epitope tag HA (FIG. 1C). Monomeric proteins were chosen as insulators because so it was expected that any homo-oligomeric binding of non-monomeric proteins might encourage, rather than halt, unwanted lateral binding and growth of the protein assembly. Expression of these variants in mouse neurons showed that both produced only fiber-like structures, without any unstructured aggregates (FIG. 1D).

Figure 1F:
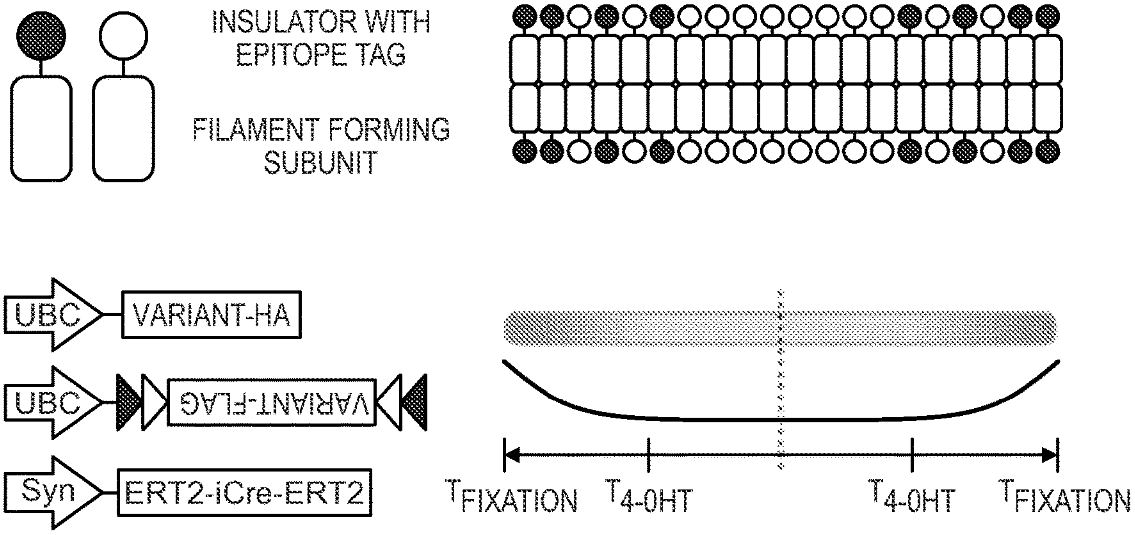
Figure 1G:
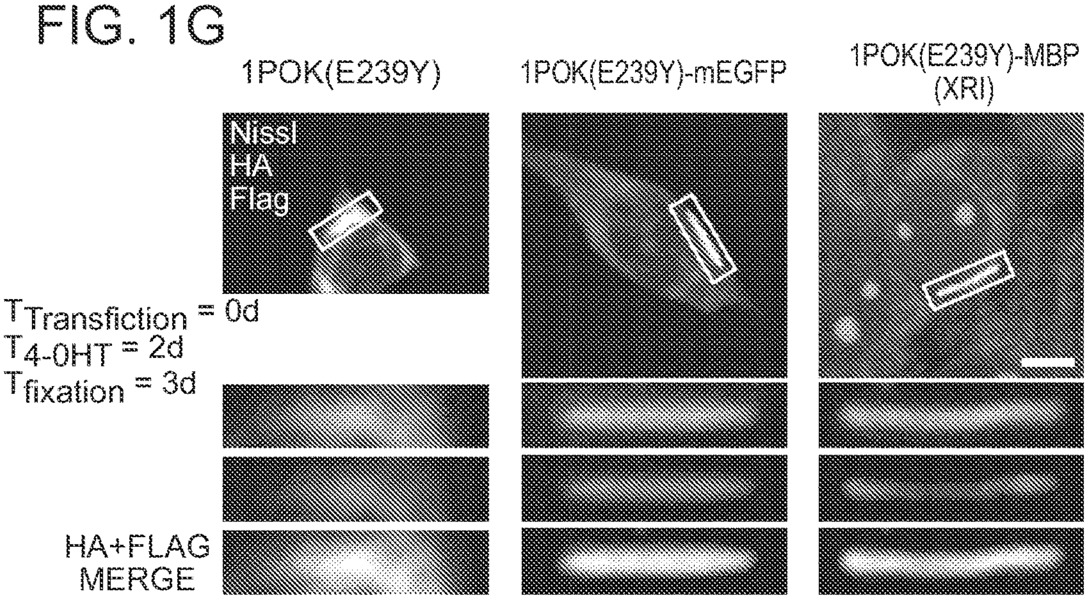

Next, studies were performed that tested if the mEGFP or MBP tag-bearing variants could encode information along their linear extent while preserving temporal order of the information along their corresponding protein assemblies. If protein monomers with, say, the epitope tag HA are constantly expressing, and the expression of protein monomers with, say, the epitope tag FLAG are induced at a specific time point, then at that time point, monomers with the FLAG tag will be more common, and thus preferentially added over those containing HA, along the growing protein chain; then, the period of time at which FLAG is expressed could be easily read out via immunostaining against both HA and FLAG tags (FIG. 1F). In certain studies the ERT2-iCre-ERT2 based chemically inducible Cre system [Matsuda, T., & C. L. Cepko *Proc. Natl. Acad. Sci. U.S.A.* 104, 1027-1032 (2007)] was used to activate the expression of protein monomers with the FLAG tag, in a Cre-dependent FLEX vector, by 4-hydroxytamoxifen (4-OHT) treatment at defined times (FIG. 1F). Co-expressing these two vectors, both driven by the constitutive human ubiquitin (UBC) promoter, with a continuously expressed HA-bearing monomer in mouse neurons via DNA transfection, and then treating the neurons with 4-OHT for 15 minutes at a time point 2 days after transfection, was followed by fixing the neurons 1 day later, followed in turn by processing for immunofluorescence. This experiment was performed for each of the three variants, 1POK, 1POK-mEGFP, and 1POK-MBP (FIG. 1G). For the original 1POK variant without the insulator (FIG. 1G, left), results indicated a high similarity between the immunofluorescence patterns of the HA tag and the FLAG tag, showing that the 1POK variant could not preserve the temporal order of the protein monomers expressed, as had been hypothesized (FIG. 1E). For the 1POK-mEGFP variant (FIG. 1G, middle), results indicated a high similarity between the immunofluorescence patterns of the HA tag and FLAG tag. It was thought this might be due to the existence of a small but non-negligible unwanted lateral growth in this variant, so newly expressed FLAG-fused monomers coated the lateral boundaries of the entire fiber assembly, resulting in uniform immunofluorescence of the FLAG tag along the assembly. For the 1POK-MBP variant, results indicated the immunofluorescence of the HA tag showed a continuous intensity profile along the protein assembly (FIG. 1G, right), while that of the FLAG tag showed higher intensity towards the two ends of the protein assembly and lower intensity towards the center of the protein assembly, a polarized pattern. Thus, the 1POK-MBP variant showed a pattern that preserved temporal information created by the triggering of the FLAG tag at a defined point in time. This variant was named the XRI, going forward throughout the rest of the experimental studies disclosed herein.

Figure 1H:
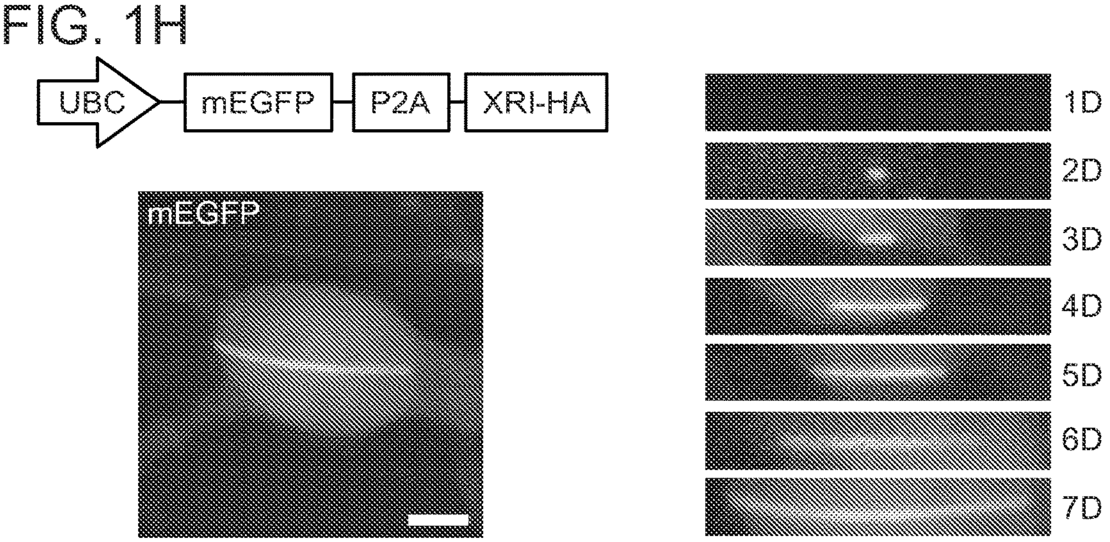
Figure 1I:
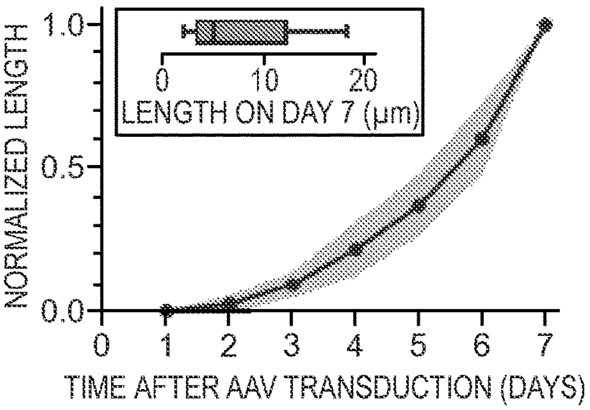
Figure 1J:
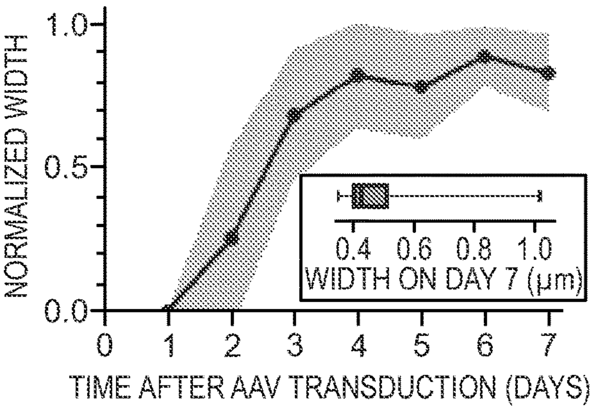
Figure 2I:
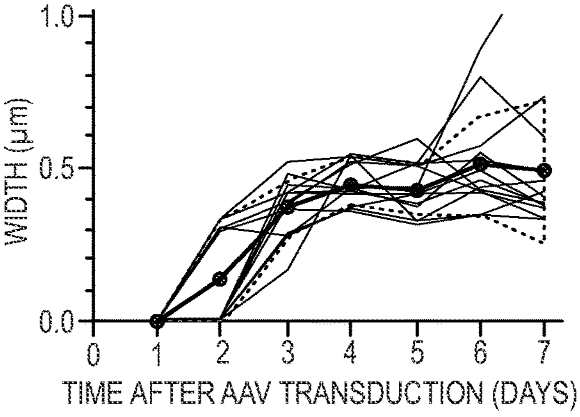
Figure 2J:
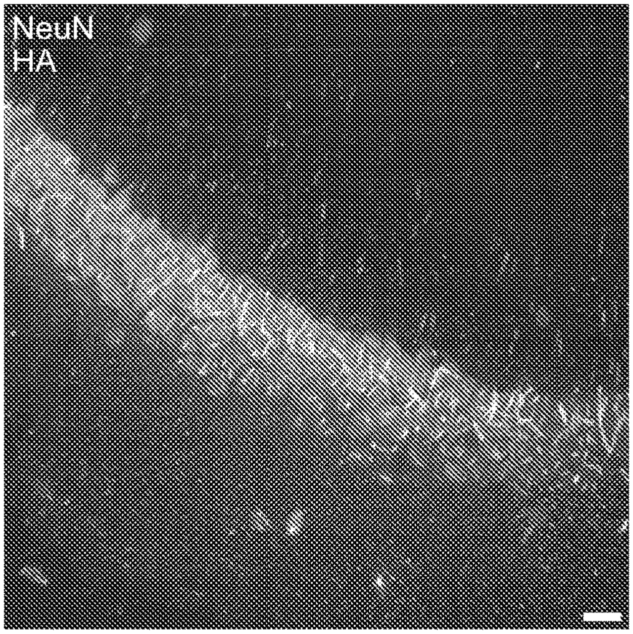
Figure 2K:
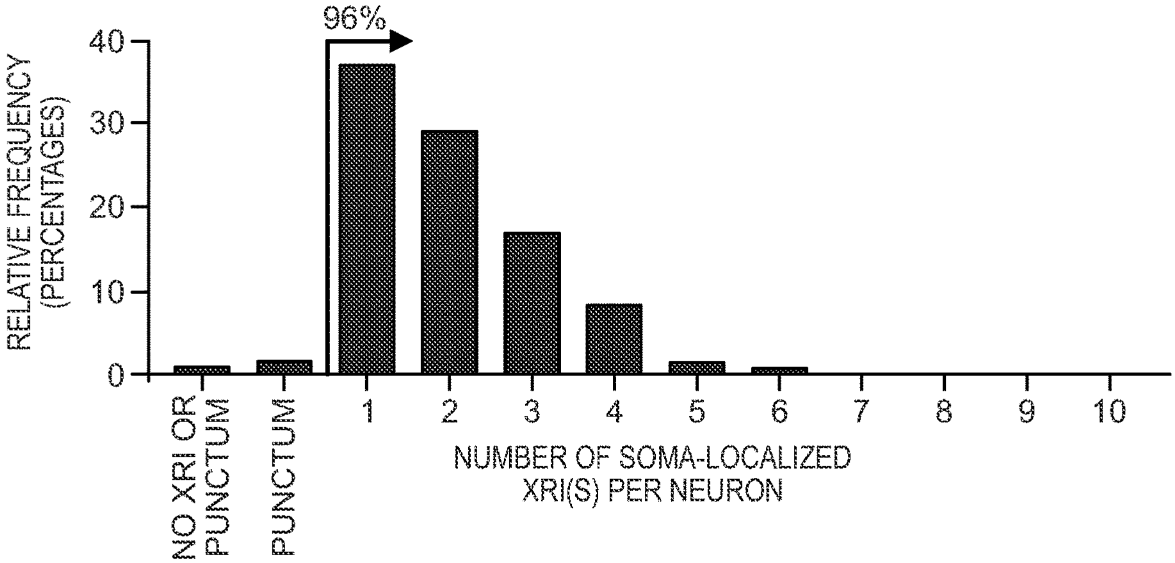
Figure 2L:
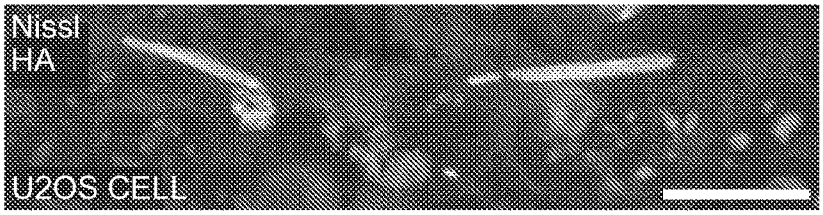
Figure 3A:
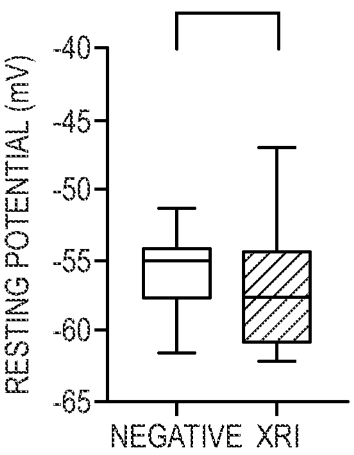
FIG. 3A-H provides plots of results from studies including electrophysiology and RNA-Seq analysis of cultured neurons expressing XRI.
Figure 3B:
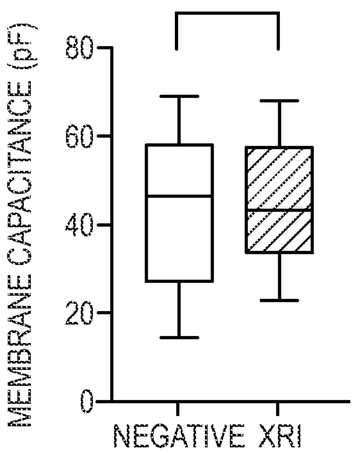
Figure 3C:
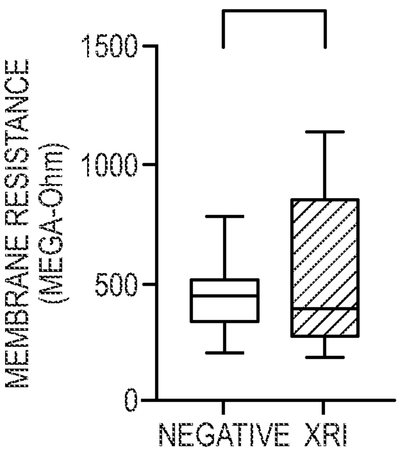
Figure 3D:
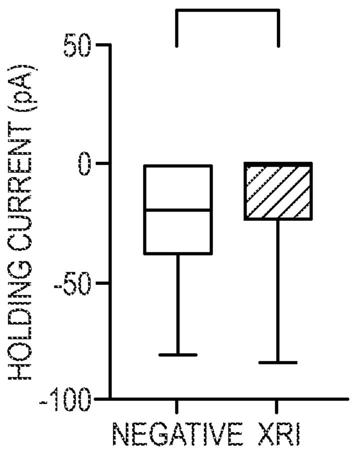
Figure 3E:
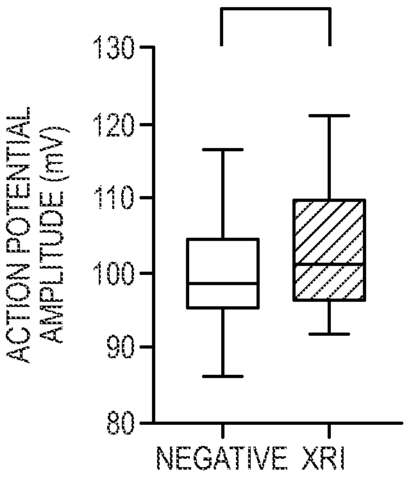
Figure 3F:
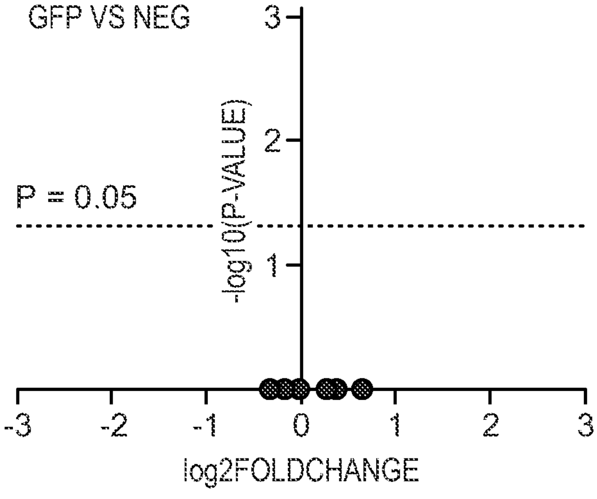
Figure 3G:
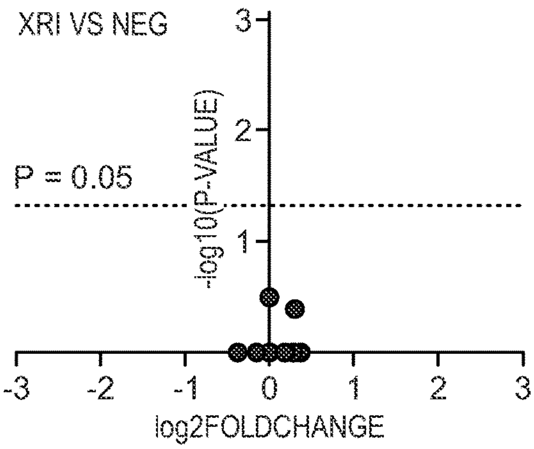
Figure 3H:
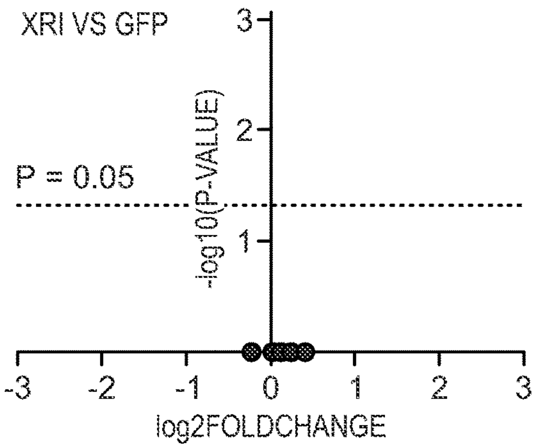
Figure 4A:
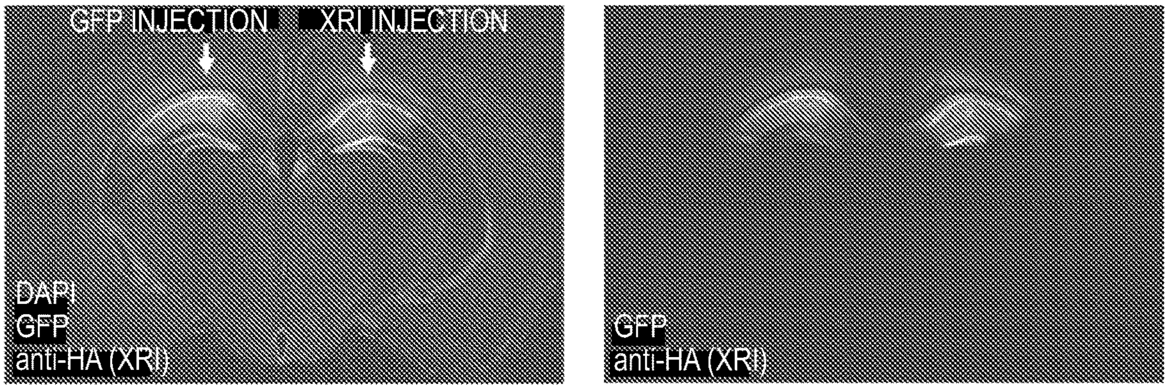
FIG. 4A-I provides images and graphs of results of immunohistochemical characterization of cellular and synaptic state markers in mouse brains expressing XRI.
Figure 4B:
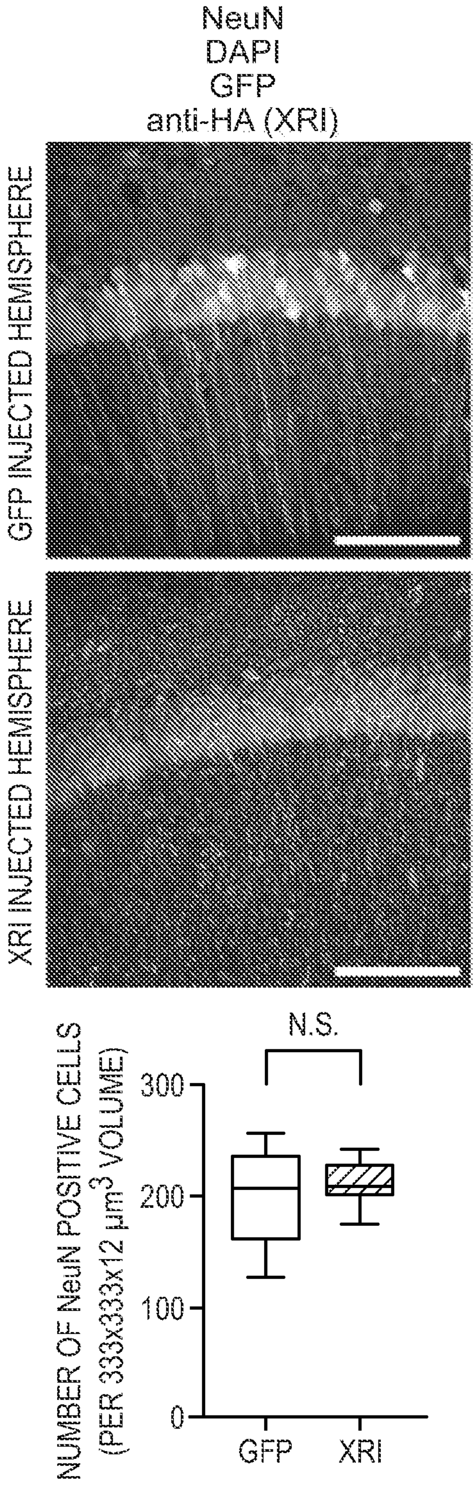
Figure 4C:
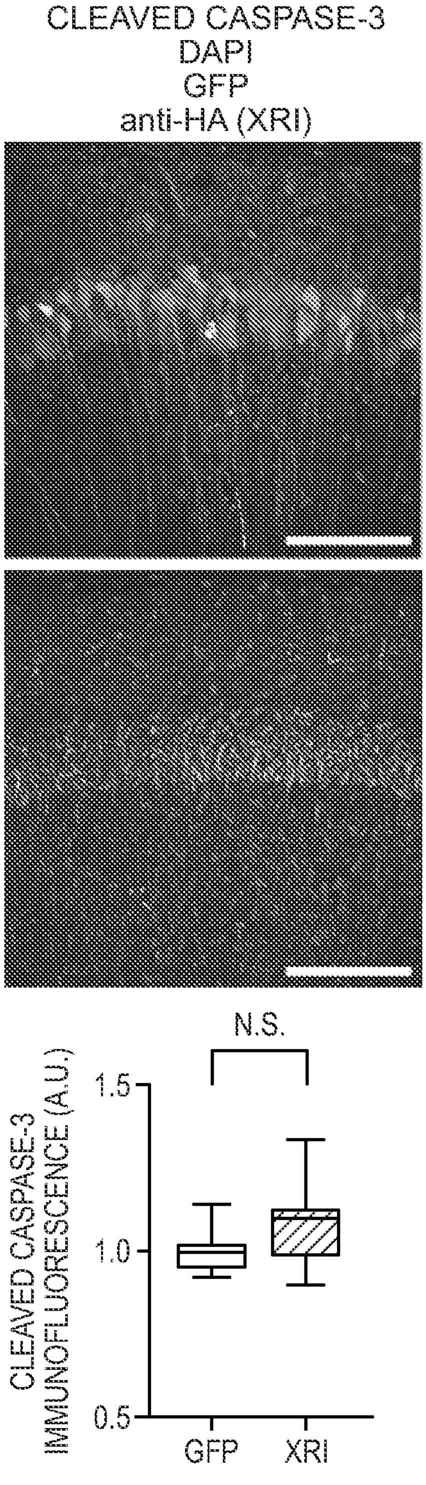
Figure 4D:
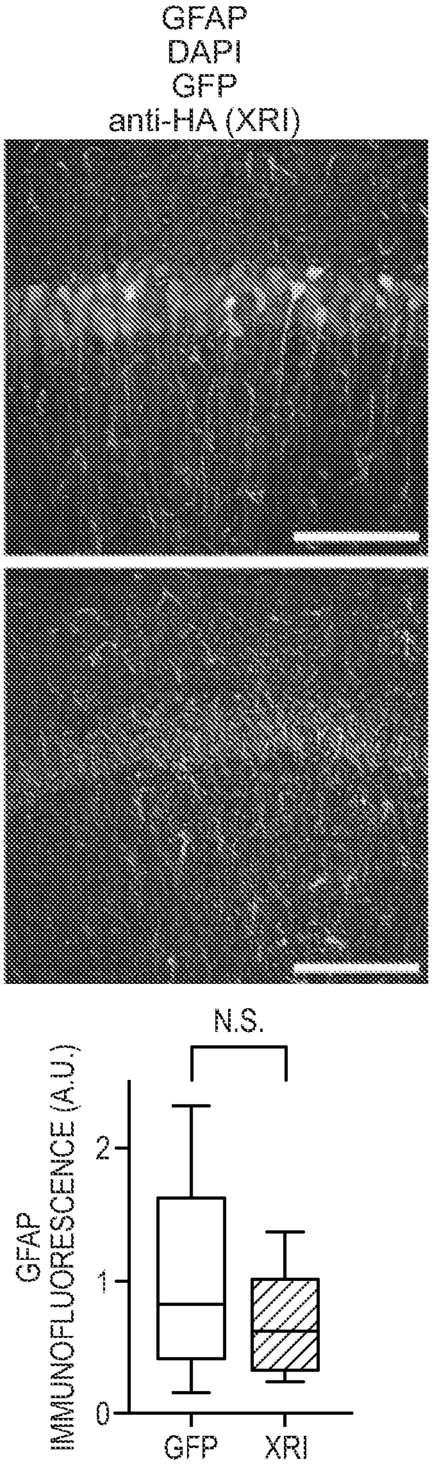
Figure 4E:
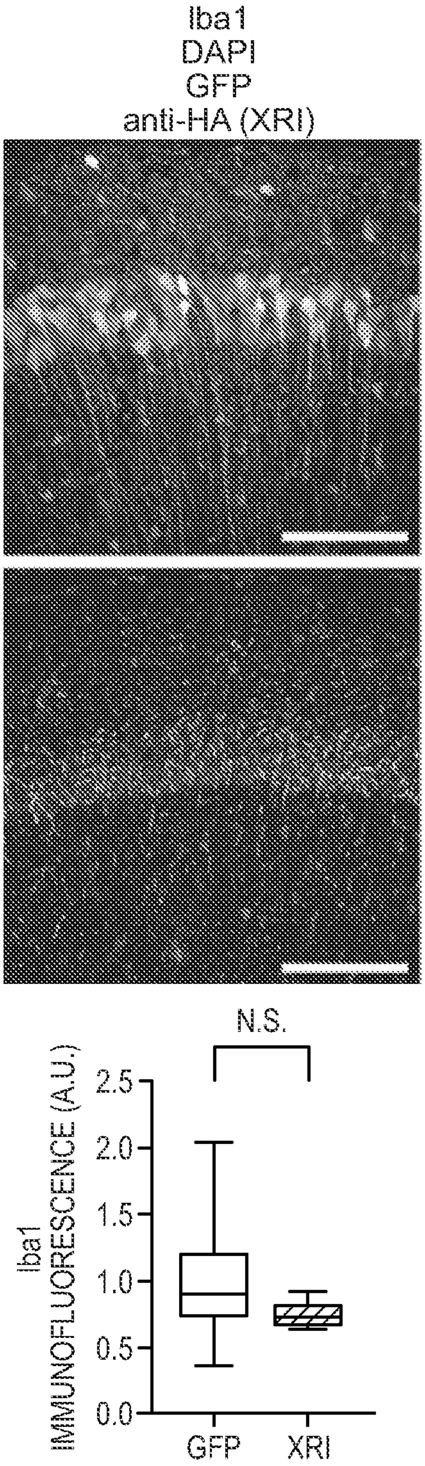
Figure 4F:
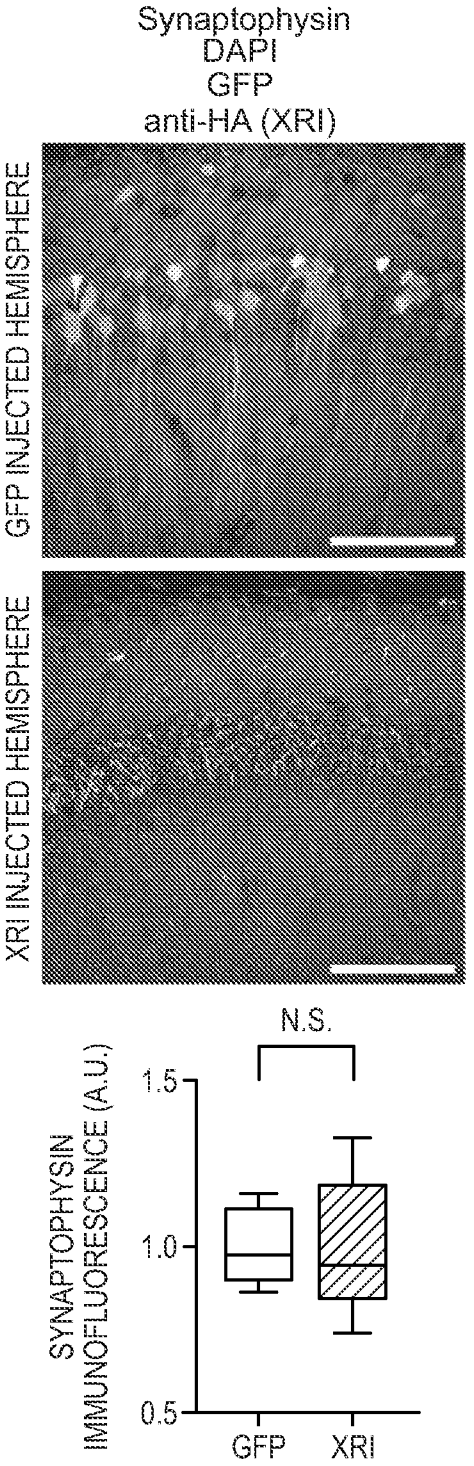
Figure 4G:
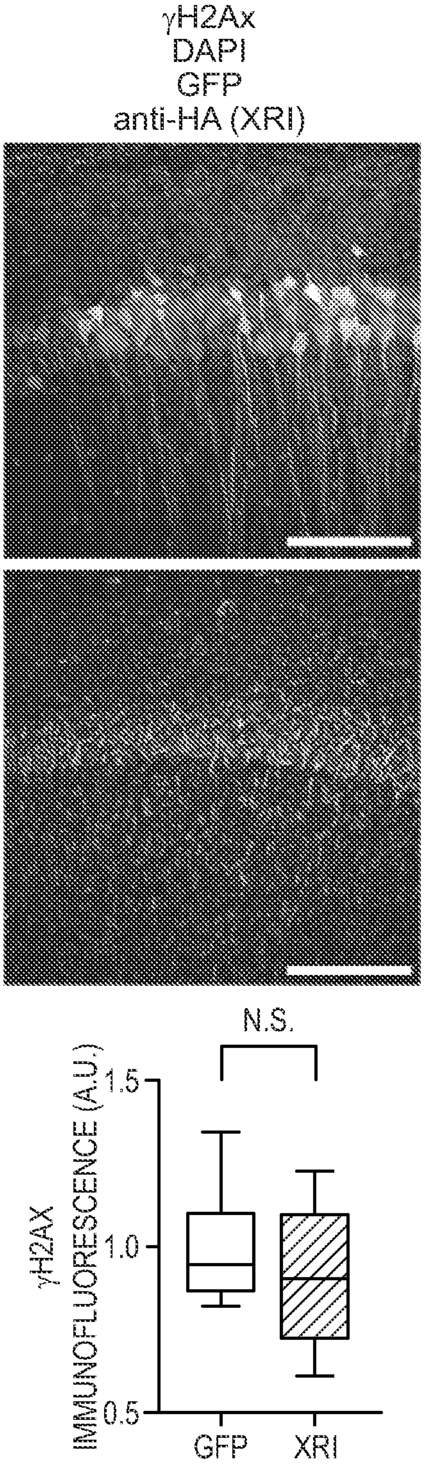
Figure 4H:
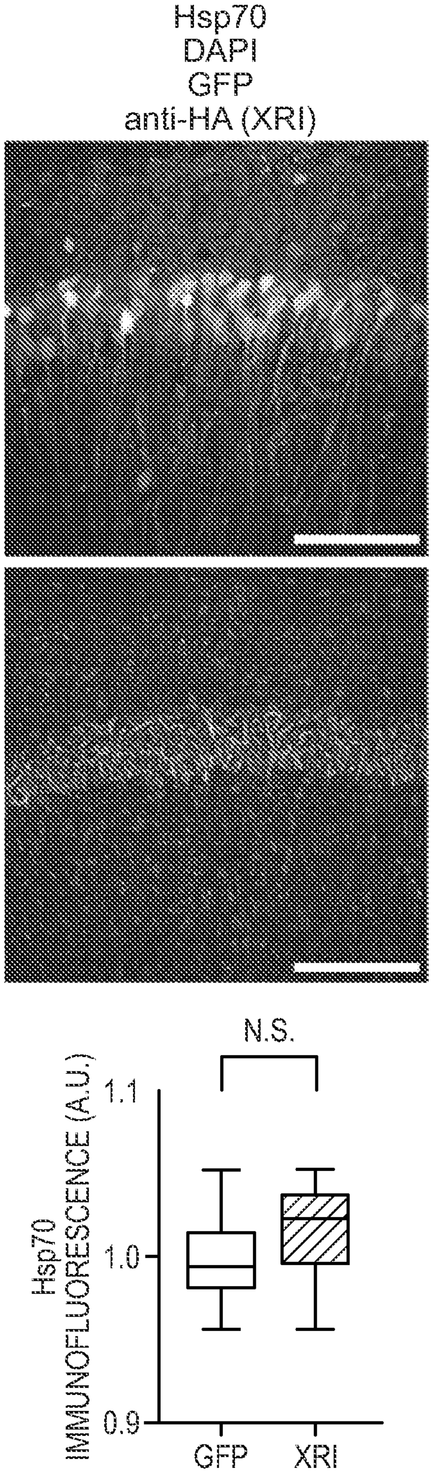
Figure 4I:
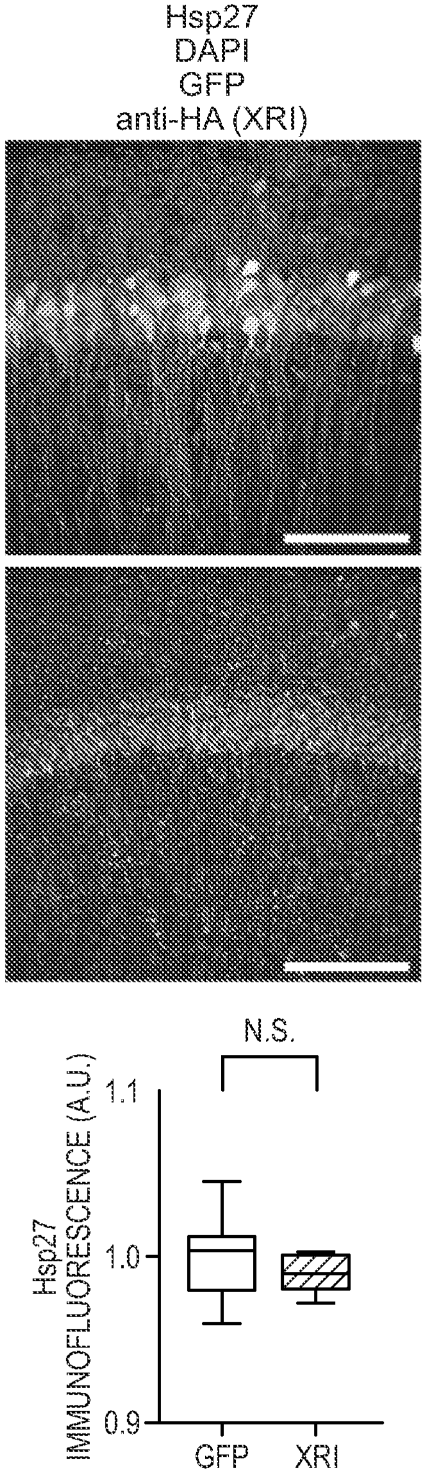

In order to characterize the electrophysiological integrity of neurons expressing XRIs, a bicistronic adeno-associated virus (AAV) construct was prepared, that contained mEGFP-P2A-XRI-HA, where P2A is a well-known self-cleaving peptide [Kim, J. H. et al. *PLoS One* 6, e18556 (2011)] (FIG. 1H, upper left, schematic), so that cells expressing XRI could be identified by their GFP fluorescence, for patch clamping. Surprisingly, transduction of this bicistronic construct into cultured neurons resulted in not only mEGFP expression in the cytosol, but also a small amount of mEGFP decorating the XRI (FIG. 1H, lower left). The fluorescence intensity of mEGFP-decorated XRI in the GFP channel was dim, only about 60% higher than that of the non-XRI-occupied cytosol at the soma (FIG. 2C-D). It was reasoned that such slight XRI labeling by mEGFP was due to the self-cleaving efficiency of P2A being less than 100% (about 90% in mammalian cells) [Kim, J. H. et al. *PLoS One* 6, e18556 (2011)], resulting in a small population of XRI monomers carrying mEGFP, resulting in the presence of a sparse amount of mEGFP on the XRI assembly. Of GFP-positive neurons (i.e., those with effective AAV-mediated gene delivery), about 80% had clear XRI formation at the soma 7 days after AAV transduction, with typically 1-4 XRIs at the soma (FIG. 2E). Out of the remaining 20% of neurons that had no clear XRI formation at the soma, about half had punctum-like structures that did not have clear, elongated shape of typical XRIs, and the other half had no resolvable structures (see the image of representative neurons in FIG. 2C indicated by arrows). Using the cytosolic GFP intensity as an estimation of the expression level of the overall mEGFP-P2A-XRI bicistronic construct, it was found that neurons with higher cytosolic GFP intensities had a significantly larger number of XRIs formed, and that neurons had unsuccessful XRI formation (of any shape) at very low cytosolic GFP intensities (FIG. 2F-G). These results suggest that reliable XRI formation requires a sufficient expression level of XRI. The AAV of XRI-HA (without mEGFP) was also injected into the CA1 region of the mouse hippocampus and, after immunofluorescent staining of the HA tag and imaging, and it was determined that 96% of CA1 neurons in the injected region had clear, successful XRI formation at the soma, 14 days post AAV injection, with typically 1-4 XRIs at the soma (FIG. 2J-K).

This bicistronic AAV construct was then used to track XRI formation over time in live neurons, by imaging the GFP fluorescence in the same neurons daily for 7 days post AAV transduction (FIG. 1H, right). It was observed that XRI elongation during the 7 days was at a slightly increasing rate over time (FIG. 1I, normalized length of XRI versus time; FIG. 2H, absolute length of XRI versus time). It was also observed that the width of XRI increased during days 1-3 post AAV transduction, reaching a constant level from day 3 onwards (FIG. 1J, normalized width of XRI versus time; FIG. 2I, absolute width of XRI versus time), raising the question of whether the blockage of lateral growth has a stochastic component that takes a few days to stabilize. Consistent with this initial stochasticity, it was observed that no XRI structures appeared on day 1, about half of the XRIs appeared on day 2, and the remaining half appeared on day 3, post AAV transduction (FIG. 2I), and that before day 3 the XRIs were very short, at less than 10% of their lengths on day 7 post AAV transduction (FIG. 2H). These observations suggested that the XRI system might only stabilize, and be able to record temporal information, starting around day 3 post AAV transduction (explored in experiments described below herein).

Next, electrophysiology and RNA-Seq analysis of cultured neurons expressing XRI was performed and it was observed that XRI expression did not alter the electrophysiology and endogenous gene expression in these neurons (FIG. 3). Immunohistochemical characterization of mouse brains expressing XRI was also performed and results showed XRI expression in cell populations in vivo did not alter cellular and synaptic state markers, including NeuN as a neuronal marker, cleaved Caspase-3 as an apoptotic marker, GFAP as an astrocyte marker, Ibal as a microglial marker, Synaptophysin as a synaptic protein marker, γH2AX as a DNA damage marker, and Hsp70 and Hsp27 as cell physiological stress markers (FIG. 4). Because the primary focus of the studies was to develop and apply recording systems in post-mitotic cells such as neurons, experiments did not focus on XRI usage in dividing cells, but it was noted that expression of the current XRI in dividing cells encountered difficulty (FIG. 2L), with XRI-like structures forming, but accompanied by aggregate-like structures. Thus, experiments retained a focus on non-dividing cells, neurons.

Figure 5A:
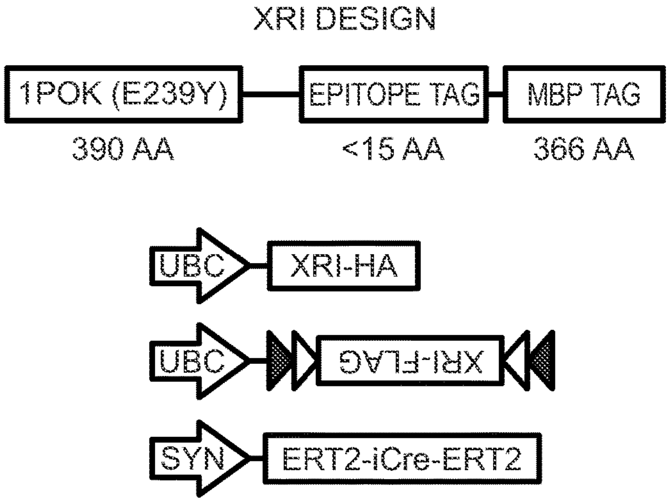
FIG. 5A-H provides schematics, images, and graphs of results of characterization and calibration of XRIs via timed chemically induced expression.
Figure 5B:
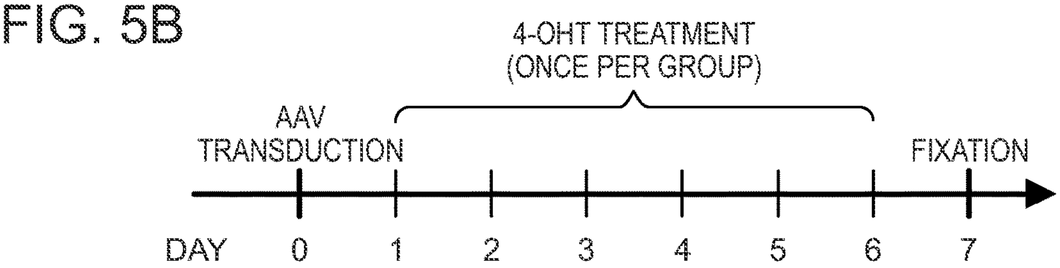
Figure 5C:
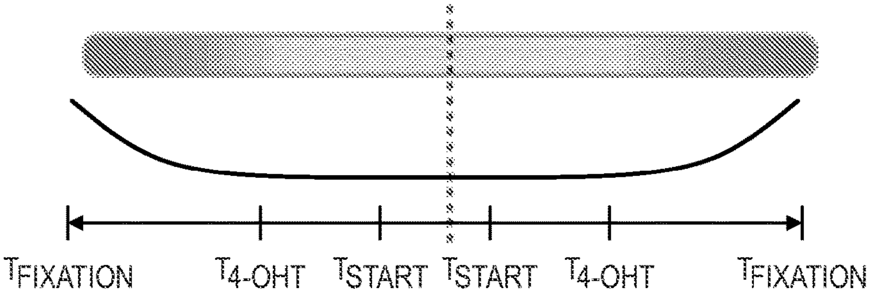
Figure 5D:
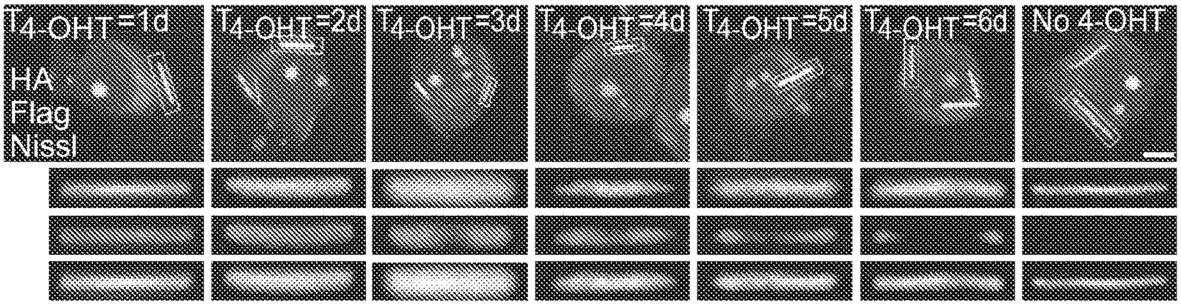
Figure 5E:
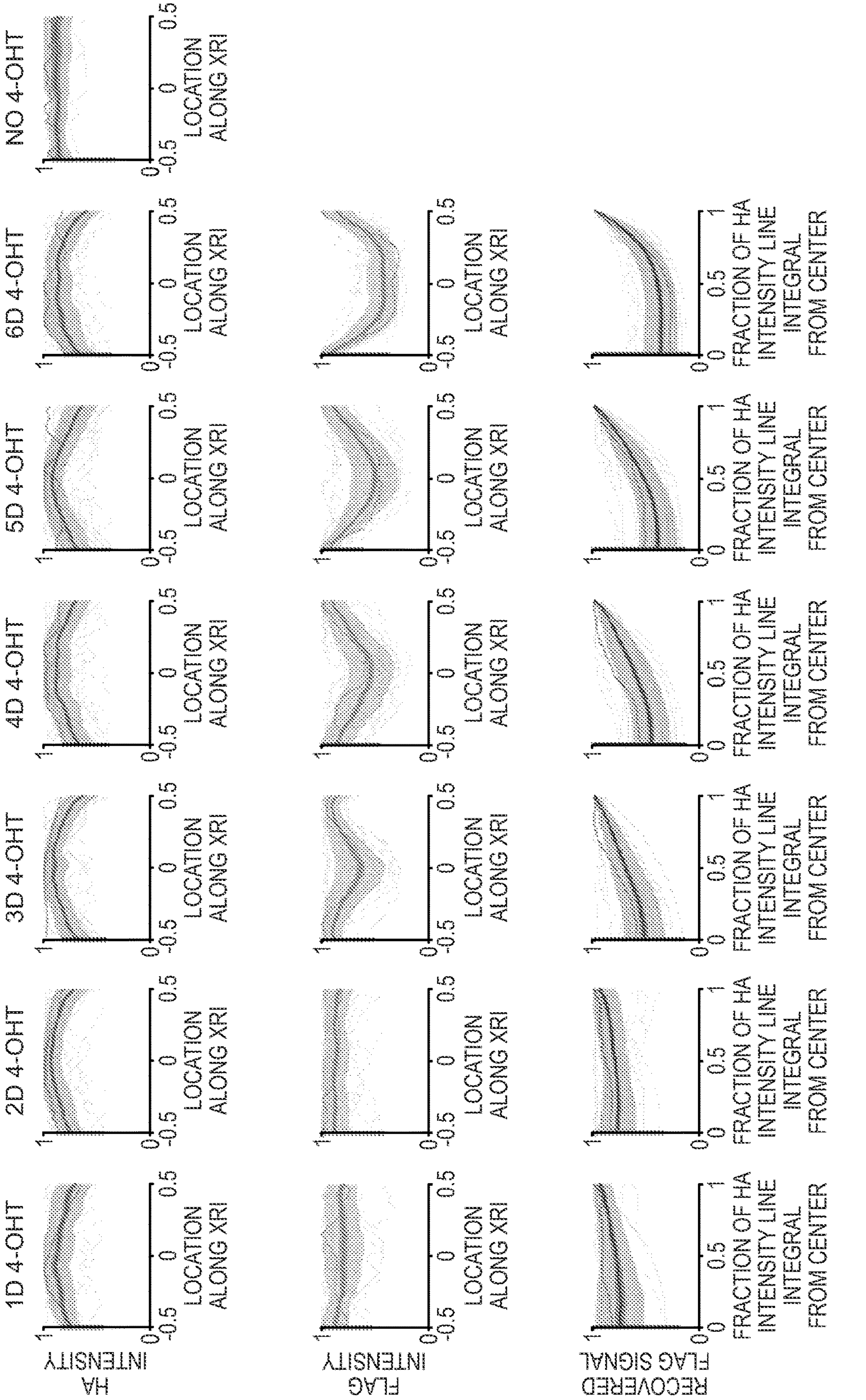
Figure 5F:
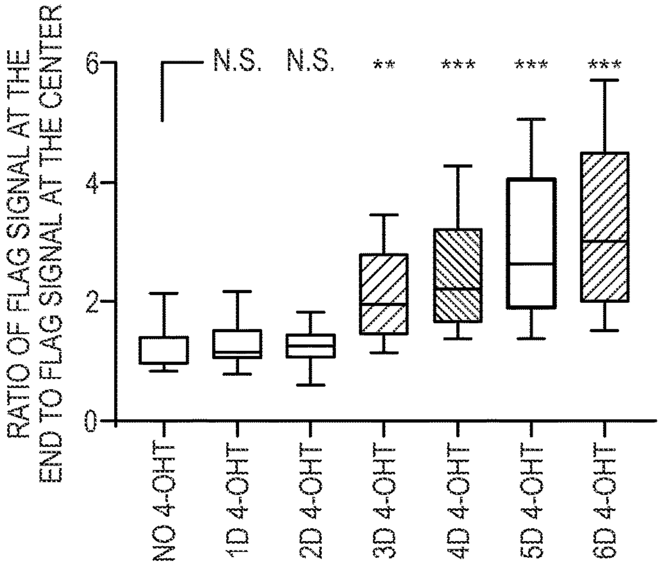
Figure 6A:
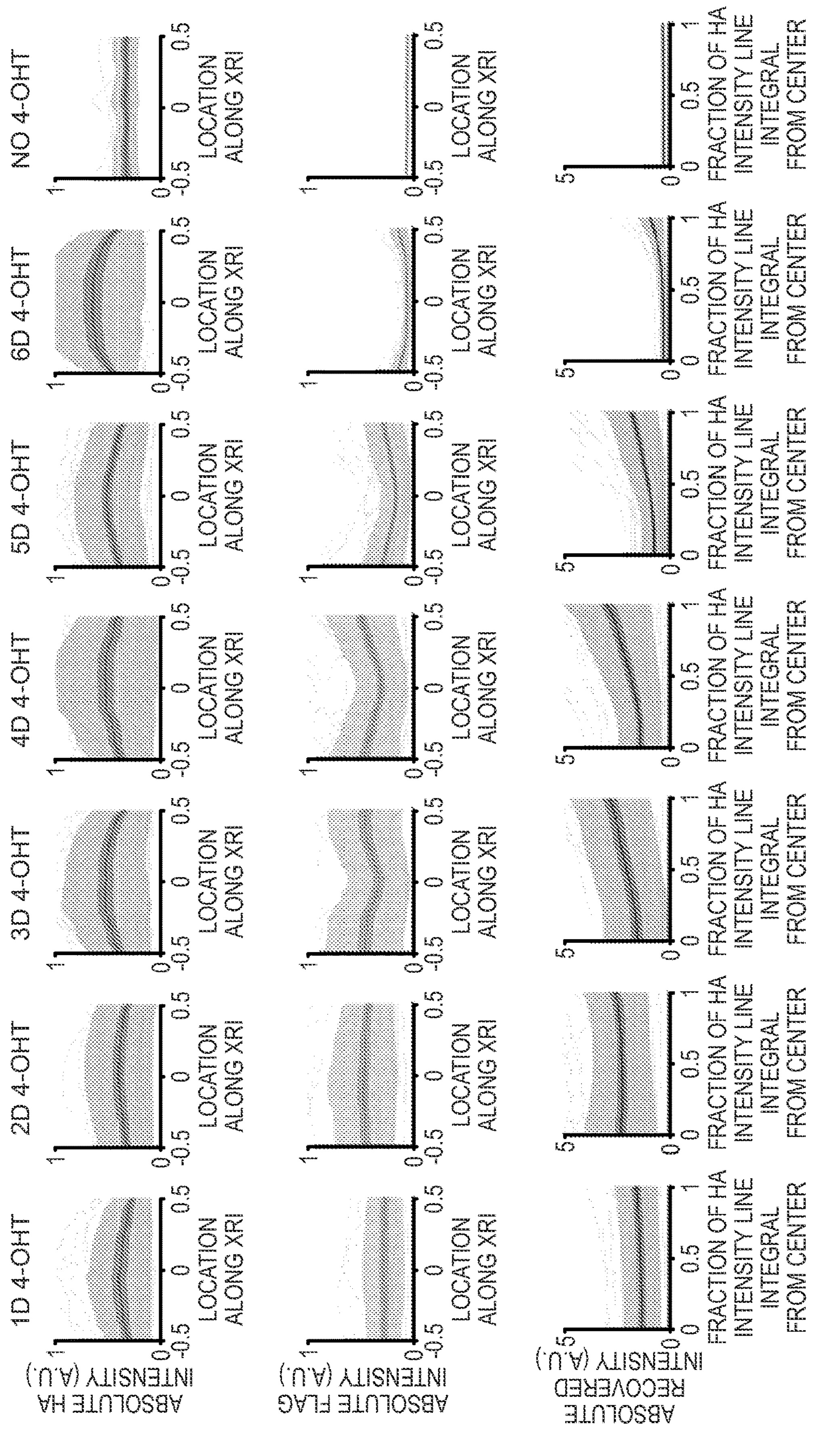
FIG. 6A-D provides plots of results from additional intensity profile analysis and geometric analysis of XRI.

To study how accurate this XRI protein assembly could preserve time information, the chemically-inducible Cre system was again used and different neuron cultures expressing the XRI were treated with 4-OHT at different times after beginning of expression. To increase the efficiency of gene delivery, adeno-associated viruses (AAVs) were also used to deliver the chemically-inducible Cre system and the XRI genes into cultured mouse neurons. Because the expression of AAV is slower compared to DNA transfection, the expression time window was increased from 3 days to 7 days before fixation, immunofluorescent labeling, and imaging. The neuron cultures were divided into 7 groups, and 4-OHT treatment was added at 1, 2, 3, 4, 5, or 6 days after AAV transduction, or not at all (FIG. 5A-C). Results showed continuous HA immunofluorescence in neurons in all groups (FIG. 5D). Results showed the XRI assemblies to have no FLAG immunofluorescence in neurons without 4-OHT treatment, indicating negligible leak expression of the chemically inducible Cre system (FIG. 5D, 'No 4-OHT' panel). The FLAG immunofluorescence was found to have strong polarized patterns (e.g., brighter at the ends than in the middle) in neurons with 4-OHT treatment on day 3, 4, 5, or 6 after AAV transduction, but not to have polarized patterns in neurons with 4-OHT treatment on day 1 or 2 after AAV transduction (FIG. 5D-E; FIG. 6A for the unnormalized version of the plots in FIG. 5E); the HA tag showed a gentle polarization trend in the opposite direction, perhaps because the HA-bearing subunits available were landing on the growing protein chain at greater distances due to the FLAG-bearing subunits having already been added. It was reasoned that on 1 and 2 days after AAV transduction the XRI assemblies either did not form stably, or did form stably but with a substantial amount of lateral growth. Thus, the XRI can start reliably recording the expression time course of FLAG-bearing monomers 3 days after AAV transduction, but not 1 or 2 days after AAV transduction.

Next, studies were performed to quantify the relationship between the times of 4-OHT treatment and the resulting FLAG immunofluorescence patterns on XRI assemblies in neurons. Because the XRI growth is bidirectional over the 7-day experiment, the fractional cumulative HA expression (i.e., the normalized, unidirectional line integral of HA immunofluorescence starting from the center of the XRI) at the center of the XRI was defined as '0' and at the end of the XRI was defined as '1' (see FIG. 7 for details of quantification). It was considered that this measure, the fractional cumulative HA expression, would correspond to a calibratable measure of time, postulating HA-bearing monomers to be added at a constant rate regardless of the presence of non-HA-bearing monomers (i.e., FLAG-bearing monomers here), at least over the time scale of this experiment. That is, when FLAG-bearing monomers are being created, HA-bearing monomers are still being added to the growing polymer chain at a constant rate, although they are landing at more distant places along the chain, because the FLAG-bearing monomers have already been added to the chain, lengthening the distance at which the FLAG-bearing monomers will land. Results indicated HA intensity to significantly decrease towards the end of the XRI, when FLAG intensity increased due to 4-OHT induced expression of FLAG-bearing monomers (see '3-6d 4-OHT' groups the first row in FIG. 5E). In addition, this decrease in HA intensity towards the end of the XRI was not observed without 4-OHT treatment (see 'No-4-OHT' group in the first row in FIG. 5E). Because the 1POK-mediated fiber assembly has a fixed longitudinal monomer-to-monomer distance (8 nm from electron microscopy measurements) [Garcia-Seisdedos, et al. *Nature* 548, 244 (2017)], the above results suggest that FLAG-bearing monomers took over a significant amount of longitudinal space at the end of the XRI and thus diluted the line density of HA-bearing monomers.

Results were then examined to determine whether HA-bearing and FLAG-bearing monomers were adding independently, each at a rate independent of the presence of the other monomer. If the binding and retention of HA-bearing monomers and FLAG-bearing monomers onto the XRI were both rare enough in time that the chance of both types of monomers competing for the same slot on the XRI was insignificant, then this would be plausible. And, in this case, the fractional cumulative HA expression would still be a proper, calibratable measure of time. That is, if units with a new tag are supplementing the units being constitutively synthesized bearing an old tag, the latter units would not be added at a slower rate (i.e., there is no competition between the new units and the old units for being added to the growing chain), but instead would be added at the same rate, but simply be spaced out further from each other, separated by the units bearing the new tag. This would make the line integral the appropriate measure for extracting absolute time measurements. Experiments were performed to empirically test the hypothesis that absolute time measurements could be extracted from this specific measure. The FLAG signals across the two halves of the XRI (because XRIs are symmetric) were averaged, to obtain the final FLAG signal (FIG. 5E, bottom). Then, calculations of the ratio of the FLAG signal at the end of the XRI to the FLAG signal at the center of the XRI (FIG. 5F) were performed, confirming that the polarized patterns of FLAG immunofluorescence on XRIs are present in neurons with 4-OHT treatments 3, 4, 5, or 6 days after AAV transduction, but not in neurons with 4-OHT treatments 1 or 2 days after AAV transduction, as hypothesized above in the section on time-lapse imaging. Therefore, we further analyzed the XRIs in neurons with 4-OHT treatments 3, 4, 5, or 6 days after AAV transduction, to characterize the relationship between the time of 4-OHT treatment and the fraction of the line integral of HA intensity at which the FLAG signal began to rise.

Figure 5G:
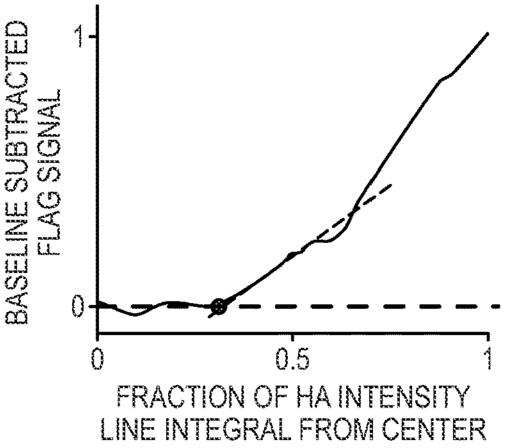
Figure 5H:
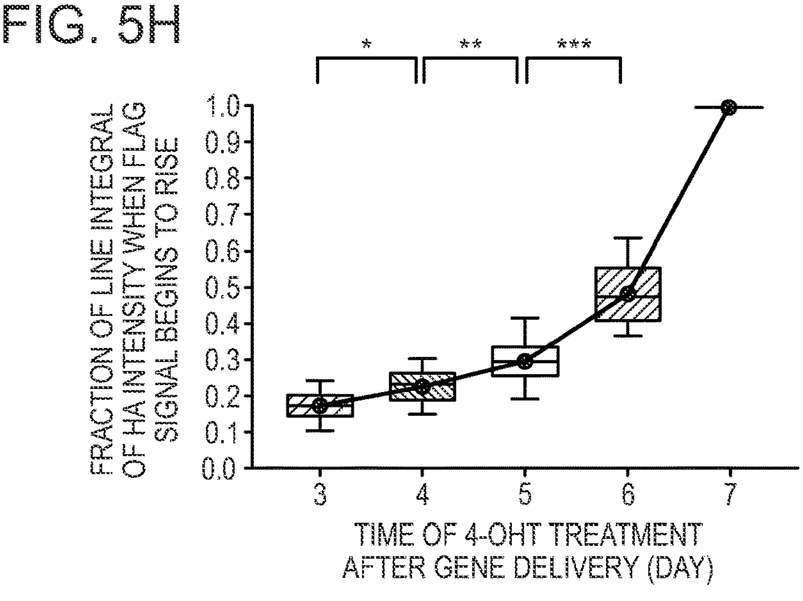
Figure 6B:
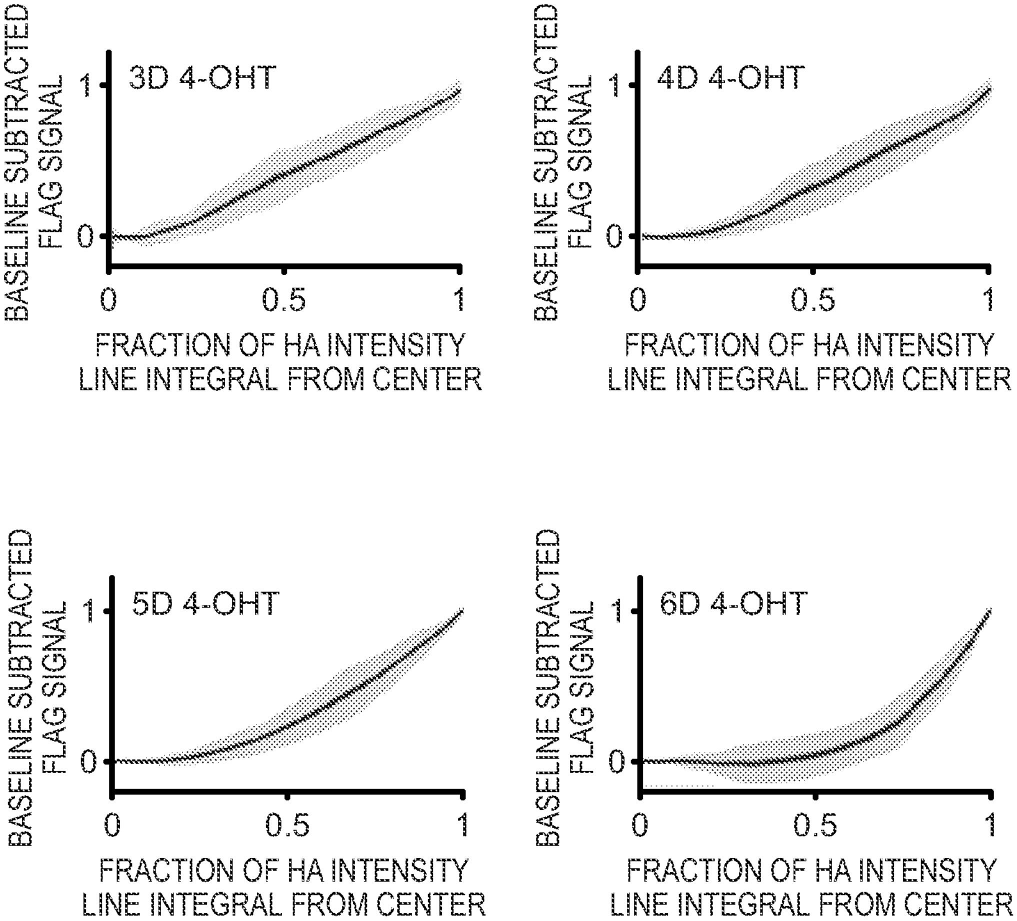
Figure 6C:
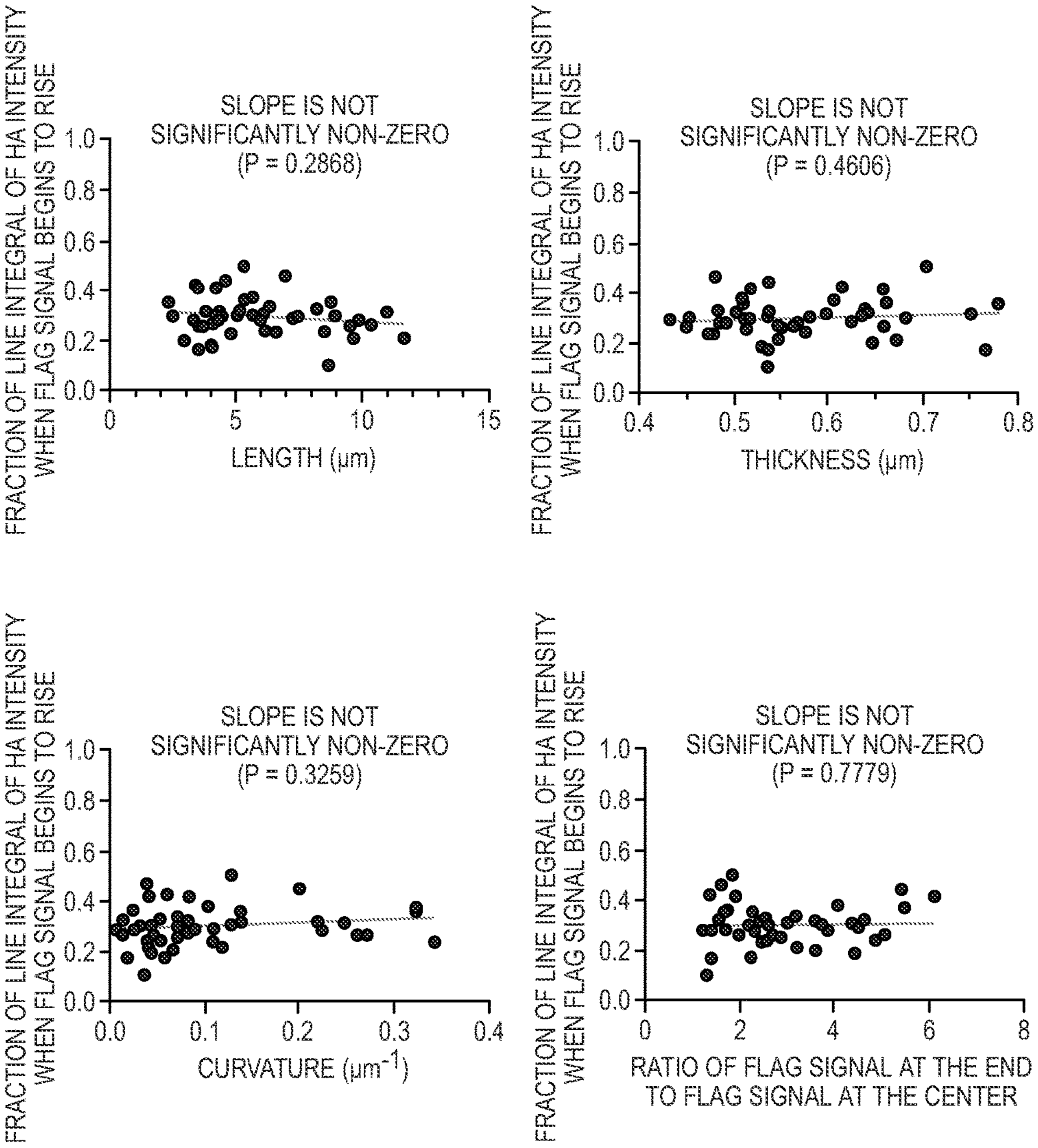
Figure 6D:
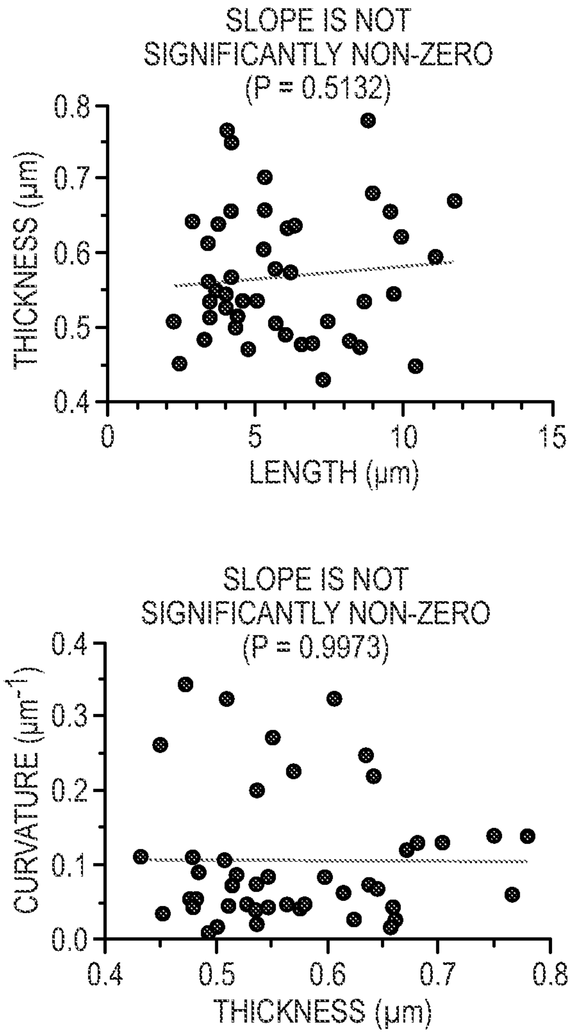
Figure 7A:
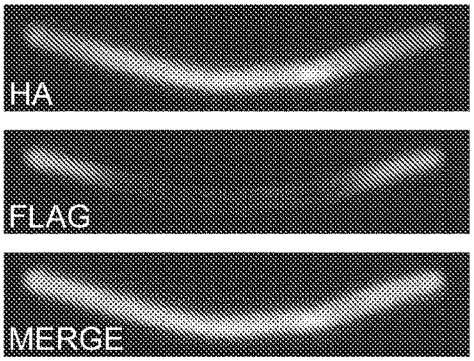
FIG. 7A-F provides images and plots illustrating an embodiment of process flow for extracting information from XRI assemblies. Step 1: For each XRI (FIG. 7A), a curved centerline was drawn along the longitudinal axis of the XRI in the anti-HA channel (FIG. 7B). The centerline width was set to half of the width of the XRI. Step 2: The intensity profiles along this centerline were measured in the anti-HA channel (resulting in an HA line profile; cyan curve in FIG. 7C) and in the other XRI epitope staining channel, such as in the anti-FLAG channel (resulting in a FLAG line profile; magenta curve in FIG. 7C). Step 3: Next, each of the line profiles was split into two half line profiles using the geometric center point of the XRI (the 50% length point along the centerline, measuring from the end of the XRI; gray dashed vertical line in FIG. 7C) as the 'split point'. Each of the half HA line profiles was then converted into a line integral of HA, by integrating the line profile with respect to the distance along the half centerline starting from the split point, and then these line integrals of HA were normalized to the maximum integral value so that each line integral of HA started at the value 0 at the split point of the XRI, and gradually increased to the value 1 at the end of the XRI (see Examples and Methods sections for equations for the quantifications throughout FIG. 7). For the corresponding half FLAG line profiles, line integrals were also calculated but not normalized. At this point, results include the line integrals of HA and FLAG, which correspond to the cumulative HA and FLAG intensities along each half of the XRI. The FLAG intensity change per unit change in the cumulative HA intensity, defined as the FLAG signal, was calculated by taking the derivative of the line integral of FLAG with respect to the line integral of HA (gray curves in FIG. 7D). At this stage, the line integral of HA and the FLAG signal had been obtained from each of the halves of the XRI, and the final extracted FLAG signal from this XRI (black curves in FIG. 7D) was defined as the point-by-point average of the two FLAG signals from the two halves of the XRI. Step 4: it was determined that the two obtained FLAG signals from the same XRI had small but noticeable differences (see the two gray curves in FIG. 7D). It was reasoned that such small but noticeable discrepancies between the two halves of the same XRI were due to the asymmetry of the XRI, and the choice of the exact geometric center as the split point may not be optimal. To minimize the discrepancy between the two FLAG signals from the two halves of the same XRI, a search was performed for an optimal split point (black dashed vertical line in FIG. 7E) near the geometric center of the XRI (searching range was the geometric center +/−10% of the total XRI length, i.e., between −0.1 and 0.1 on the x-axis in FIG. 7E), so that using this optimal split point, instead of the geometric center, as the split point would result in the least difference (in terms of sum of squared differences) between the two FLAG signals from the two halves of the split XRI. Step 5: Same as Step 3, except that the optimal split point, instead of the geometric center, was used to split the intensity profiles into two halves (FIG. 7F). It was determined that the resulting final FLAG signal (after averaging those from the two halves) when using the geometric center as the split point was similar to that when using the optimal split point as the split point (compare the black line in FIG. 7D and FIG. 7F). The optimal split point was used as the split point to analyze XRIs herein.
Figure 7B:
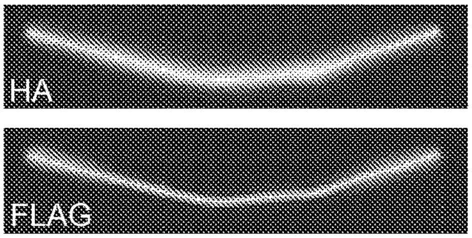
Figure 7C:
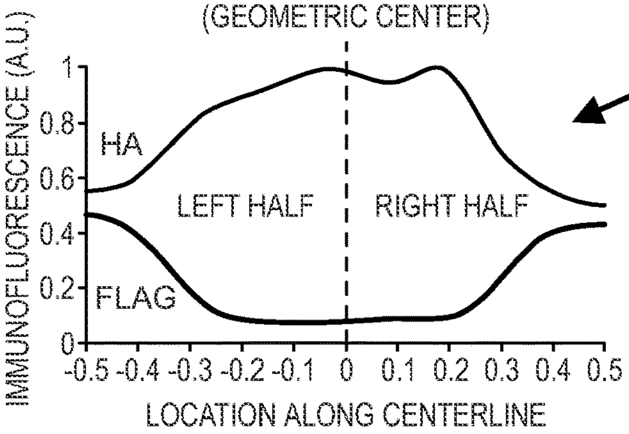
Figure 7D:
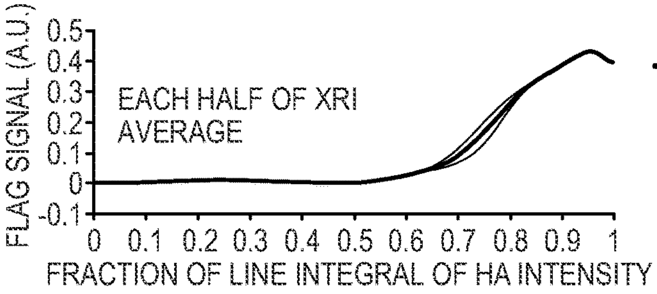
Figure 7E:
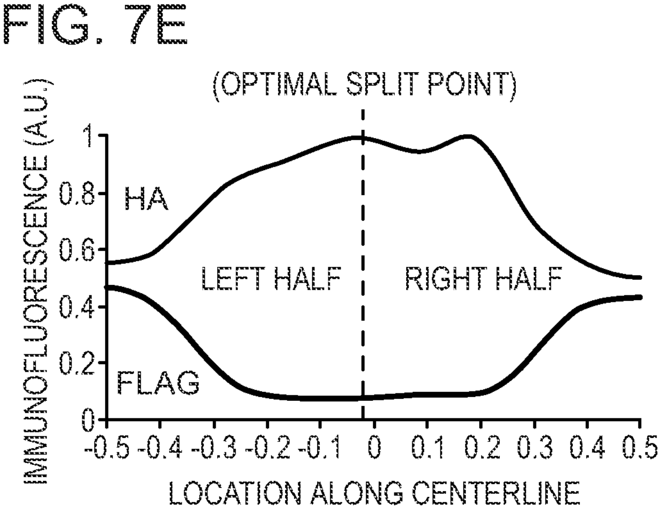
Figure 7F:
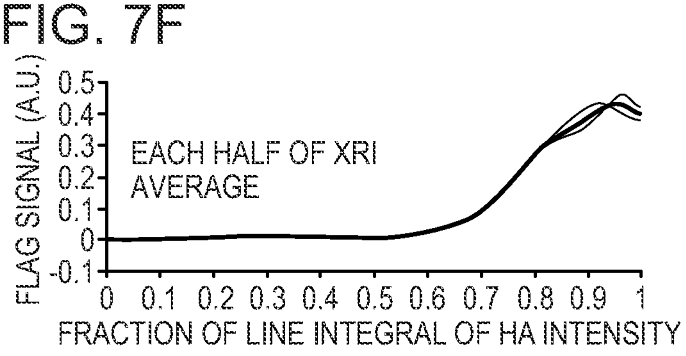
Figure 8A:
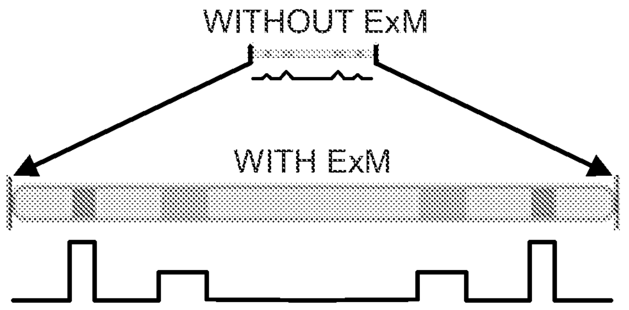
FIG. 8A-I provides schematics, images, and plots of results of imaging XRIs using expansion microscopy. The experiment described in FIG. 5 was replicated and expansion microscopy [Chen, F., et al., *Science* Vol 347, Issue 6221 pp.543-548 (2015)](ExM) was applied instead of confocal microscopy for immunofluorescence imaging of XRIs. Digestion methods were optimized (removing the proteinase K digestion step and replacing it with a heat-based softening step) starting from the TREx [Damstra, H. G. J. et al. *bioRxiv* 2021.02.03.428837 (2021). doi:10.1101/2021.02.03.428837] ExM protocol, while receiving inspirations from the ExR [Sarkar, D. et al. *bioRxiv* 2020.08.29.273540 (2020). doi:10.1101/2020.08.29.273540] protocol, to achieve uniform expansion of XRI assemblies and post-expansion immunostaining/immunofluorescence at a high signal-to-noise-ratio (at a linear expansion factor of ~5×), with antibody staining against NeuN to locate the somata of neurons.
Figure 8B:
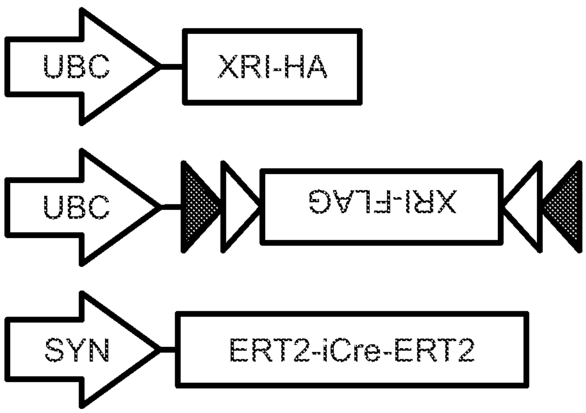
Figure 8C:
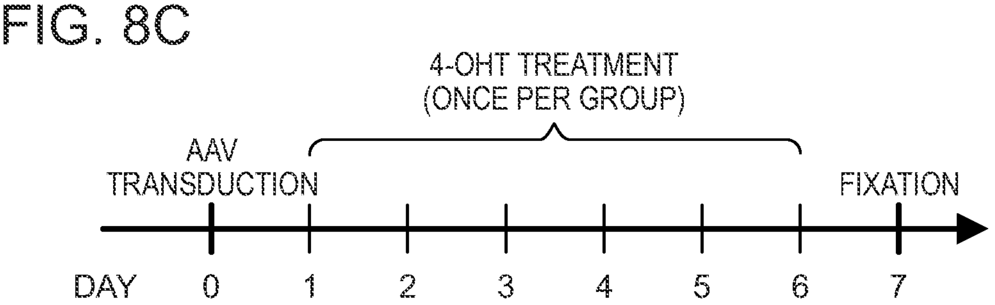
Figure 8D:
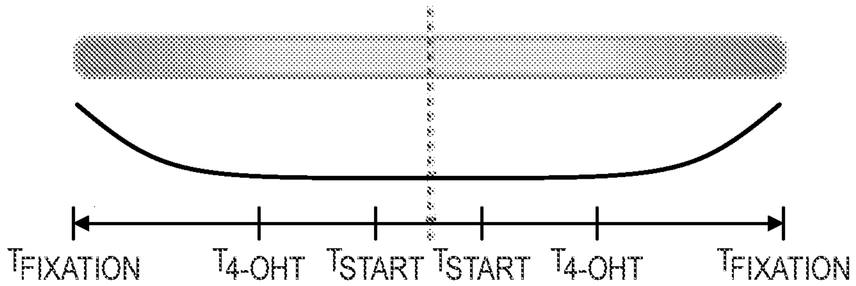
Figure 8E:
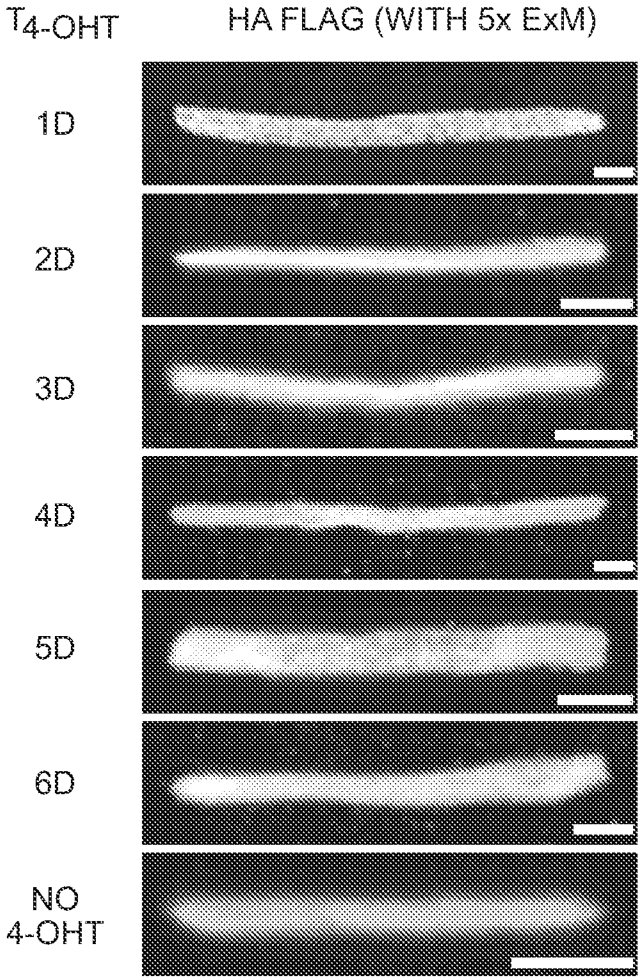
Figure 8F:
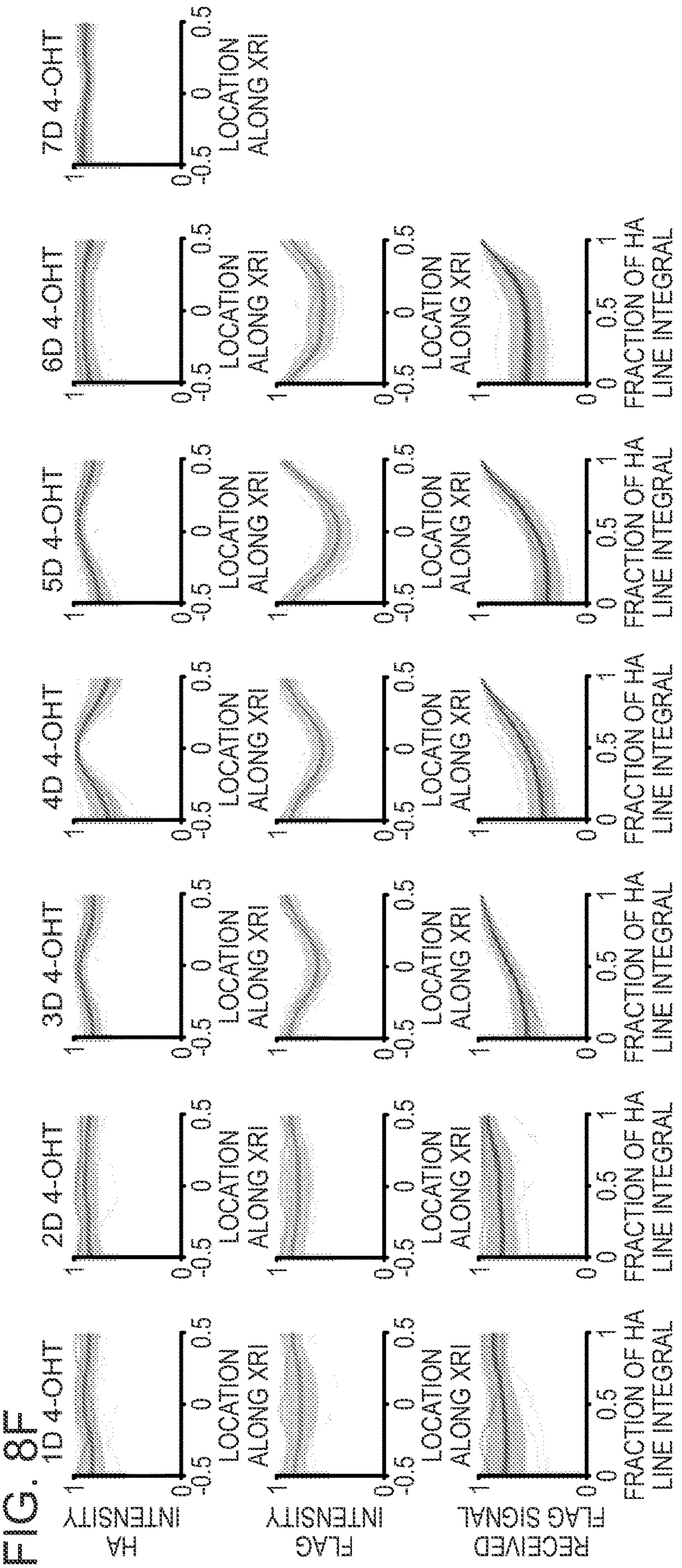
Figure 8G:
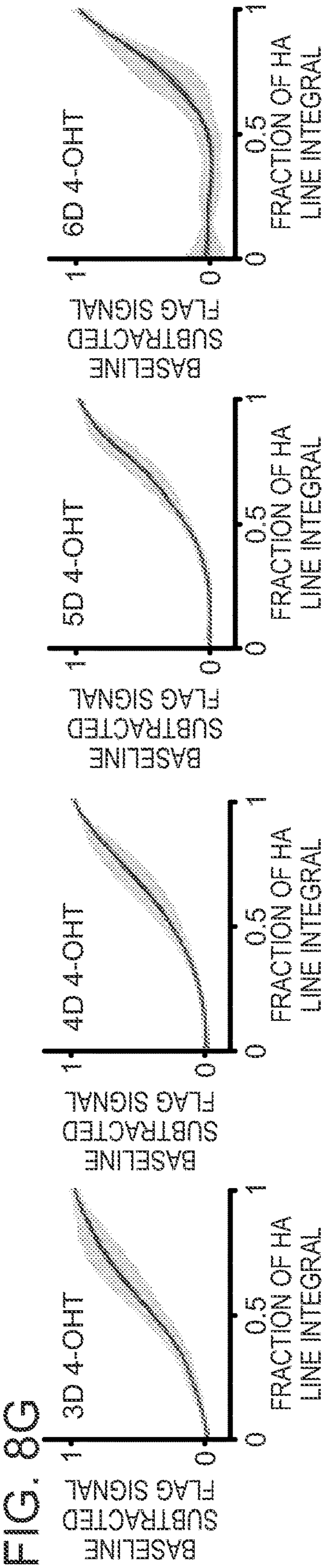
Figure 8H:
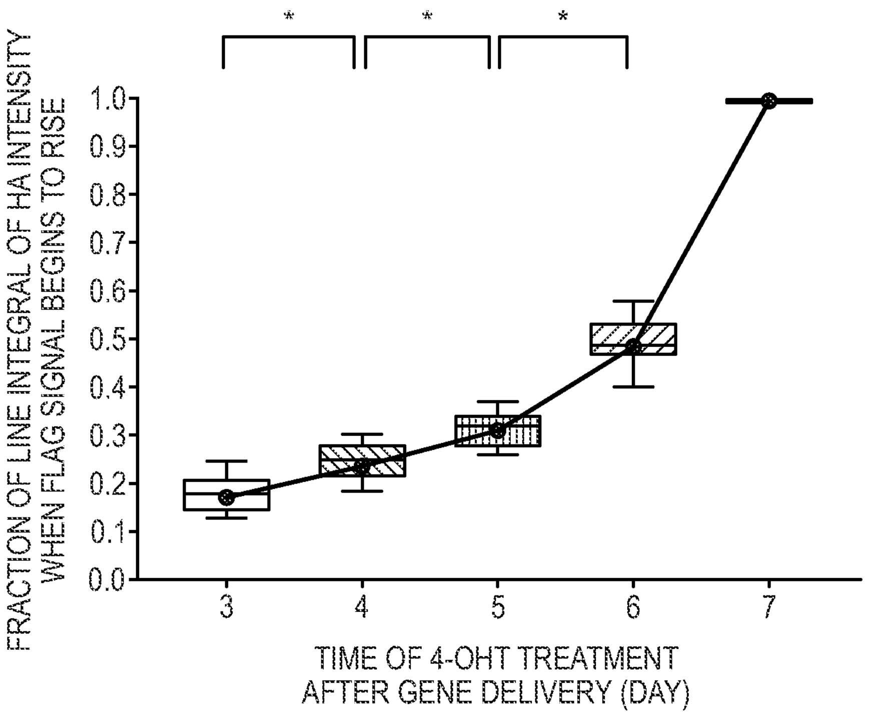
Figure 8I:
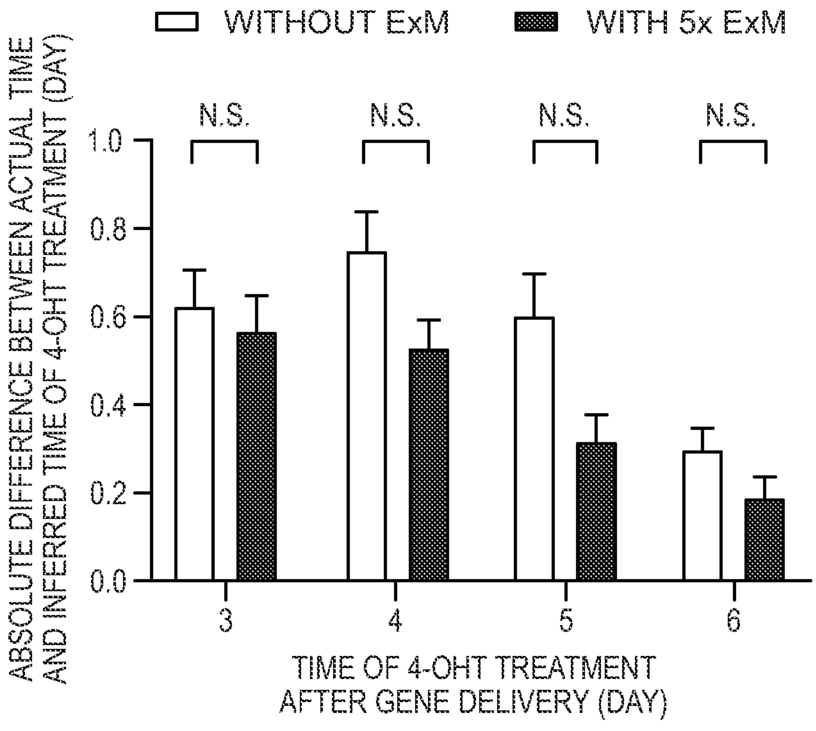

To quantify the fraction of the line integral of HA intensity at which the FLAG signal began to rise, the net waveform of the FLAG signal was generated with respect to the fraction of the line integral of HA intensity, by subtracting the baseline (i.e., the FLAG signal when the fraction of the line integral of HA intensity is zero) from the FLAG signal (FIG. 6B). Next, the initial rising phase of the FLAG signal (defined as the period over which the FLAG signal increased from 10% to 50% of its peak value) was extrapolated until it intersected the pre-rising phase baseline (FIG. 5G). The fraction of the HA line integral at this intersection point was defined as the point in time (although of course, to pinpoint a numerical value for the time requires calibration, discussed below) at which the FLAG signal began to rise. Importantly, this point did not depend on the length, thickness, or curvature of the XRI, nor did it change with the precise value of the ratio of the FLAG signal at the end of the XRI to the FLAG signal at the center of the XRI (FIG. 6C)—implying that this measure of time was a robust measure, and not dependent on the details of the geometry of the XRI, and any associated constraints on the formation of the XRI. We also did not observe any correlation between the length, thickness, and curvature of XRI (FIG. 6D), implying a certain degree of robustness as to the independence of different XRI geometrical attributes, and consistent with the stabilization hypothesis above. As the time of 4-OHT treatment time increased, the fraction of the line integral of HA intensity when the FLAG signal began to rise also increased, albeit at a non-constant (i.e., increasing) rate, suggesting that the expression rate of AAV delivered XRI genes, and the elongation rate of XRI, increased over time (FIG. 5H). These results are in agreement with the earlier observation in the time-lapse experiment, above, where the elongation of XRI growth pattern (compare FIG. 1I with FIG. 5H). These observations are consistent with the idea that the rate of addition of HA-bearing monomers to the XRI assembly was not altered by the presence of the FLAG-bearing monomers over the time scale measured in our experiments, although it is unknown whether such independence was indeed due to the two kinds of monomers rarely competing in time for the same slot on the XRI (as was speculated in the previous paragraph) or due to other mechanisms. Nevertheless, it was found that the time of a given cellular event could indeed be extracted from XRI geometry and label density, analyzed thus. This value was normalized to be 1 on day 7, because that was the time of cell fixation and thus the end of XRI growth (see day 7 in FIG. 5H). This experiment was also replicated and applied expansion microscopy [Chen, F., et al., *SCIENCE* 30 Jan. 2015 Vol 347, (6221) 543-548 DOI: 10.1126/science.1260088] (ExM) was applied instead of confocal microscopy for immunofluorescence imaging of XRI, obtaining similar results (FIG. 8). Thus, the predictable relationship between time of drug administration, and the fraction of the line integral of the HA intensity at which the FLAG signal began to increase, enables us to calibrate time information in XRI data analysis.

Figure 9A:
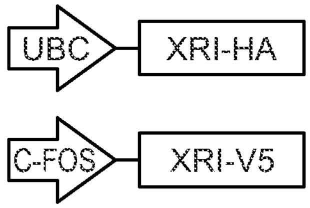
FIG. 9A-L provides schematics, images and plots illustrating results of recording the time course of c-fos promoter-driven expression with XRI.
Figure 9B:
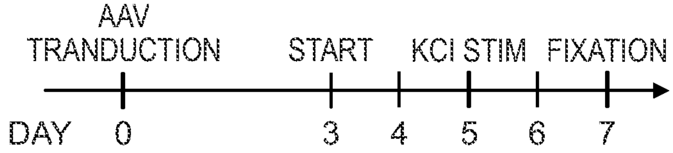
Figure 9C:
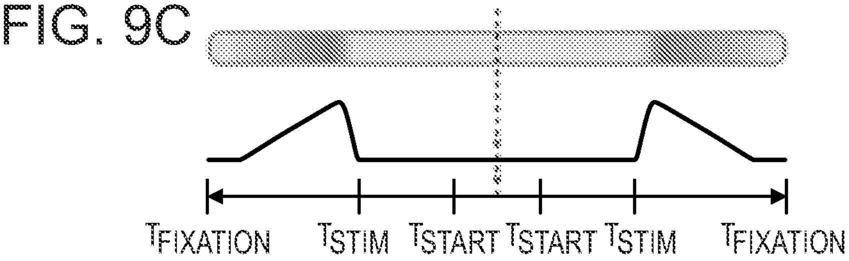
Figure 9D:
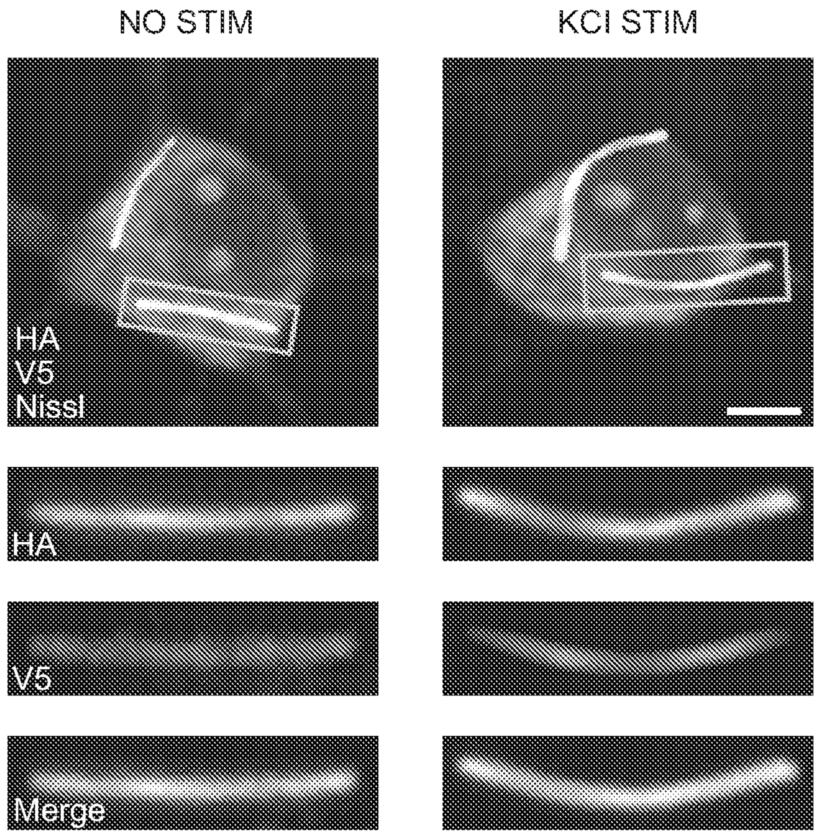
Figure 9E:
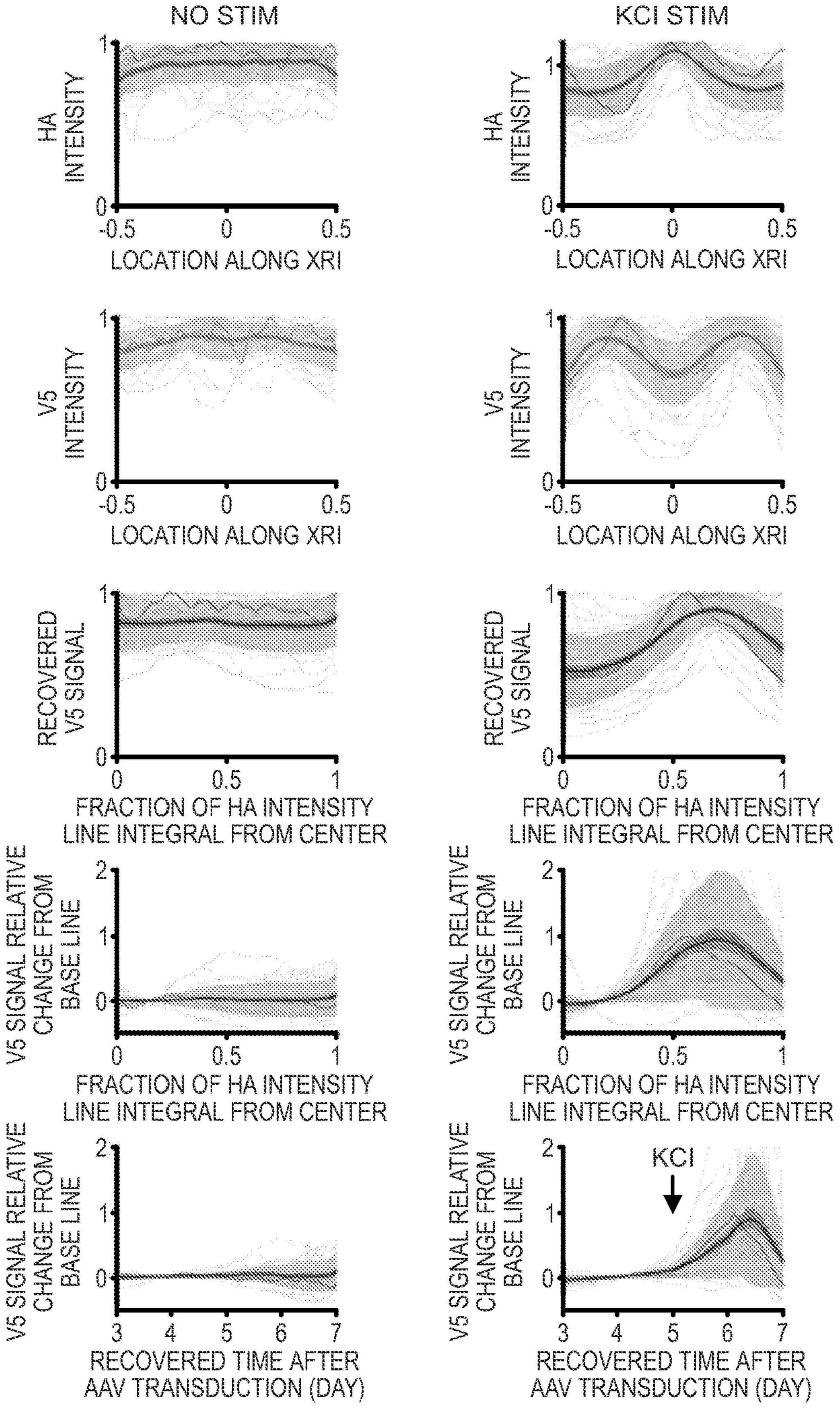
Figure 9F:
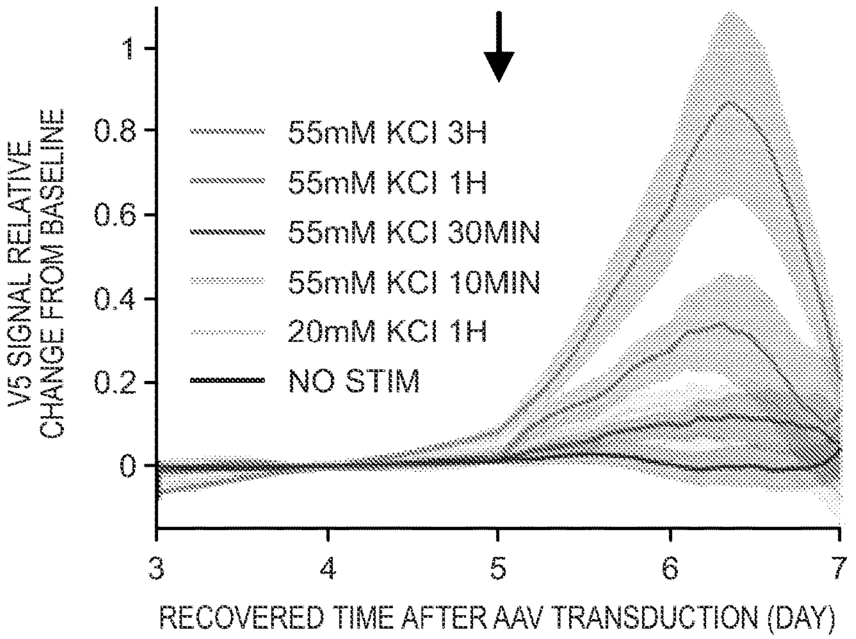

Experiments were then performed to explore whether XRIs could be used to record gene expression timecourse under mammalian immediate early gene (IEG) promoter activation. IEG promoters, such as the c-fos promoter [Roy, D. S. et al. *Nat.* 2016 5317595 531, 508-512 (2016)], are widely used to couple the expression of reporter proteins to specific cellular stimuli [Kawashima, T., et al., *Frontiers in Neural Circuits* 8, 37 (2014)]. By using the c-fos promoter to drive the expression of XRI subunits tagged by a unique epitope tag, here the V5 tag, the time course of c-fos promoter driven expression could be recorded along the XRI filament, and read out by measuring the intensity profiles of V5 immunostaining signals along the filament. The V5 tag was chosen to use here, instead of the previously used FLAG tag, so that each new XRI construct would be tagged by a unique epitope tag: in future usage of XRIs, one may want to co-express multiple XRI constructs in the same cell to achieve multiplexed recording of several different kinds of biological signals, readable via multiplexed immunostaining against distinct epitope tags. HA-bearing XRI, driven by the UBC promoter, was expressed in neurons using AAV as in the experiments in FIG. 5, along with the new V5-bearing XRI driven by the c-fos promoter (FIG. 9A-C). The AAV was diluted for the V5-bearing XRI (the final titer was 25% of that of the AAV for the HA-bearing XRI) so that the expression of HA-bearing monomers (and thus the HA portion of the final XRI assembly) would dominate over V5-bearing ones, and serve as a reliable integral substrate. The neurons were stimulated with 55 mM KCl, a common method to induce neuronal depolarization, for 3 hours, known to result in an increase in c-fos expression [Malik, A. N. et al. *Nat. Neurosci.* 17, 1330 (2014); Tyssowski, K. M. et al. *Neuron* 98, 530-546.e11 (2018); Joo, J.-Y., et al., *Nat. Neurosci.* 2016 191 19, 75-83 (2015)]. As expected, in the KCl stimulated neurons low V5 immunofluorescence was observed at the middle of the XRI, and towards both ends of the XRI the V5 immunofluorescence increased, resulting in peak-like patterns on each of the two sides of the XRI, eventually falling off (FIG. 9D-E, right). This peak-like pattern of V5 immunofluorescence was not observed in XRIs in neurons without KCl stimulation (the ‘No Stim’ group; FIG. 9D-E, left). The HA intensity fluctuated the opposite way of the V5 intensity (FIG. 9D-E, right), as expected because, as discussed elsewhere herein, V5-bearing monomers would dilute down the line density of HA-bearing monomers; as long as the new V5 units being added were not competing with HA units being added, but simply were spacing the HA units out further, the line integral of HA units being added would be a useful measure of absolute time, at least over the time scale of this experiment (see above herein). Using the relationship between time and line integral of HA intensity obtained above (FIG. 5H), relative change of V5 signal from baseline (baseline defined as the V5 signal when the fraction of the line integral of HA intensity was zero) along the XRI was plotted versus time. As expected, a peak of V5 signal was observed after the recovered time of day 5, which matched the actual time of KCl stimulation (FIG. 9E, bottom row), while in neurons without KCl stimulation the V5 signal stayed relatively unchanged.

Figure 10A:
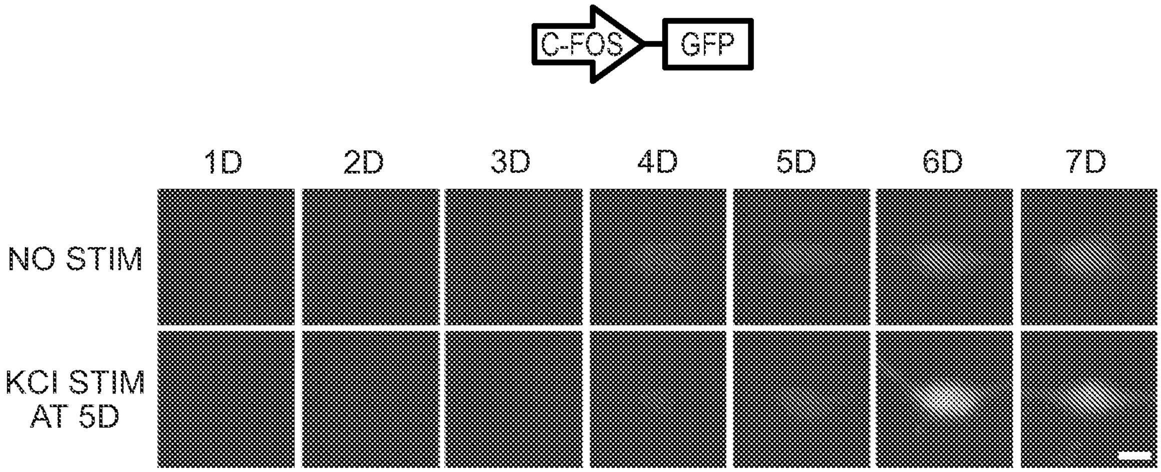
FIG. 10A-D provides schematics, images and graphs of results from KCl stimulation of cultured neurons with c-fos promoter-driven expression of GFP.
Figure 10B:
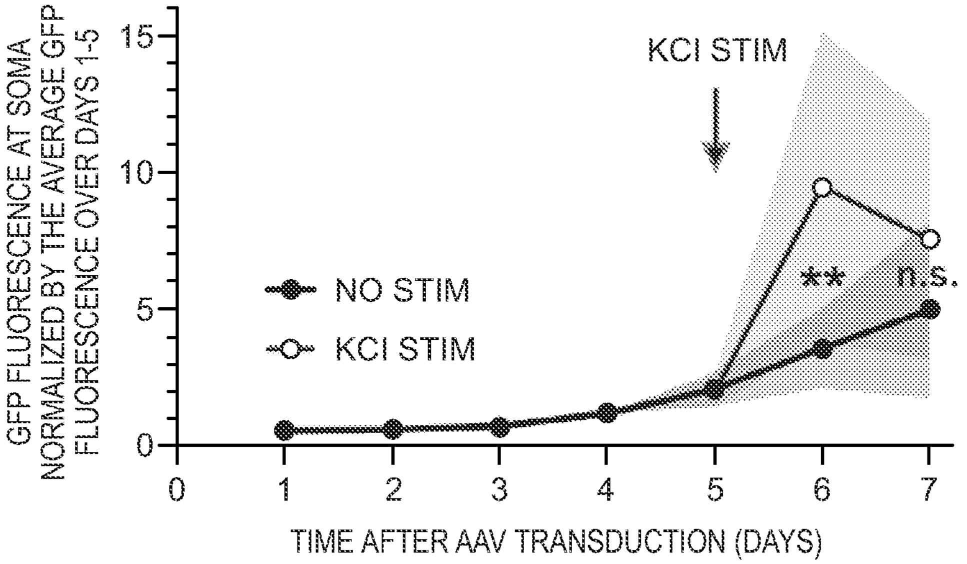

To validate the XRI-recorded time course of c-fos promoter driven expression, studies were carried out that included performing time-lapse imaging, one image per day, of cultured neurons transduced with an AAV construct encoding c-fos promoter-driven expression of GFP, under the same KCl stimulation (FIG. 10A). It was found that the waveform of GFP intensity over time was similar to the XRI-recorded time course of c-fos promoter-driven expression (compare FIG. 10B and FIG. 9E, bottom row), although the non-stimulated case accumulated a small amount of GFP, presumably because of baseline neural activity in the culture [Rodriguez-Berdini, L. et al. *J. Biol. Chem.* 295, 8808-8818 (2020)], whereas the XRI case did not exhibit a peak in the non-stimulated case, perhaps because the baseline neural activity provided a constant background level of available XRI subunits.

Figure 9G:
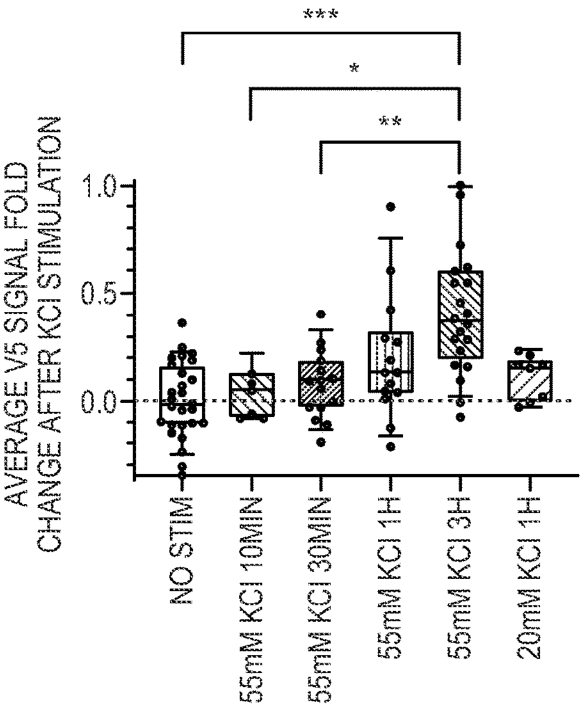
Figure 9H:
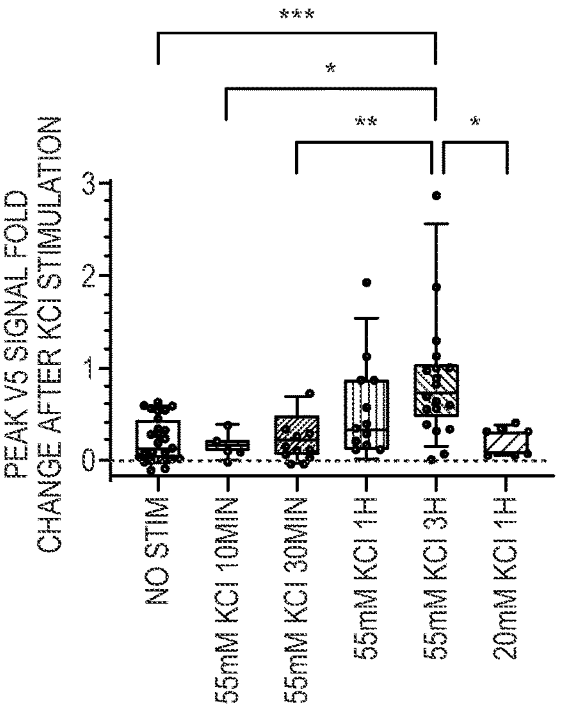
Figure 9I:
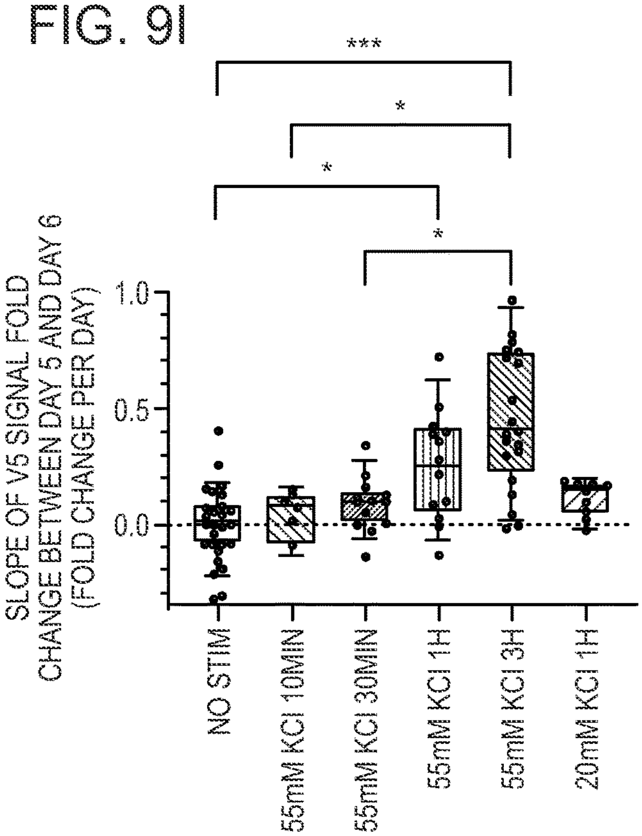
Figure 9J:
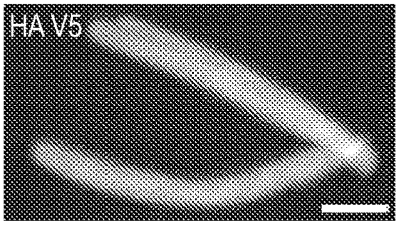
Figure 9K:
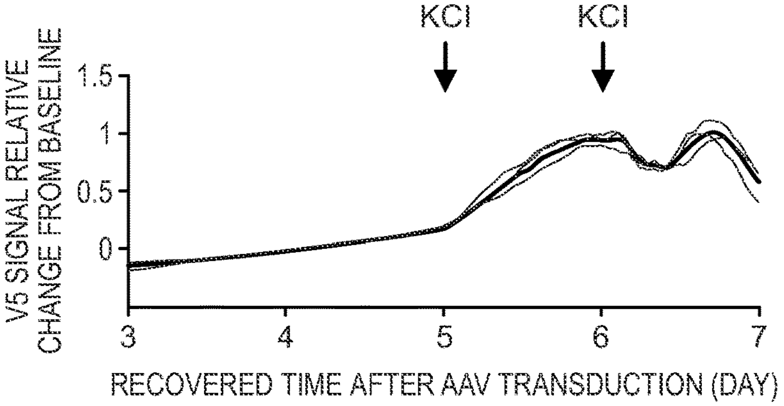
Figure 9L:
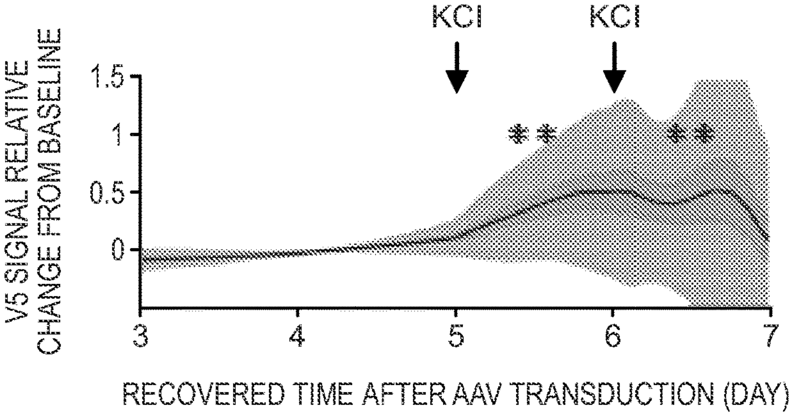
Figure 10C:
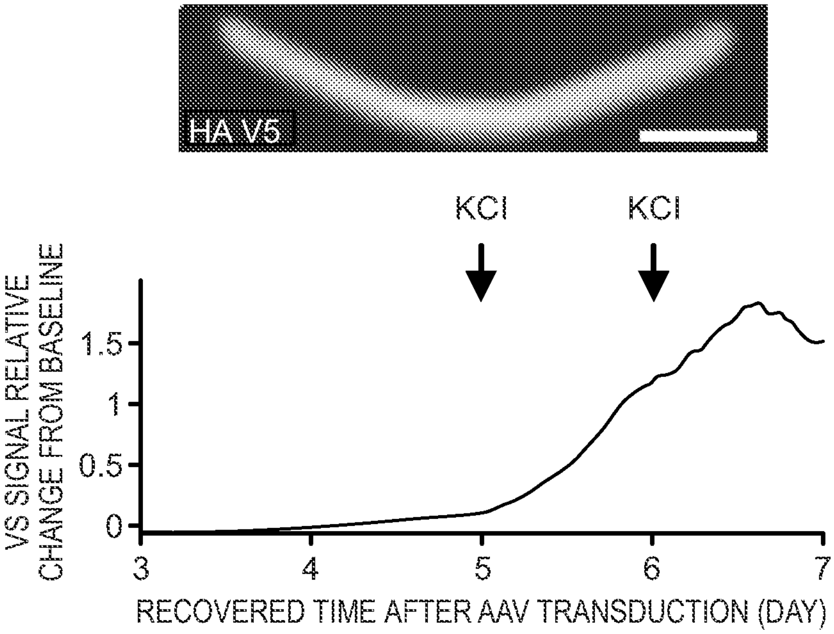
Figure 10D:
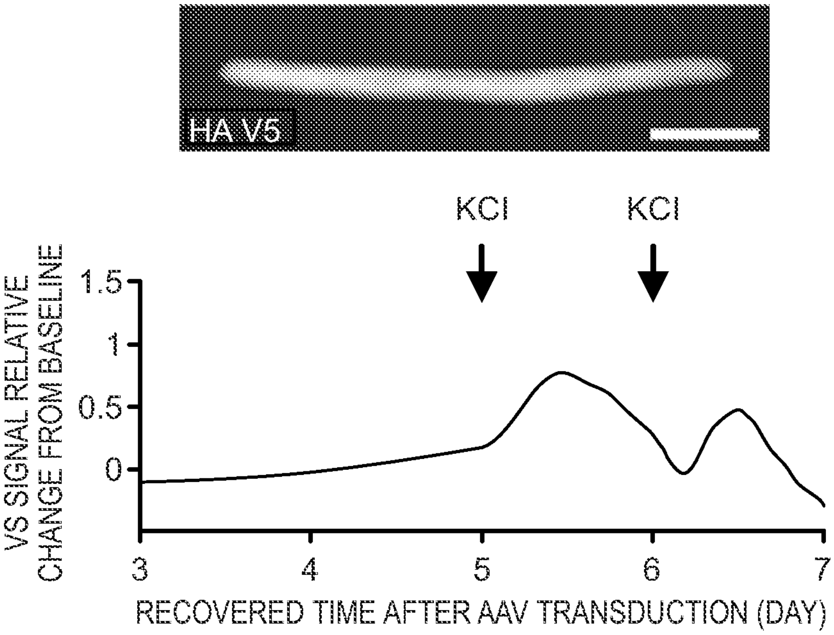

To assess the sensitivity of the XRI fos recorder, experiments were carried out that included XRI recording of c-fos promoter driven XRI expression with different doses and durations of KCl stimulation (FIG. 9F), analyzing the average post-stimulation XRI amplitude, the peak post-stimulation XRI amplitude, and the rising slope of the XRI after KCl stimulation. It was determined that the XRI system responded with brighter and higher-slope signals with stronger and longer stimulations, than weaker and shorter ones (FIG. 9G-I). To gauge whether this sensitivity could be applied to detect sequential neural stimulations, experiments were carried out that included two sequential KCl stimulations of the same neural population, separated by 1 day, and it was possible to recover the times of both stimulation events via c-fos promoter driven expression of XRI subunits in cultured neurons (FIG. 9J-K, results from a representative neuron; FIG. 9L, averaged results from all neurons; FIG. 10C-D results from additional neurons).

Figure 11A:
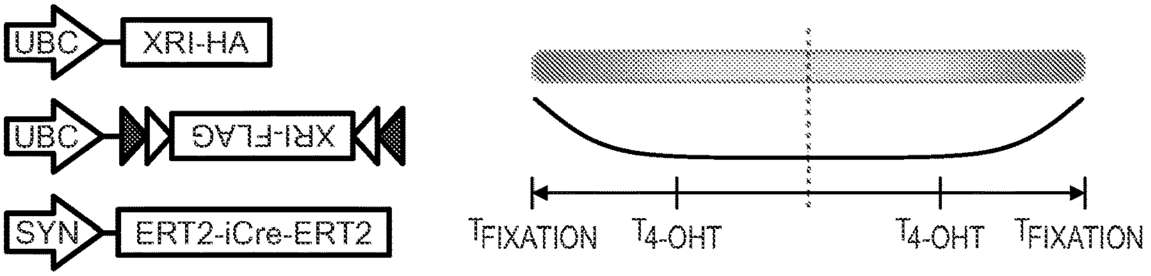
FIG. 11A-F provide schematics, images, and graph of results from study of in vivo XRI self-assembly in mouse brain.
Figure 11B:
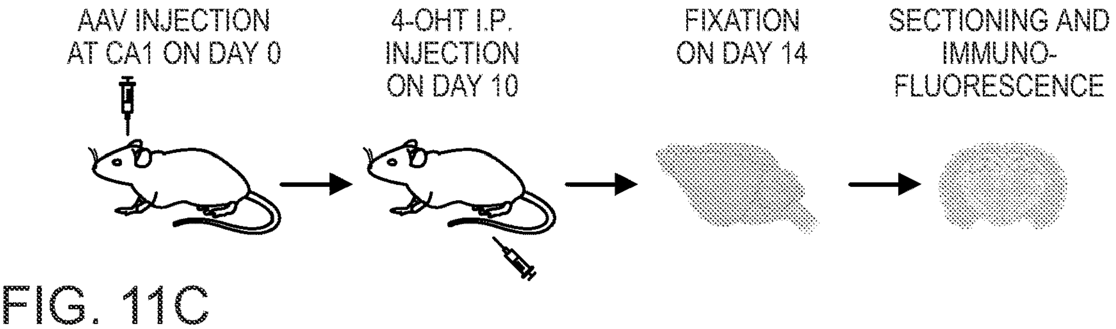
Figure 11C:
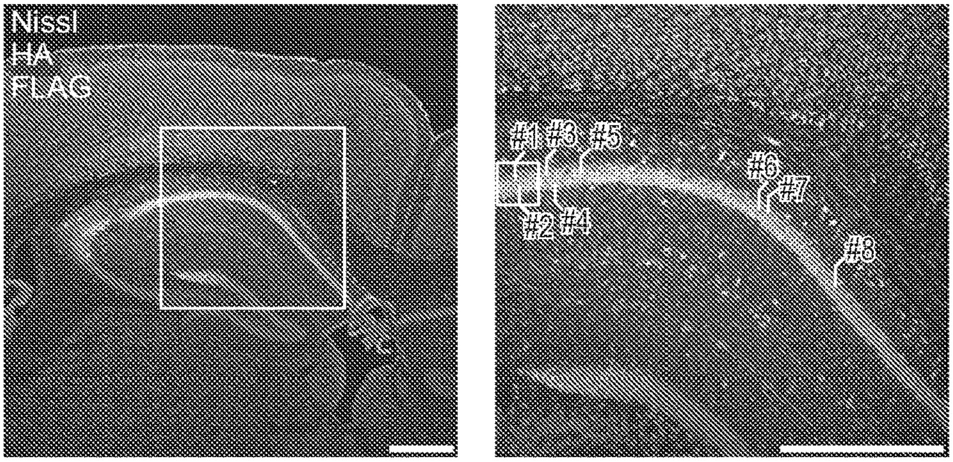
Figure 11D:
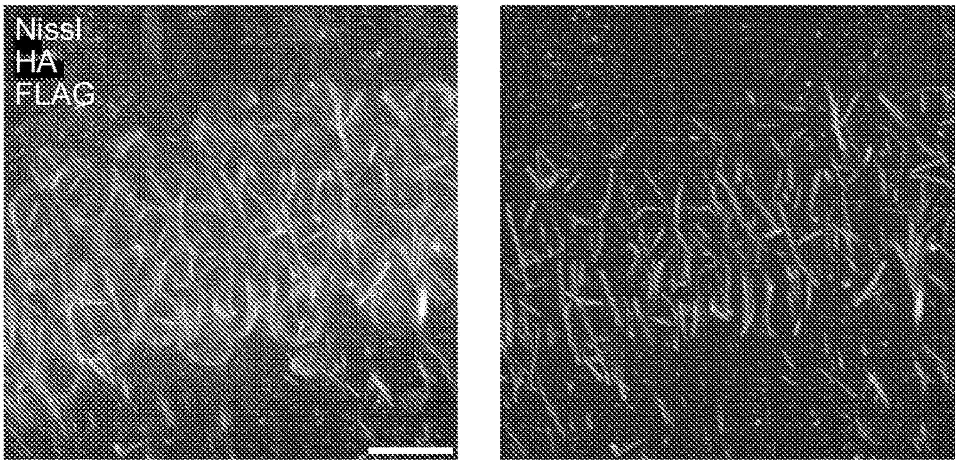
Figure 11E:
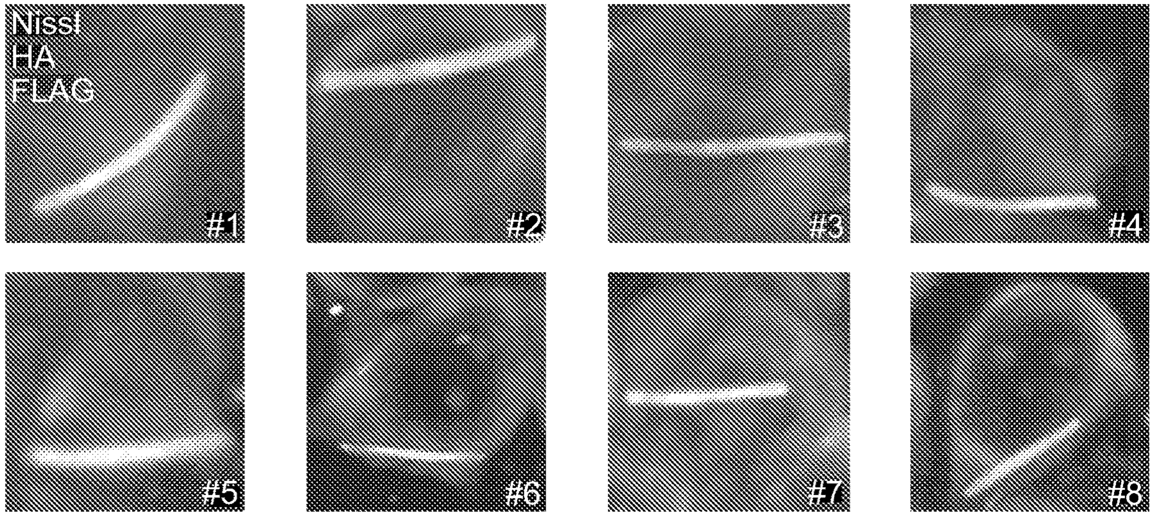

Next, experiments were performed to test whether XRI could preserve temporal information in the living mammalian brain. The same XRI AAVs used in FIG. 5 were co-injected into the hippocampal CA1 region of the brains of adult wild-type mice (FIG. 11A-B). Based on previous experience of the instant inventors and others [Zincarelli, C., et al., *Mol. Ther.* 16, 1073-1080 (2008); Kaspar, B. K. et al. *Proc. Natl. Acad. Sci. U.S.A.* 99, 2320 (2002)] on the AAV-mediated gene delivery of Cre (in the experiment here ERT2-iCre-ERT2 was delivered) into the mouse brain in vivo, the expression time was doubled to 14 days for this in vivo experiment, so that 4-OHT was administered into mouse via intraperitoneal injection [Guenthner, C. J., et al., *Neuron* 78, 773 (2013)] at 10 days after AAV injection (5/7 of the way through the experimental time course) to induce the enzymatic activity of ERT2-iCre-ERT2, which triggers the expression of the FLAG-bearing XRI, and then the mouse brain was fixed and sectioned 14 days after AAV injection for downstream immunofluorescence (see the experiment pipeline in FIG. 11B). After immunofluorescence imaging of the resulted brain slices, abundant expression of XRI in neurons was observed in the CA1 area (FIG. 11C, low-magnification images; FIG. 11D, high-magnification images; FIG. 11E, close-up images of individual representative neurons). Similar to what was observed in cultured neurons in FIG. 5, the FLAG immunofluorescence had a strong polarized pattern in the XRIs formed in vivo, confirming that XRI can indeed preserve temporal information in the living mammalian brain.

Figure 11F:
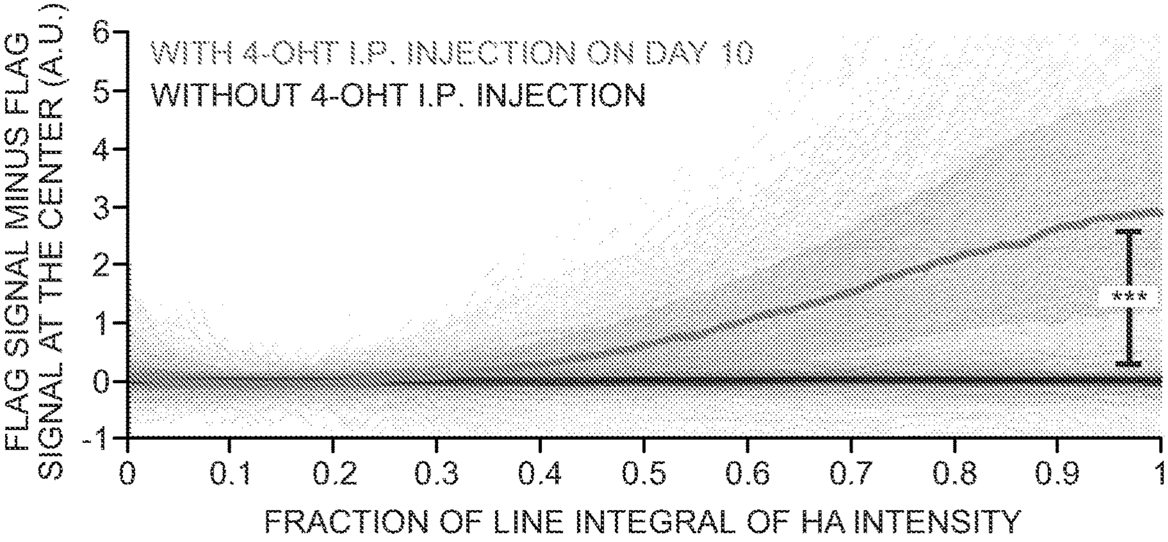

The XRIs in 835 CA1 neurons were analyzed in confocal imaged volumes and plotted the absolute, baseline subtracted (baseline defined as the signal at the center of XRI) FLAG signals with respect to the fraction of the line integral of HA intensity, and the same analysis was performed on XRIs in 475 CA1 neurons in another mouse that underwent the same experimental pipeline but without 4-OHT injection (FIG. 11F). FLAG signals in the mouse without 4-OHT injection were flat with respect to the fraction of the line integral of HA intensity, while those in the mouse with 4-OHT injection on day 10 began to rise when the fraction of the line integral of HA intensity reached 0.3. This 0.3 value alone does not provide absolute information about the time axis, without an in vivo calibration of the timecourse as done in vitro for FIG. 5—but, we note that this 0.3 value, from this day 10 4-OHT injection amidst a 14-day in vivo experiment, matched the same value obtained for the day 5 4-OHT treatment in the 7-day experiment in cultured neurons (FIG. 5H). Note that in both cases, 4-OHT was given at a time point 5/7 of the way through the total XRI expression time, suggesting that this time point corresponds to 30% of the fraction of the line integral of HA intensity, in multiple neural preparations. Work on developing XRI for in vivo should replicate the calibration experiment of FIG. 5H in the living mouse brain, to precisely numerically calibrate the time axis.

Statistical Analysis.

All statistical analysis was performed using the built-in statistical analysis tools in Prism (GraphPad) or MATLAB. The statistical details of each statistical analysis can be found in the figure descriptions.

EQUIVALENTS

It is to be understood that the methods, compositions, and apparatus that have been described above are merely illustrative applications of the principles of the invention. Numerous modifications may be made by those skilled in the art without departing from the scope of the invention. Although the invention has been described in detail for the purpose of illustration, it is understood that such detail is solely for that purpose and variations can be made by those skilled in the art without departing from the spirit and scope of the invention, which is defined by the following claims. The contents of all references, patents and published patent applications cited throughout this application are incorporated herein by reference in their entirety.

We claim:

1. A composition comprising a plurality of expressed expression recording island (XRI) subunits, wherein:

the plurality of expressed XRI subunits is in the soma of a postmitotic neuron cell and each expressed XRI subunit comprises:

one or more of an independently selected self-assembling filament-forming monomer, wherein the independently selected self-assembling filament-forming monomer is selected from a 1POK and a DHF40 protein;

one or more of an independently selected detectable tag; and one or more of an independently selected protein spacer, wherein the independently selected protein spacer is selected from mEGFP and a maltose binding protein (MBP) and is fused to a lateral edge of the expressed self-assembling filament-forming monomers; and wherein the plurality of expressed XRI subunits is a linear chain of the expressed XRI subunits in the soma of the postmitotic neuron cell.

2. The composition of claim 1, wherein the self-assembling filament-forming monomer is an engineered protein.

3. The composition of claim 1, wherein the detectable tag comprises an epitope tag.

4. The composition of claim 3, wherein the epitope tag is a human influenza hemagglutinin (HA) tag.

5. The composition of claim 1, wherein the postmitotic neuron cell is one or more of: a vertebrate cell, a mammalian cell, and a human cell.

6. The composition of claim 1, wherein the detectable tag is positioned between the self-assembling filament-forming monomer and the protein spacer.

7. A method of identifying an expression history record in a cell, comprising:

expressing in a postmitotic neuron cell or in a plurality of postmitotic neuron cells a plurality of independently selected expression recording island (XRI) subunits, wherein the plurality of expressed XRI subunits is in the soma of the postmitotic neuron cell and wherein each encoded XRI subunit comprises:

one or more of an independently selected self-assembling filament-forming monomer, wherein the independently selected self-assembling filament-forming monomer is selected from a 1POK and a DHF40 protein;

one or more of an independently selected detectable tag; and one or more of an independently selected protein spacer, wherein the independently selected protein spacer is selected from mEGFP and a maltose binding protein (MBP) and is fused to a lateral edge of the expressed self-assembling filament-forming monomers; wherein the plurality of expressed XRI subunits is a linear chain of the expressed XRI subunits in the soma of the postmitotic neuron cell and the XRI subunits form a growing protein chain in the soma of the postmitotic neuron cell, the independently selected spacer blocks lateral growth of the growing protein chain of the XRI subunits, and the growing protein chain provides a temporal history of the expression of the XRI subunits; and detecting the protein chain of the XRI subunits in the postmitotic neuron cell or the plurality of postmitotic neuron cells at a time point, wherein the detected protein chain of the XRI subunits provides the temporal history of the chain of the expressed XRI subunits in the postmitotic neuron cell or the plurality of postmitotic neuron cells at the time point.

8. The method of claim 7, wherein detecting the expressed chain of the XRI subunits in the plurality of postmitotic neuron cells comprises detecting the expressed chain of the XRI subunits in one or more postmitotic neuron cells obtained from the plurality of postmitotic neuron cells.

9. The method of claim 7, wherein the plurality of independently selected XRI subunits comprises different encoded XRI subunits.

10. The method of claim 7, wherein the method further comprises detecting the expressed chains of the XRI subunits in the plurality of postmitotic neuron cells at one or more additional independently selected time points providing a plurality of detections of detected expressed chains of the XRI subunits and identifying an expression record of the chains of the XRI subunits in the plurality of postmitotic neuron cells across the plurality of time points.

11. A method of identifying an effect of a candidate stimulus on expression in a cell, comprising preparing a plurality of postmitotic eukaryotic neuron cells comprising a plurality of expressed expression recording island (XRI) subunits in the soma of a postmitotic neuron cell wherein the expressed XRI subunits comprise:

one or more of an independently selected self-assembling filament-forming monomer, wherein the independently selected self-assembling filament-forming monomer is selected from a 1POK and a DHF40 protein;

one or more independently selected detectable tag, and one or more independently selected protein spacer; wherein the independently selected protein spacer is a monomeric protein selected from mEGFP and a maltose binding protein (MBP) and is fused to a lateral edge of the expressed self-assembling filament-forming monomer; and wherein, the plurality of expressed XRI subunits is a linear chain of the expressed XRI subunits in the soma of the postmitotic neuron cell and the XRI subunits form growing protein chains in the soma of the postmitotic neuron cells, the independently selected spacer sterically blocks lateral growth of the growing protein chains, and the growing protein chains provide a temporal history of the expression of the XRI subunits in the chains;

exposing the plurality of postmitotic neuron cells expressing the XRI subunits to a candidate stimulus;

detecting the protein chains of the XRI subunits in one or more postmitotic neuron cells in the exposed plurality of postmitotic neuron cells, and comparing the detected protein chains of the XRI subunits in the one or more postmitotic neuron cells to a control expressed protein chain of the XRI subunits, wherein the control expressed chain of the XRI subunits is the chain of the expressed XRI subunits in a postmitotic neuron cell comprising the expressed XRI subunits but not exposed to the candidate stimulus; and wherein a difference in the detected protein chain of XRI subunits in the exposed postmitotic neuron cells compared to the control expressed protein chain of XRI subunits identifies an effect of the candidate stimulus on the XRI subunit expression.

* * * * *

SEQUENCE LISTING

```
Sequence total quantity: 31
SEQ ID NO: 1            moltype = AA  length = 390
FEATURE                 Location/Qualifiers
source                  1..390
                        mol_type = protein
                        organism = synthetic construct
SEQUENCE: 1
MIDYTAAGFT LLQGAHLYAP EDRGICDVLV ANGKIIAVAS NIPSDIVPNC TVVDLSGQIL  60
CPGFIDQHVH LIGGGGEAGP TTRTPEVALS RLTEAGVTSV VGLLGTDSIS RHPESLLAKT  120
RALNEEGISA WMLTGAYHVP SRTITGSVEK DVAIIDRVIG VKCAISDHRS AAPDVYHLAN  180
MAAESRVGGL LGGKPGVTVF HMGDSKKALQ PIYDLLENCD VPISKLLPTH VNRNVPLFYQ  240
ALEFARKGGT IDITSSIDEP VAPAEGIARA VQAGIPLARV TLSSDGNGSQ PFFDDEGNLT  300
HIGVAGFETL LETVQVLVKD YDFSISDALR PLTSSVAGFL NLTGKGEILP GNDADLLVMT  360
PELRIEQVYA RGKLMVKDGK ACVKGTFETA                                  390

SEQ ID NO: 2            moltype = AA  length = 366
FEATURE                 Location/Qualifiers
source                  1..366
                        mol_type = protein
                        organism = synthetic construct
SEQUENCE: 2
KIEEGKLVIW INGDKGYNGL AEVGKKFEKD TGIKVTVEHP DKLEEKFPQV AATGDGPDII  60
FWAHDRFGGY AQSGLLAEIT PDKAFQDKLY PFTWDAVRYN GKLIAYPIAV EALSLIYNKD  120
LLPNPPKTWE EIPALDKELK AKGKSALMFN LQEPYFTWPL IAADGGYAFK YENGKYDIKD  180
VGVDNAGAKA GLTFLVDLIK NKHMNADTDY SIAEAAFNKG ETAMTINGPW AWSNIDTSKV  240
NYGVTVLPTF KGQPSKPFVG VLSAGINAAS PNKELAKEFL ENYLLTDEGL EAVNKDKPLG  300
AVALKSYEEE LAKDPRIAAT MENAQKGEIM PNIPQMSAFW YAVRTAVINA ASGRQTVDEA  360
LKDAQT                                                            366

SEQ ID NO: 3            moltype = AA  length = 9
FEATURE                 Location/Qualifiers
source                  1..9
                        mol_type = protein
                        organism = synthetic construct
SEQUENCE: 3
YPYDVPDYA                                                         9

SEQ ID NO: 4            moltype = AA  length = 8
FEATURE                 Location/Qualifiers
source                  1..8
                        mol_type = protein
                        organism = synthetic construct
SEQUENCE: 4
DYKDDDDK                                                          8

SEQ ID NO: 5            moltype = AA  length = 14
FEATURE                 Location/Qualifiers
source                  1..14
                        mol_type = protein
                        organism = synthetic construct
SEQUENCE: 5
```

-continued

```
GKPIPNPLLG LDST                                              14

SEQ ID NO: 6          moltype = AA  length = 264
FEATURE               Location/Qualifiers
source                1..264
                      mol_type = protein
                      organism = synthetic construct
SEQUENCE: 6
MKPTTISLLQ KYKQEKKRFA TITAYDYSFA KLFADEGLNV MLVGDSLGMT VQGHDSTLPV  60
TVADIAYHTA AVRRGAPNCL LLADLPFMAY ATPEQAFENA ATVMRAGANM VKIEGGEWLV  120
ETVQMLTERA VPVCGHLGLT PQSVNIFGGY KVQGRGLLAG LQLLSDALAL EAAGAQLLVL  180
ECVPVELAKR ITEALAIPVI GIGAGNVTDG QILVMHDAFG ITGGHIPKFA KNFLAETGDI  240
RAAVRQYMAE VESGVYPGEE HSFH                                       264

SEQ ID NO: 7          moltype = AA  length = 152
FEATURE               Location/Qualifiers
source                1..152
                      mol_type = protein
                      organism = synthetic construct
SEQUENCE: 7
MENYLIDNLD RGILEALMGN ARTAYAELAK QFGVSPETIH VRVEKMKQAG IITGARIDVS  60
PKQLGYDVGC FIGIILKSAK DYPSALAKLE SLDEVTEAYY TTGHYSIFIK VMCRSIDALQ  120
HVLINYIQTI YEIQSTETLI VLQNPIMRTI KP                              152

SEQ ID NO: 8          moltype = AA  length = 755
FEATURE               Location/Qualifiers
source                1..755
                      mol_type = protein
                      organism = synthetic construct
SEQUENCE: 8
MKVLIVESEF LHQDTWVGNA VERLADALSQ QNVTVIKSTS FDDGFAILSS NEAIDCLMFS  60
YQMEHPDEHQ NVRQLIGKLH ERQQNVPVFL LGDREKALAA MDRDLLELVD EFAWILEDTA  120
DFIAGRAVAA MTRYRQQLLP PLFSALMKYS DIHEYSWAAP GHQGGVGFTK TPAGRFYHDY  180
YGENLFRTDM GIERTSLGSL LDHTGAFGES EKYAARVFGA DRSWSVVVGT SGSNRTIMQA  240
CMTDNDVVVV DRNCHKSIEQ GLMLTGAKPV YMVPSRNRYG IIGPIYPQEM QPETLQKKIS  300
ESPLTKDKAG QKPSYCVVTN CTYDGVCYNA KEAQDLLEKT SDRLHFDEAW YGYARFNPIY  360
ADHYAMRGEP GDHNGPTVFA THSTHKLLNA LSQASYIHVR EGRGAINFSR FNQAYMMHAT  420
TSPLYAICAS NDVAVSMMDG NSGLSLTQEV IDEAVDFRQA MARLYKEFTA DGSWFFKPWN  480
KEVVTDPQTG LTYLFALAPT KLLTTVQDCW VMHPGESWHG FKDIPDNWSM LDPIKVSILA  540
PGMGEDGELE ETGVPAALVT AWLGRHGIVP TRTTDFQIMF LFSMGVTRGK WGTLVNTLCS  600
FKRHYDANTP LAQVMPELVE QYPDTYANMG IHDLGDTMFA WLKENNPGAR LNEAYSGLPV  660
AEVTPREAYN AIVDNNVELV SIENLPGRIA ANSVIPYPPG IPMLLSGENF GDKNSPQVSY  720
LRSLQSWDHH FPGFEHETEG TEIIDGIYHV MCVKA                           755

SEQ ID NO: 9          moltype = AA  length = 201
FEATURE               Location/Qualifiers
source                1..201
                      mol_type = protein
                      organism = synthetic construct
SEQUENCE: 9
MSSEKEELRE RLVKICVELA KLKGDDTLKA AEAAEEAFRL VVLAAMLAGI DSSEVLELAI  60
RLIKTCVVLA AMEGYDISEA CRAAAEAFTR VAMAALRAGI TSSLVLKAAI ELIKECVLNA  120
AVEGYDISEA CRAAAEAFKR VAEAAKRAGI TSLETLLRAI EEIRKRVEEA QREGNDISEA  180
CRQAAEEFRK KAEELKRRGD V                                          201

SEQ ID NO: 10         moltype = AA  length = 147
FEATURE               Location/Qualifiers
source                1..147
                      mol_type = protein
                      organism = synthetic construct
SEQUENCE: 10
MVNEVIDINE AVRAYIAQIE GLRAEIGRLD ATIATLRQSL ATLKSLKTLG EGKTVLVPVG  60
SIAQVEMKVE KMDKVVVSVG QNISAELEYE EALKYIEDEI KKLLTFRLVL EQAIAELYAK  120
IEDLIAEAQQ TSEEEKAEEE ENEEKAE                                    147

SEQ ID NO: 11         moltype = AA  length = 93
FEATURE               Location/Qualifiers
source                1..93
                      mol_type = protein
                      organism = synthetic construct
SEQUENCE: 11
DIQVQVNIDD NGKNFDYTYT VTTESELQKV LNELKDYIKK QGAKRVRISI TARTKKEAEK  60
FAAILIKVFA ELGYNDINVT WDGDTVTVEG QLE                             93

SEQ ID NO: 12         moltype = AA  length = 379
FEATURE               Location/Qualifiers
source                1..379
                      mol_type = protein
                      organism = synthetic construct
```

-continued

```
SEQUENCE: 12
GSSMASGISV EELLKLAKAA YYSGTTVEEA YKLALKLGIS VEELLKLAEA AYYSGTTVEE  60
AYKLALKLGI SVEELLKLAK AAYYSGTTVE EAYKLALKLG ISVEELLKLA KAAYYSGTTV  120
EEAYKLALKL GISVEELLKL AEAAYYSGTT VEEAYKLALK LGISVEELLK LAKAAYYSGT  180
TVEEAYKLAL KLGISVEELL KLAKAAYYSG TTVEEAYKLA LKLGISVEEL LKLAEAAYYS  240
GTTVEEAYKL ALKLGISVEE LLKLAKAAYY SGTTVEEAYK LALKLGISVE ELLKLAKAAY  300
YSGTTVEEAY KLALKLGISV EELLKLAEAA YYSGTTVEEA YKLALKLGIS VEELLKLAKA  360
AYYSGTTVEE AYKLALKLG                                               379

SEQ ID NO: 13          moltype = AA  length = 974
FEATURE                Location/Qualifiers
source                 1..974
                       mol_type = protein
                       organism = synthetic construct
SEQUENCE: 13
MAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPVK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDLLL EAADAHRLHA PTSRGGASVE ETDQSHLATA GSTSSHSLQK  300
YYITGEAEGF PATAVDNLLT VHQNLPALPV DATSDEVRKN LMDMFRDRQA FSEHTWKMLL  360
SVCRSWAAWC KLNNRKWFPA EPEDVRDYLL YLQARGLAVK TIQQHLGQLN MLHRRSGLPR  420
PSDSNAVSLV MRRIRKENVD AGERAKQALA FERTDFDQVR SLMENSDRCQ DIRNLAFLGI  480
AYNTLLRIAE IARIRVKDIS RTDGGRMLIH IGRTKTLVST AGVEKALSLG VTKLVERWIS  540
VSGVADDPNN YLFCRVRKNG VAAPSATSQL STRALEGIFE ATHRLIYGAK DDSGQRYLAW  600
SGHSARVGAA RDMARAGVSI PEIMQAGGWT NVNIVMNYIR NLDSETGAMV RLLEDGDLEP  660
SAGDMRAANL WPSPLMIKRS KKNSLALSLT ADQMVSALLD AEPPILYSEY DPTRPFSEAS  720
MMGLLTNLAD RELVHMINWA KRVPGFVDLT LHDQVHLLEC AWLEILMIGL VWRSMEHPVK  780
LLFAPNLLLD RNQGKCVEGM VEIFDMLLAT SSRFRMMNLQ GEEFVCLKSI ILLNSGVYTF  840
LSSTLKSLEE KDHIHRVLDK ITDTLIHLMA KAGLTLQQQH QRLAQLLLIL SHIRHMSNKG  900
MEHLYSMKCK NVVPLYDLLL EAADAHRLHA PTSRGGASVE ETDQSHLATA GSTSSHSLQK  960
YYITGEAEGF PATA                                                    974

SEQ ID NO: 14          moltype = AA  length = 7
FEATURE                Location/Qualifiers
source                 1..7
                       mol_type = protein
                       organism = synthetic construct
SEQUENCE: 14
PKKKRKV                                                            7

SEQ ID NO: 15          moltype = AA  length = 4
FEATURE                Location/Qualifiers
source                 1..4
                       mol_type = protein
                       organism = synthetic construct
SEQUENCE: 15
GSGG                                                               4

SEQ ID NO: 16          moltype = AA  length = 5
FEATURE                Location/Qualifiers
source                 1..5
                       mol_type = protein
                       organism = synthetic construct
SEQUENCE: 16
GGGSG                                                              5

SEQ ID NO: 17          moltype = AA  length = 6
FEATURE                Location/Qualifiers
source                 1..6
                       mol_type = protein
                       organism = synthetic construct
SEQUENCE: 17
GGSGGT                                                             6

SEQ ID NO: 18          moltype = AA  length = 7
FEATURE                Location/Qualifiers
source                 1..7
                       mol_type = protein
                       organism = synthetic construct
SEQUENCE: 18
GGSGGTG                                                            7

SEQ ID NO: 19          moltype = AA  length = 8
FEATURE                Location/Qualifiers
source                 1..8
                       mol_type = protein
                       organism = synthetic construct
SEQUENCE: 19
```

-continued

```
GGSGGTGG                                                 8

SEQ ID NO: 20          moltype = AA  length = 12
FEATURE                Location/Qualifiers
source                 1..12
                       mol_type = protein
                       organism = synthetic construct
SEQUENCE: 20
GGSGGTGGSG GT                                            12

SEQ ID NO: 21          moltype = AA  length = 14
FEATURE                Location/Qualifiers
source                 1..14
                       mol_type = protein
                       organism = synthetic construct
SEQUENCE: 21
GGSGGTGGSG GTGG                                          14

SEQ ID NO: 22          moltype = AA  length = 13
FEATURE                Location/Qualifiers
source                 1..13
                       mol_type = protein
                       organism = synthetic construct
SEQUENCE: 22
GGSGGTGGSG GTG                                           13

SEQ ID NO: 23          moltype = AA  length = 18
FEATURE                Location/Qualifiers
source                 1..18
                       mol_type = protein
                       organism = synthetic construct
SEQUENCE: 23
GGSGGTGGSG GTGGSGGT                                      18

SEQ ID NO: 24          moltype = AA  length = 24
FEATURE                Location/Qualifiers
source                 1..24
                       mol_type = protein
                       organism = synthetic construct
SEQUENCE: 24
GGSGGTGGSG GTGGSGGTGG SGGT                               24

SEQ ID NO: 25          moltype = AA  length = 25
FEATURE                Location/Qualifiers
source                 1..25
                       mol_type = protein
                       organism = synthetic construct
SEQUENCE: 25
GGSGGTGGSG GTGGSGGTGG SGGTG                              25

SEQ ID NO: 26          moltype = AA  length = 793
FEATURE                Location/Qualifiers
source                 1..793
                       mol_type = protein
                       organism = synthetic construct
SEQUENCE: 26
MIDYTAAGFT LLQGAHLYAP EDRGICDVLV ANGKIIAVAS NIPSDIVPNC TVVDLSGQIL  60
CPGFIDQHVH LIGGGGEAGP TTRTPEVALS RLTEAGVTSV VGLLGTDSIS RHPESLLAKT  120
RALNEEGISA WMLTGAYHVP SRTITGSVEK DVAIIDRVIG VKCAISDHRS AAPDVYHLAN  180
MAAESRVGGL LGGKPGVTVF HMGDSKKALQ PIYDLLENCD VPISKLLPTH VNRNVPLFYQ  240
ALEFARKGGT IDITSSIDEP VAPAEGIARA VQAGIPLARV TLSSDGNGSQ PFFDDEGNLT  300
HIGVAGFETL LETVQVLVKD YDFSISDALR PLTSSVAGFL NLTGKGEILP GNDADLLVMT  360
PELRIEQVYA RGKLMVKDGK ACVKGTFETA GGSGGTGGSG GTGGSGGTGG SGGTGYPYDV  420
PDYAGSGKIE EGKLVIWING DKGYNGLAEV GKKFEKDTGI KVTVEHPDKL EEKFPQVAAT  480
GDGPDIIFWA HDRFGGYAQS GLLAEITPDK AFQDKLYPFT WDAVRYNGKL IAYPIAVEAL  540
SLIYNKDLLP NPPKTWEEIP ALDKELKAKG KSALMFNLQE PYFTWPLIAA DGGYAFKYEN  600
GKYDIKDVGV DNAGAKAGLT FLVDLIKNKH MNADTDYSIA EAAFNKGETA MTINGPWAWS  660
NIDTSKVNYG VTVLPTFKGQ PSKPFVGVLS AGINAASPNK ELAKEFLENY LLTDEGLEAV  720
NKDKPLGAVA LKSYEEELAK DPRIAATMEN AQKGEIMPNI PQMSAFWYAV RTAVINAASG  780
RQTVDEALKD AQT                                           793

SEQ ID NO: 27          moltype = DNA  length = 2379
FEATURE                Location/Qualifiers
source                 1..2379
                       mol_type = other DNA
                       organism = synthetic construct
SEQUENCE: 27
atgattgact atactgctgc tggtttcacc ctcctccaag gtgcacatct gtacgctcct  60
gaagacagag gtatctgcga tgtgctggtt gccaacggta agatcatcgc tgtggcctcc  120
```

-continued

```
aacattccta gcgacatcgt tccaaactgc accgttgtcg atctgagcgg acagatcctc  180
tgtccaggat tcattgatca gcacgtgcac ctcattggag gaggaggcga agctggtcct  240
actactagaa ctcccgaagt cgcactgtct cgcctcacag aggcaggcgt tacctccgtc  300
gtgggactcc tgggtactga tagcatctct aggcaccctg agtctctgct ggcaaagacc  360
agagccctca atgaggaggg tatctccgct tggatgctga ctggtgctta tcacgtccca  420
tctcgcacca ttactggcag cgtggagaag gacgttgcaa tcatcgacag agtgatcggt  480
gttaagtgcg ctatctccga ccacaggagc gctgctcccg acgtctatca cctggccaac  540
atggcagccg agagcagagt cggtggtctg ctcggtggca agccaggagt taccgtgttc  600
cacatgggtg actctaagaa ggcactgcaa cccatctatg acctgctgga gaactgtgac  660
gtcccaatct ccaagctgct gcctacccac gtcaacagga acgtgcctct cttctaccaa  720
gctctggagt tcgcaagaaa gggtggcacc atcgacatca cctctagcat tgatgaaccc  780
gtcgctccag ctgagggaat cgcaagggct gtccaagcag gtatcccact ggcaagggtg  840
acactcagct ctgatggcaa cggctcccag ccattcttcg atgatgaagg aaatctgact  900
cacattggcg tggctggatt tgaaactctc ctggaaacag ttcaggttct ggttaaggac  960
tacgacttca gcatttctga cgctctcaga ccactcacct ctagcgtcgc tggcttcctg  1020
aacctgactg gtaaaggcga aatcctccct ggtaatgacg ctgatctgct ggtgatgaca  1080
cccgaactgc gcattgagca ggtctatgca agaggaaagc tgatggttaa ggacggaaag  1140
gcttgtgtca agggcacatt cgagactgct ggtggctctg gaggcaccgg agggtctgga  1200
gggactggag gctctggagg tactggcggt tctggaggta ccggttaccc atacgatgtg  1260
cctgattacg caggatccgg taagattgaa gagggcaaac tggttatctg gatcaatggc  1320
gataagggct acaatggcct ggcagaggtc ggtaagaagt tcgagaaaga tacaggcatc  1380
aaagttactg tggaacaccc agataagctg gaggagaagt tccctcaggt cgcagcaact  1440
ggcgacggtc cagacatcat cttctgggca cacgataggt tcggtggcta tgcccaatct  1500
ggcctgctgg ctgagattac tcctgataag gctttccagg acaagctgta tccattcacc  1560
tgggatgctg tgagatacaa tggcaagctg atcgcatacc ctattgctgt ggaagctctg  1620
agcctgatct acaacaagga cctgctgcct aatcctccta agacatggga agaaatccct  1680
gcactggaca aggaactgaa ggccaaaggc aagtccgcac tgatgttcaa cctgcaggag  1740
ccttacttta cctggccact gattgctgcc gacggtggtt acgctttcaa gtacgagaat  1800
ggtaagtacg acatcaaaga tgtgggtgtg gacaatgctg gtgccaaagc tggtctgact  1860
ttcctggtgg atctgatcaa gaacaagcac atgaatgcag acactgacta ttctatcgca  1920
gaggctgctt tcaacaaagg cgaaaccgca atgactatca atggtccttg ggcatggtct  1980
aacatcgaca ctagcaaagt caactacggt gtcaccgttc tgccaacctt caagggtcag  2040
ccaagcaaac ctttcgttgg cgtgctgagc gcaggtatca acgctgcctc tcctaacaaa  2100
gagctggcta aggagtttct ggagaactac ctgctgacag acgaaggtct ggaggcagtg  2160
aacaaggaca agccactggg tgccgtggct ctgaagagct acgaagaaga actggccaag  2220
gaccctcgca tcgctgctac aatggagaac gcacagaagg gtgagatcat gccaaacatc  2280
ccacagatga gcgcattctg gtatgccgtg aggaccgctg ttatcaacgc agcttctggc  2340
agacagaccg tggatgaagc cctgaaagac gcacagacc                         2379

SEQ ID NO: 28          moltype = AA  length = 792
FEATURE                Location/Qualifiers
source                 1..792
                       mol_type = protein
                       organism = synthetic construct
SEQUENCE: 28
MIDYTAAGFT LLQGAHLYAP EDRGICDVLV ANGKIIAVAS NIPSDIVPNC TVVDLSGQIL  60
CPGFIDQHVH LIGGGGEAGP TTRTPEVALS RLTEAGVTSV VGLLGTDSIS RHPESLLAKT  120
RALNEEGISA WMLTGAYHVP SRTITGSVEK DVAIIDRVIG VKCAISDHRS AAPDVYHLAN  180
MAAESRVGGL LGGKPGVTVF HMGDSKKALQ PIYDLLENCD VPISKLLPTH VNRNVPLFYQ  240
ALEFARKGGT IDITSSIDEP VAPAEGIARA VQAGIPLARV TLSSDGNGSQ PFFDDEGNLT  300
HIGVAGFETL LETVQVLVKD YDFSISDALR PLTSSVAGFL NLTGKGEILP GNDADLLVMT  360
PELRIEQVYA RGKLMVKDGK ACVKGTFETA GGSGGTGGSG GTGGSGGTGG SGGTGDYKDD  420
DDKGSGKIEE GKLVIWINGD KGYNGLAEVG KKFEKDTGIK VTVEHPDKLE EKFPQVAATG  480
DGPDIIFWAH DRFGGYAQSG LLAEITPDKA FQDKLYPFTW DAVRYNGKLI AYPIAVEALS  540
LIYNKDLLPN PPKTWEEIPA LDKELKAKGK SALMFNLQEP YFTWPLIAAD GGYAFKYENG  600
KYDIKDVGVD NAGAKAGLTF LVDLIKNKHM NADTDYSIAE AAFNKGETAM TINGPWAWSN  660
IDTSKVNYGV TVLPTFKGQP SKPFVGVLSA GINAASPNKE LAKEFLENYL LTDEGLEAVN  720
KDKPLGAVAL KSYEEELAKD PRIAATMENA QKGEIMPNIP QMSAFWYAVR TAVINAASGR  780
QTVDEALKDA QT                                                      792

SEQ ID NO: 29          moltype = DNA  length = 2376
FEATURE                Location/Qualifiers
source                 1..2376
                       mol_type = other DNA
                       organism = synthetic construct
SEQUENCE: 29
atgattgact atactgctgc tggtttcacc ctcctccaag gtgcacatct gtacgctcct  60
gaagacagag gtatctgcga tgtgctggtt gccaacggta agatcatcgc tgtggcctcc  120
aacattccta gcgacatcgt tccaaactgc accgttgtcg atctgagcgg acagatcctc  180
tgtccaggat tcattgatca gcacgtgcac ctcattggag gaggaggcga agctggtcct  240
actactagaa ctcccgaagt cgcactgtct cgcctcacag aggcaggcgt tacctccgtc  300
gtgggactcc tgggtactga tagcatctct aggcaccctg agtctctgct ggcaaagacc  360
agagccctca atgaggaggg tatctccgct tggatgctga ctggtgctta tcacgtccca  420
tctcgcacca ttactggcag cgtggagaag gacgttgcaa tcatcgacag agtgatcggt  480
gttaagtgcg ctatctccga ccacaggagc gctgctcccg acgtctatca cctggccaac  540
atggcagccg agagcagagt cggtggtctg ctcggtggca agccaggagt taccgtgttc  600
cacatgggtg actctaagaa ggcactgcaa cccatctatg acctgctgga gaactgtgac  660
gtcccaatct ccaagctgct gcctacccac gtcaacagga acgtgcctct cttctaccaa  720
gctctggagt tcgcaagaaa gggtggcacc atcgacatca cctctagcat tgatgaaccc  780
```

-continued

```
gtcgctccag ctgagggaat cgcaagggct gtccaagcag gtatcccact ggcaagggtg  840
acactcagct ctgatggcaa cggctcccag ccattcttcg atgatgaagg aaatctgact  900
cacattggcg tggctggatt tgaaactctc ctggaaacag ttcaggttct ggttaaggac  960
tacgacttca gcatttctga cgctctcaga ccactcacct ctagcgtcgc tggcttcctg  1020
aacctgactg gtaaaggcga aatcctccct ggtaatgacg ctgatctgct ggtgatgaca  1080
cccgaactgc gcattgagca ggtctatgca agaggaaagc tgatggttaa ggacggaaag  1140
gcttgtgtca agggcacatt cgagactgct ggtggctctg gaggcaccgg agggtctgga  1200
gggactggag gctctggagg tactggcggt tctggaggta ccggtgacta caaggacgat  1260
gatgacaaag gatccggtaa gattgaagag ggcaaactgg ttatctggat caatggcgat  1320
aagggctaca atggcctggc agaggtcggt aagaagttcg agaaagatac aggcatcaaa  1380
gttactgtgg aacacccaga taagctggag gagaagttcc ctcaggtcgc agcaactggc  1440
gacggtccag acatcatctt ctgggcacac gataggttcg gtggctatgc ccaatctggc  1500
ctgctggctg agattactcc tgataaggct ttccaggaca agctgtatcc attcacctgg  1560
gatgctgtga gatacaatgg caagctgatc gcatacccta ttgctgtgga agctctgagc  1620
ctgatctaca acaaggacct gctgcctaat cctcctaaga catgggaaga aatccctgca  1680
ctggacaagg aactgaaggc caaaggcaag tccgcactga tgttcaacct gcaggagcct  1740
tactttacct ggccactgat tgctgccgac ggtggttacg ctttcaagta cgagaatggt  1800
aagtacgaca tcaaagatgt gggtgtggac aatgctggtg ccaaagctgg tctgactttc  1860
ctggtggatc tgatcaagaa caagcacatg aatgcagaca ctgactattc tatcgcagag  1920
gctgctttca acaaaggcga aaccgcaatg actatcaatg gtccttgggc atggtctaac  1980
atcgacacta gcaaagtcaa ctacggtgtc accgttctgc caaccttcaa gggtcagcca  2040
agcaaacctt tcgttggcgt gctgagcgca ggtatcaacg ctgcctctcc taacaaagag  2100
ctggctaagg agtttctgga gaactacctg ctgacagacg aaggtctgga ggcagtgaac  2160
aaggacaagc cactgggtgc cgtggctctg aagagctacg aagaagaact ggccaaggac  2220
cctcgcatcg ctgctacaat ggagaacgca cagaagggtg agatcatgcc aaacatccca  2280
cagatgagcg cattctggta tgccgtgagg accgctgtta tcaacgcagc ttctggcaga  2340
cagaccgtgg atgaagccct gaaagacgca cagacc                           2376

SEQ ID NO: 30          moltype = AA  length = 798
FEATURE                Location/Qualifiers
source                 1..798
                       mol_type = protein
                       organism = synthetic construct
SEQUENCE: 30
MIDYTAAGFT LLQGAHLYAP EDRGICDVLV ANGKIIAVAS NIPSDIVPNC TVVDLSGQIL  60
CPGFIDQHVH LIGGGGEAGP TTRTPEVALS RLTEAGVTSV VGLLGTDSIS RHPESLLAKT  120
RALNEEGISA WMLTGAYHVP SRTITGSVEK DVAIIDRVIG VKCAISDHRS AAPDVYHLAN  180
MAAESRVGGL LGGKPGVTVF HMGDSKKALQ PIYDLLENCD VPISKLLPTH VNRNVPLFYQ  240
ALEFARKGGT IDITSSIDEP VAPAEGIARA VQAGIPLARV TLSSDGNGSQ PFFDDEGNLT  300
HIGVAGFETL LETVQVLVKD YDFSISDALR PLTSSVAGFL NLTGKGEILP GNDADLLVMT  360
PELRIEQVYA RGKLMVKDGK ACVKGTFETA GGSGGTGGSG GTGGSGGTGG SGGTGGKPIP  420
NPLLGLDSTG SGKIEEGKLV IWINGDKGYN GLAEVGKKFE KDTGIKVTVE HPDKLEEKFP  480
QVAATGDGPD IIFWAHDRFG GYAQSGLLAE ITPDKAFQDK LYPFTWDAVR YNGKLIAYPI  540
AVEALSLIYN KDLLPNPPKT WEEIPALDKE LKAKGKSALM FNLQEPYFTW PLIAADGGYA  600
FKYENGKYDI KDVGVDNAGA KAGLTFLVDL IKNKHMNADT DYSIAEAAFN KGETAMTING  660
PWAWSNIDTS KVNYGVTVLP TFKGQPSKPF VGVLSAGINA ASPNKELAKE FLENYLLTDE  720
GLEAVNKDKP LGAVALKSYE EELAKDPRIA ATMENAQKGE IMPNIPQMSA FWYAVRTAVI  780
NAASGRQTVD EALKDAQT                                                798

SEQ ID NO: 31          moltype = DNA  length = 2394
FEATURE                Location/Qualifiers
source                 1..2394
                       mol_type = other DNA
                       organism = synthetic construct
SEQUENCE: 31
atgattgact atactgctgc tggtttcacc ctcctccaag gtgcacatct gtacgctcct  60
gaagacagag gtatctgcga tgtgctggtt gccaacggta agatcatcgc tgtggcctcc  120
aacattccta gcgacatcgt tccaaactgc accgttgtcg atctgagcgg acagatcctc  180
tgtccaggat tcattgatca gcacgtgcac ctcattggag gaggaggcga agctggtcct  240
actactagaa ctcccgaagt cgcactgtct cgcctcacag aggcaggcgt tacctccgtc  300
gtgggactcc tgggtactga tagcatctct aggcaccctg agtctctgct ggcaaagacc  360
agagccctca atgaggaggg tatctccgct tggatgctga ctggtgctta tcacgtccca  420
tctcgcacca ttactggcag cgtggagaag gacgttgcaa tcatcgacag agtgatcggt  480
gttaagtgcg ctatctccga ccacaggagc gctgctcccg acgtctatca cctggccaac  540
atggcagccg agagcagagt cggtggtctg ctcggtggca agccaggagt taccgtgttc  600
cacatgggtg actctaagaa ggcactgcaa cccatctatg acctgctgga gaactgtgac  660
gtcccaatct ccaagctgct gcctacccac gtcaacagga acgtgcctct cttctaccaa  720
gctctggagt tcgcaagaaa gggtggcacc atcgacatca cctctagcat tgatgaaccc  780
gtcgctccag ctgagggaat cgcaagggct gtccaagcag gtatcccact ggcaagggtg  840
acactcagct ctgatggcaa cggctcccag ccattcttcg atgatgaagg aaatctgact  900
cacattggcg tggctggatt tgaaactctc ctggaaacag ttcaggttct ggttaaggac  960
tacgacttca gcatttctga cgctctcaga ccactcacct ctagcgtcgc tggcttcctg  1020
aacctgactg gtaaaggcga aatcctccct ggtaatgacg ctgatctgct ggtgatgaca  1080
cccgaactgc gcattgagca ggtctatgca agaggaaagc tgatggttaa ggacggaaag  1140
gcttgtgtca agggcacatt cgagactgct ggtggctctg gaggcaccgg agggtctgga  1200
gggactggag gctctggagg tactggcggt tctggaggta ccggtggtaa gcctatccct  1260
aaccctctgc tcggtctcga ttctaccgga tccggtaaga ttgaagaggg caaactggtt  1320
atctggatca atggcgataa gggctacaat ggcctggcag aggtcggtaa gaagttcgag  1380
aaagatacag gcatcaaagt tactgtggaa cacccagata agctggagga gaagttccct  1440
```

-continued

```
caggtcgcag caactggcga cggtccagac atcatcttct gggcacacga taggttcggt  1500
ggctatgccc aatctggcct gctggctgag attactcctg ataaggcttt ccaggacaag  1560
ctgtatccat tcacctggga tgctgtgaga tacaatggca agctgatcgc ataccctatt  1620
gctgtggaag ctctgagcct gatctacaac aaggacctgc tgcctaatcc tcctaagaca  1680
tgggaagaaa tccctgcact ggacaaggaa ctgaaggcca aaggcaagtc cgcactgatg  1740
ttcaacctgc aggagcctta ctttacctgg ccactgattg ctgccgacgg tggttacgct  1800
ttcaagtacg agaatggtaa gtacgacatc aaagatgtgg gtgtggacaa tgctggtgcc  1860
aaagctggtc tgactttcct ggtggatctg atcaagaaca agcacatgaa tgcagacact  1920
gactattcta tcgcagaggc tgctttcaac aaaggcgaaa ccgcaatgac tatcaatggt  1980
ccttgggcat ggtctaacat cgacactagc aaagtcaact acggtgtcac cgttctgcca  2040
accttcaagg gtcagccaag caaacctttc gttggcgtgc tgagcgcagg tatcaacgct  2100
gcctctccta acaaagagct ggctaaggag tttctggaga actacctgct gacagacgaa  2160
ggtctggagg cagtgaacaa ggacaagcca ctgggtgccg tggctctgaa gagctacgaa  2220
gaagaactgg ccaaggaccc tcgcatcgct gctacaatgg agaacgcaca gaagggtgag  2280
atcatgccaa acatcccaca gatgagcgca ttctggtatg ccgtgaggac cgctgttatc  2340
aacgcagctt ctggcagaca gaccgtggat gaagccctga aagacgcaca gacc        2394
```